United States Patent [19]
DiStasio et al.

[11] Patent Number: 6,010,289
[45] Date of Patent: Jan. 4, 2000

[54] LOCKING NUT, BOLT AND CLIP SYSTEMS AND ASSEMBLIES

[75] Inventors: Robert J. DiStasio, Vahalla, N.Y.; Stephen G. Bowling, Stamford; William Kurt Feick, New Canaan, both of Conn.

[73] Assignee: Permanent Technologies, Inc., Massapequa Park, N.Y.

[21] Appl. No.: 09/056,292

[22] Filed: Apr. 7, 1998

Related U.S. Application Data

[63] Continuation-in-part of application No. 08/747,323, Nov. 12, 1996
[60] Provisional application No. 60/015,230, Apr. 10, 1996, provisional application No. 60/015,980, Apr. 15, 1996, and provisional application No. 60/050,467, Jun. 23, 1997.

[51] Int. Cl.[7] .............................. F16B 37/62; F16B 39/22
[52] U.S. Cl. .......................... 411/174; 411/299; 411/326; 411/951
[58] Field of Search ..................................... 411/174, 175, 411/112, 296, 299, 300, 326, 327, 329, 941.1, 950, 951, 952, 114, 115, 7

[56] References Cited

U.S. PATENT DOCUMENTS

| | | |
|---|---|---|
| 307,722 | 11/1884 | Klemroth et al. . |
| 439,754 | 11/1890 | Thompson . |
| 589,599 | 9/1897 | Hardy . |
| 591,062 | 10/1897 | Smith . |
| 785,528 | 3/1905 | Thompson . |
| 827,289 | 7/1906 | Bowers . |
| 1,019,686 | 3/1912 | Miller . |
| 1,020,668 | 3/1912 | Thompson . |
| 1,086,980 | 2/1914 | Badcock . |
| 1,088,892 | 3/1914 | Foreman . |
| 1,089,159 | 3/1914 | Santarcangelo . |
| 1,136,310 | 4/1915 | Burnett . |
| 1,153,898 | 9/1915 | Duckett . |
| 1,208,210 | 12/1916 | Purcell . |
| 1,221,194 | 4/1917 | Lang . |
| 1,226,143 | 5/1917 | Stubblefield et al. . |
| 1,245,362 | 11/1917 | Lynch . |
| 1,278,028 | 9/1918 | Savory et al. . |
| 1,352,103 | 9/1920 | Thibert . |
| 1,364,553 | 1/1921 | Hilsabeck . |
| 1,465,148 | 8/1923 | Rosenberg . |
| 1,554,338 | 9/1925 | Duckett . |
| 1,703,947 | 3/1929 | Nation . |
| 1,934,439 | 11/1933 | Messmer . |
| 2,106,669 | 1/1938 | Thornton . |
| 2,232,336 | 2/1941 | Meersteiner . |
| 2,301,181 | 11/1942 | Ilsemann . |
| 2,342,170 | 2/1944 | Tinnerman . |
| 2,398,827 | 4/1946 | Graham et al. . |

(List continued on next page.)

FOREIGN PATENT DOCUMENTS

| | | | |
|---|---|---|---|
| 2835675 | 2/1980 | Germany | ................................ 411/174 |
| 142748 | 5/1920 | United Kingdom . | |
| 662298 | 12/1951 | United Kingdom . | |

*Primary Examiner*—Flemming Saether
*Attorney, Agent, or Firm*—Robert C. Kain, Jr.

[57] ABSTRACT

The locking nut and bolt system utilizes a bolt with thread having a plurality of notches generally longitudinally spaced in a predetermined pattern. Each notch has a lock face and an opposing slope. The locking unit carries one or more tines. The tine has a distal tine end adapted to latch onto the lock face of the notch on the bolt and, when the distal tine end is not disposed in one or more notches, the tine end moves on the bolt thread crest. When the distal tine end is in the notch or notches, the lock face of the notch prevents counter-rotational movement of the bolt with respect to the nut when the distal tine end abuts the lock face. The locking unit supports the tine and may be cylindrical, rectangular or on a perpendicular support face normal to a radial plane through the axial centerline of the nut thread. The locking unit may be on a nut insert or may be carried on the leg of a U, J or S-shaped clip. The locking unit may be recessed as a blind hole.

6 Claims, 41 Drawing Sheets

U.S. PATENT DOCUMENTS

| | | |
|---|---|---|
| 2,484,645 | 10/1949 | Baumle . |
| 2,521,257 | 9/1950 | Sample . |
| 2,771,113 | 11/1956 | Flora ................................................ 151/11 |
| 2,834,390 | 5/1958 | Stevens . |
| 3,176,746 | 4/1965 | Walton . |
| 3,474,846 | 10/1969 | Bien . |
| 3,517,717 | 6/1970 | Orlomoski . |
| 3,729,757 | 5/1973 | Wright . |
| 3,982,575 | 9/1976 | Ollis et al. . |
| 4,024,899 | 5/1977 | Stewart . |
| 4,168,731 | 9/1979 | Taber . |
| 4,508,477 | 4/1985 | Oehlke ................................... 411/174 |
| 4,674,931 | 6/1987 | Schwind ................................ 411/175 |
| 4,790,703 | 12/1988 | Wing . |
| 4,900,208 | 2/1990 | Kaiser et al. . |
| 5,238,342 | 8/1993 | Stencel . |
| 5,460,468 | 10/1995 | DiStacio . |
| 5,538,378 | 7/1996 | Van Der Drift . |

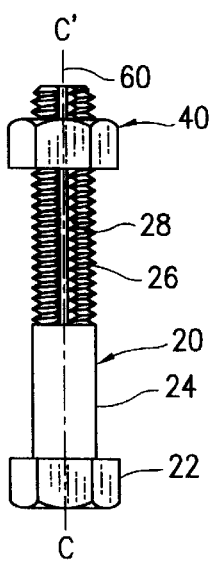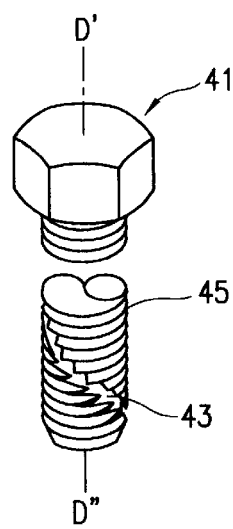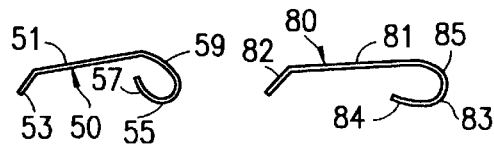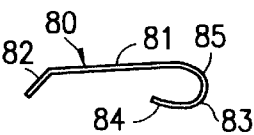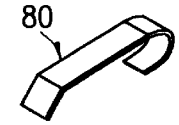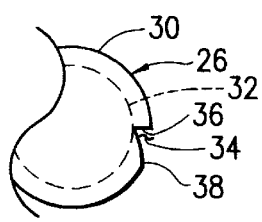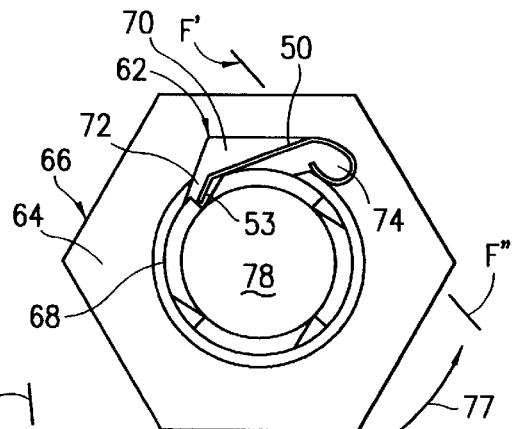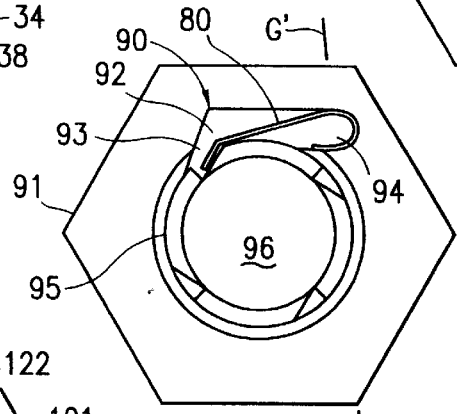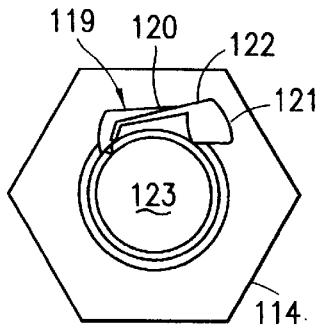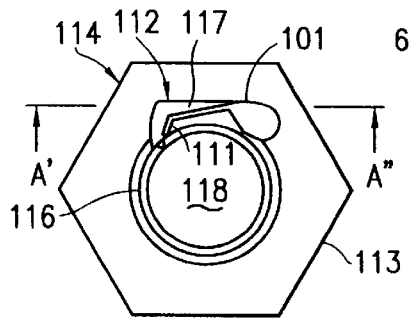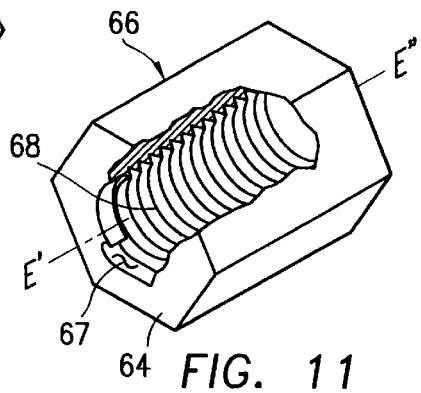

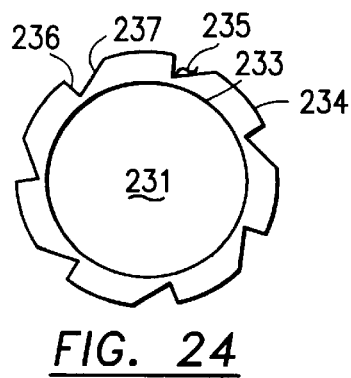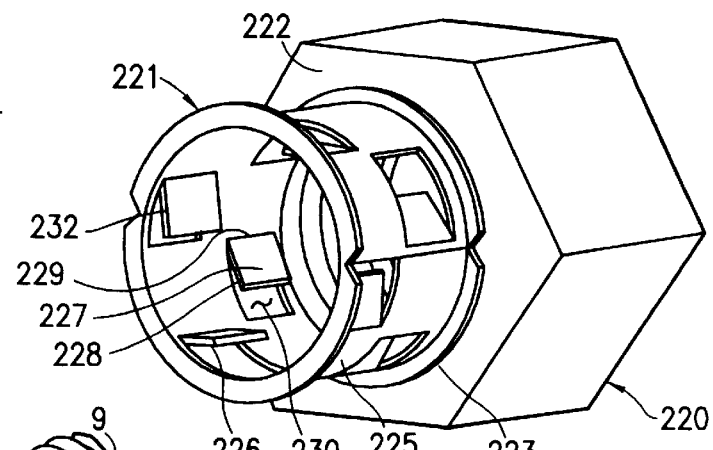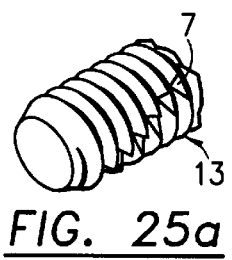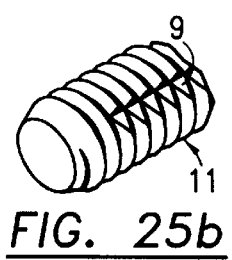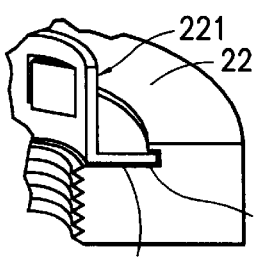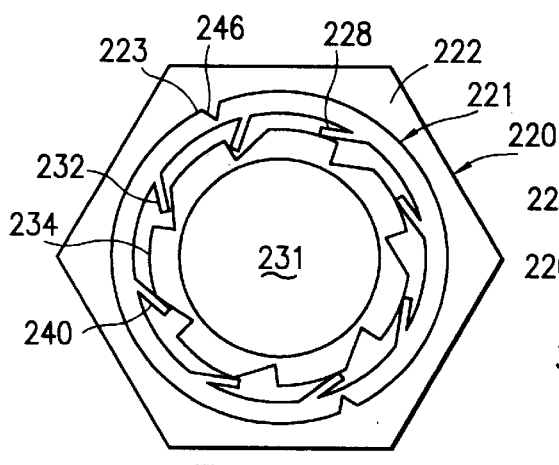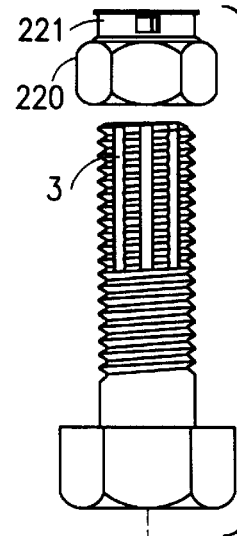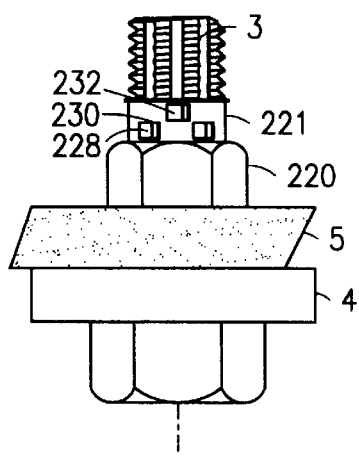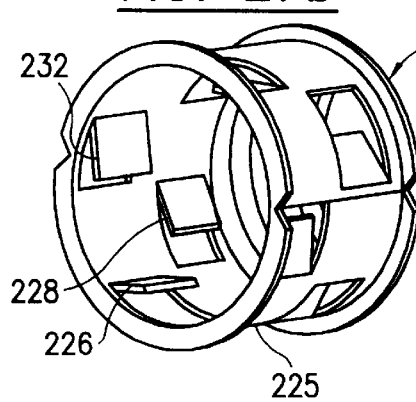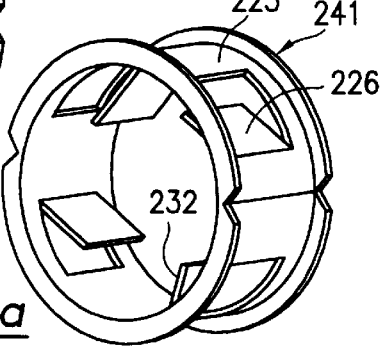

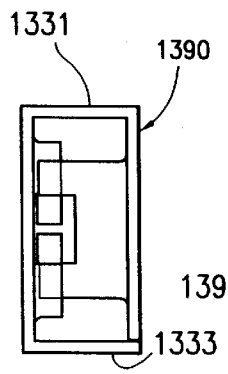
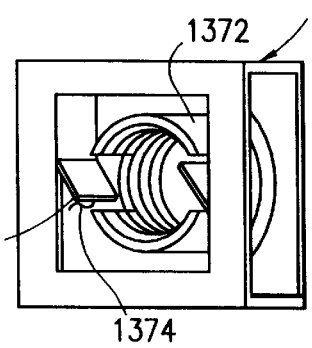
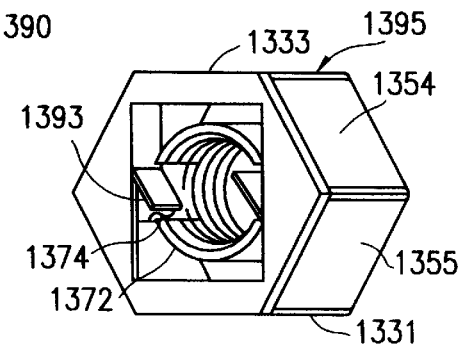
FIG. 35t    FIG. 35u    FIG. 35w
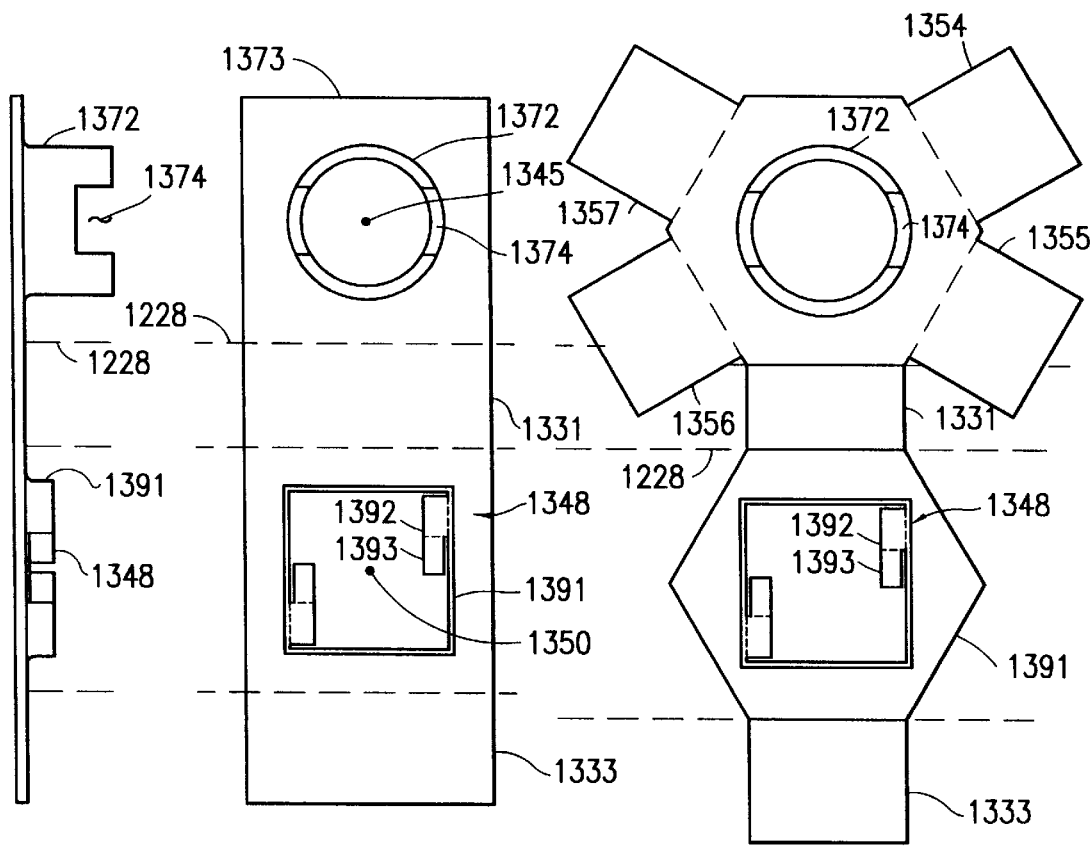
FIG. 35r    FIG. 35s    FIG. 35v

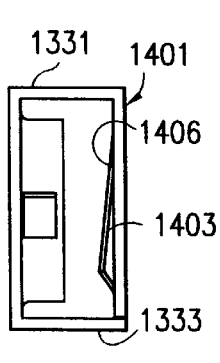
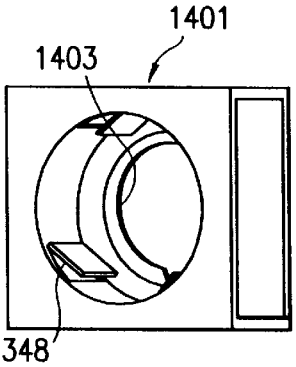
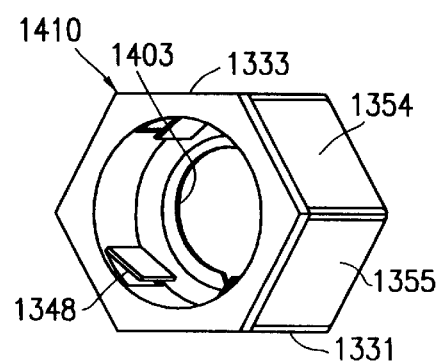
FIG. 35z  FIG. 35aa  FIG. 35cc
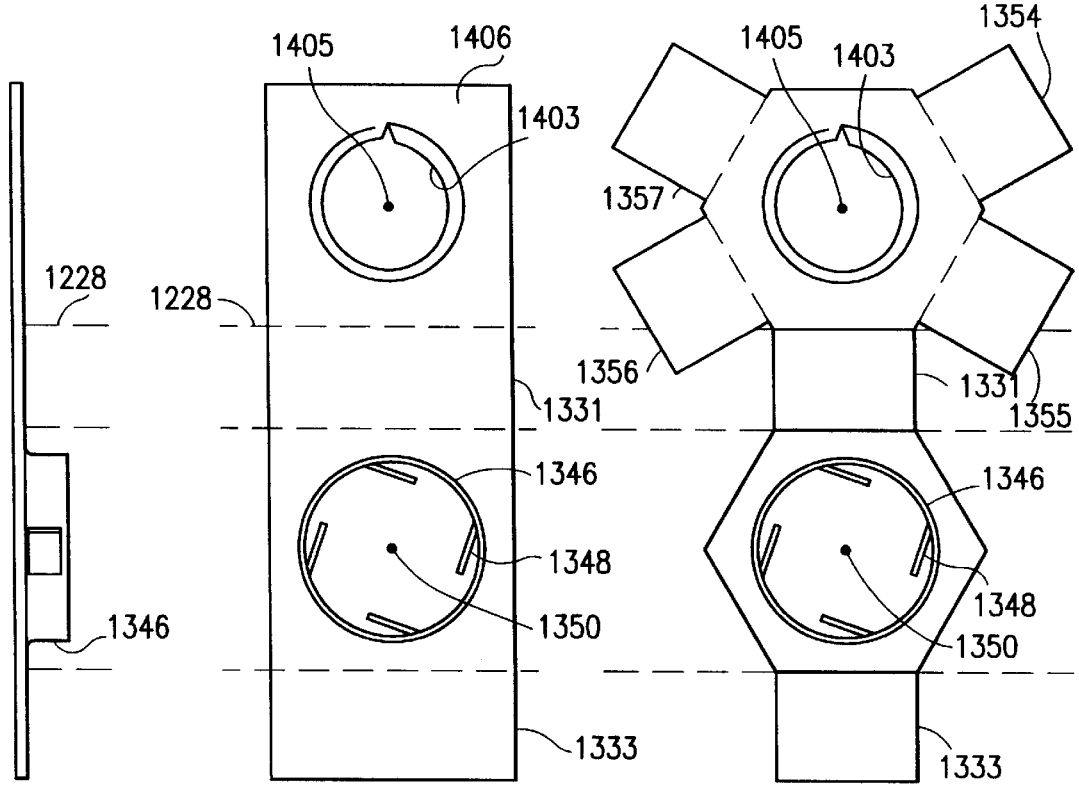
FIG. 35x  FIG. 35y  FIG. 35bb

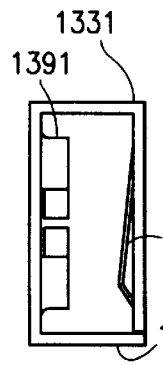 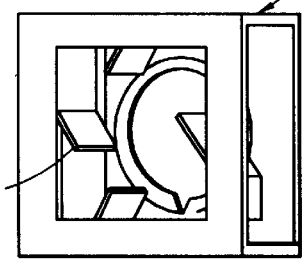 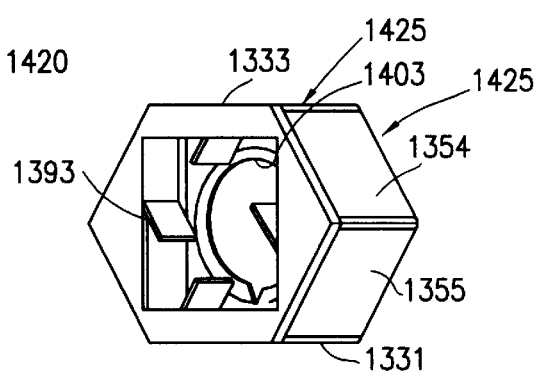
FIG. 35ff  FIG. 35gg  FIG. 35ii
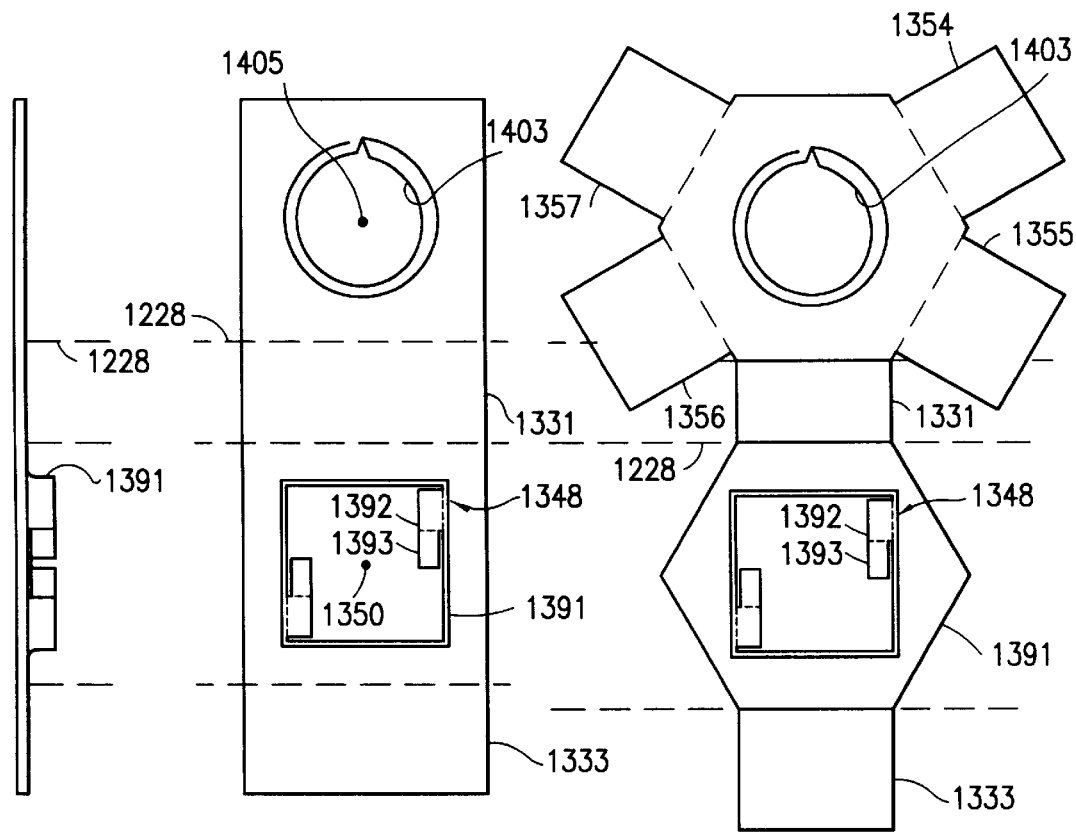
FIG. 35dd  FIG. 35ee  FIG. 35hh

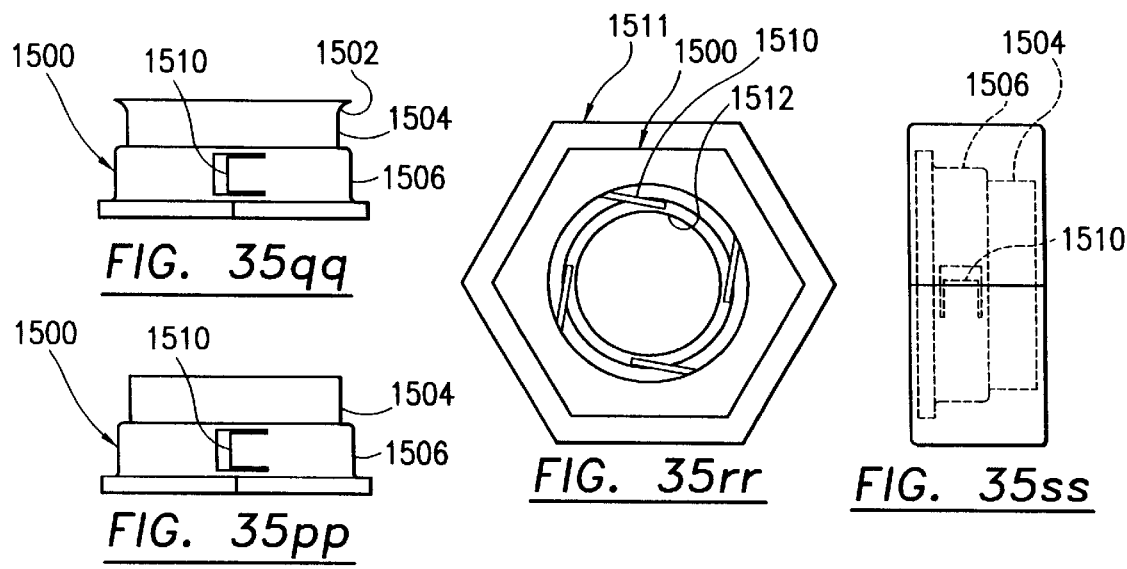

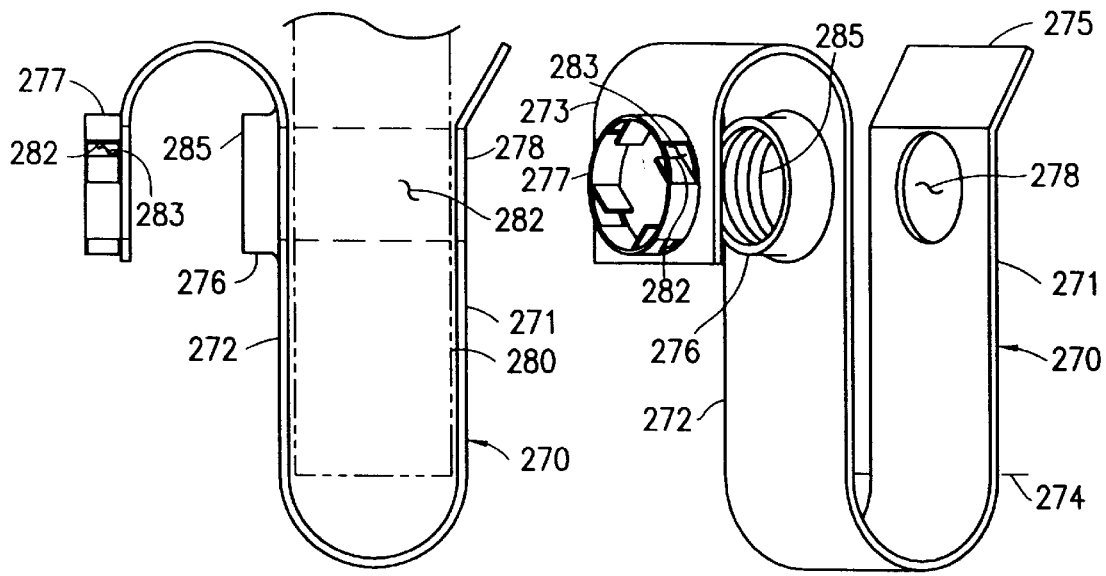
FIG. 37   FIG. 36
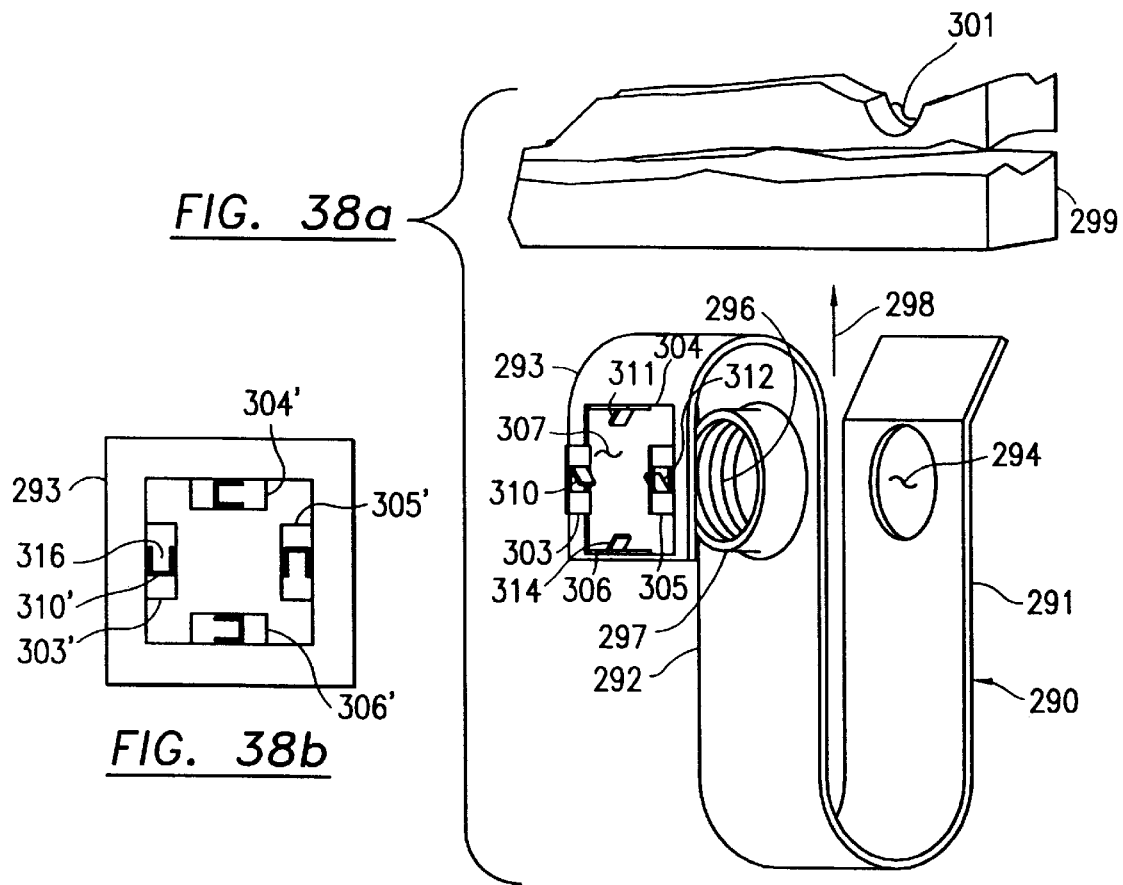
FIG. 38a
FIG. 38b

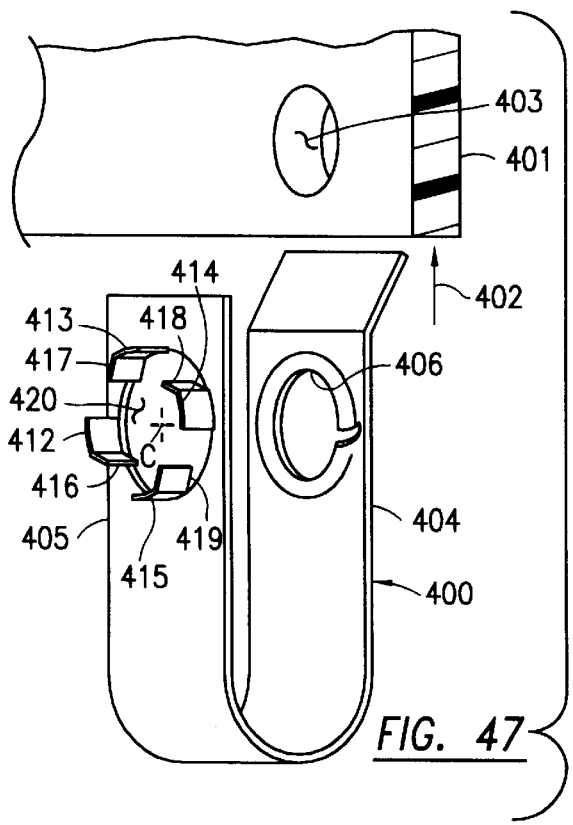
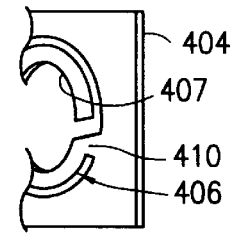
FIG. 48
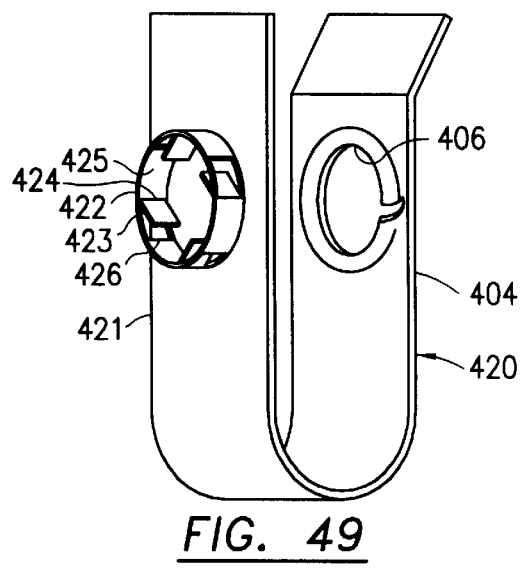
FIG. 49
FIG. 50
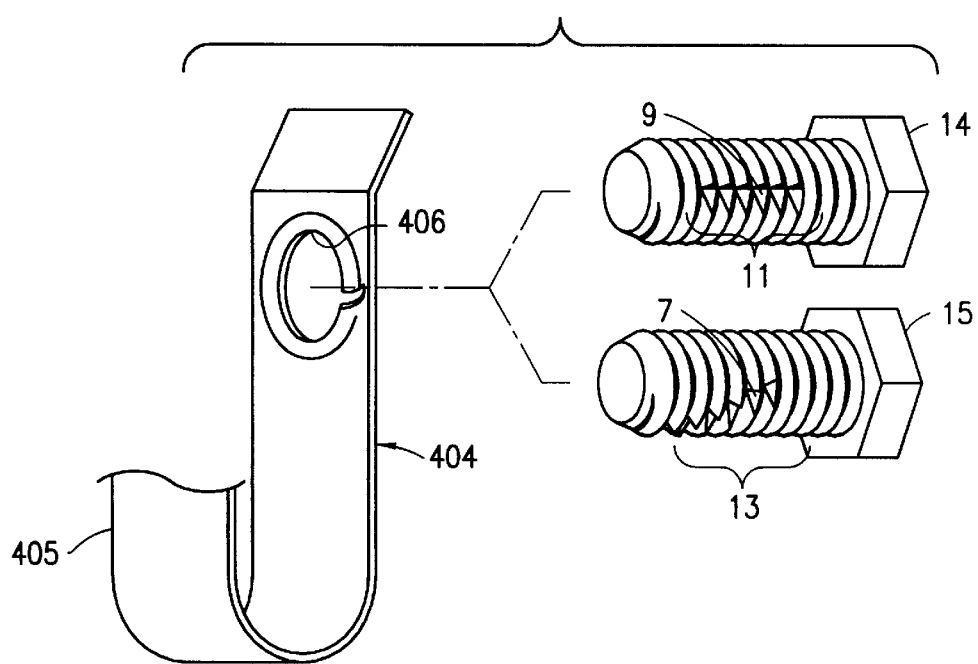

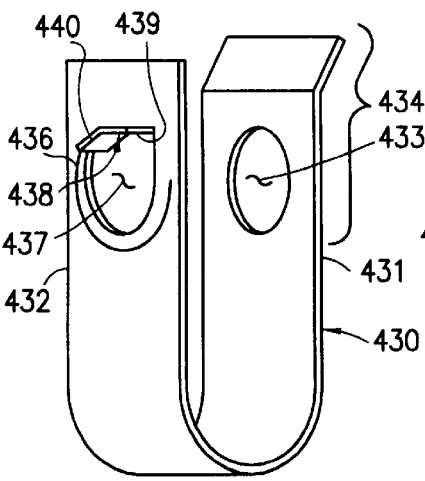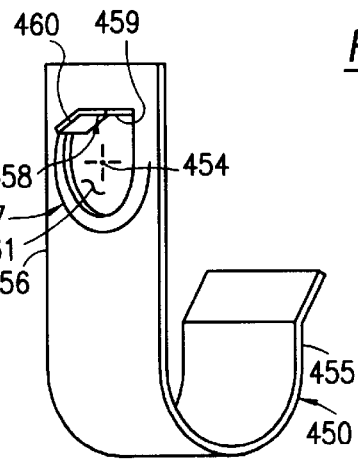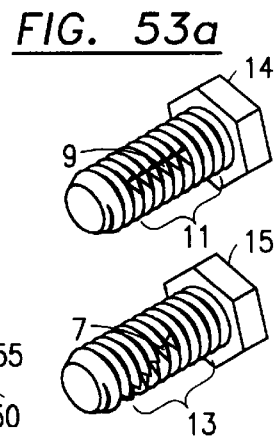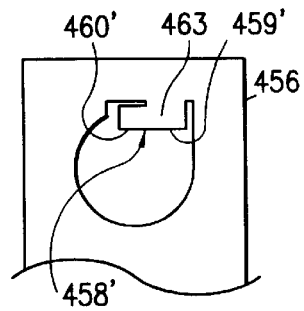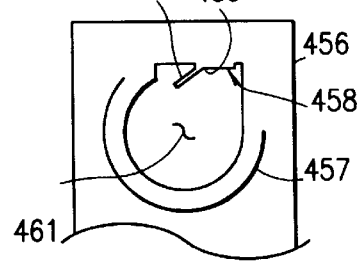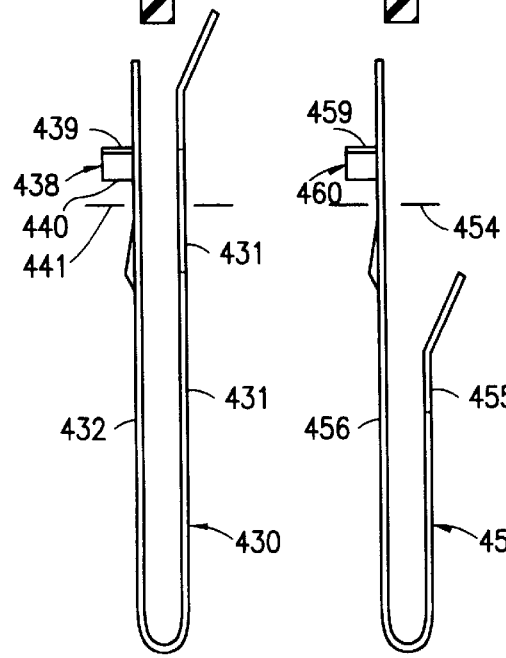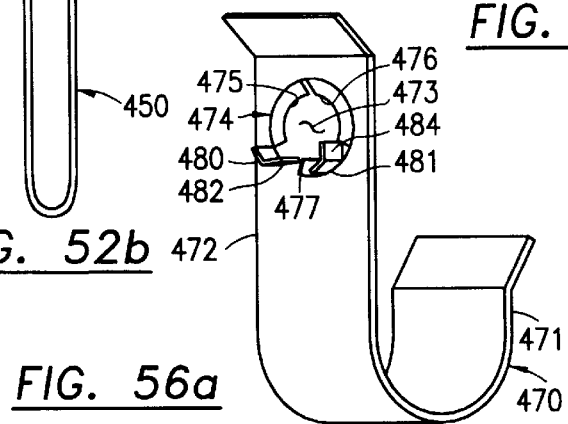

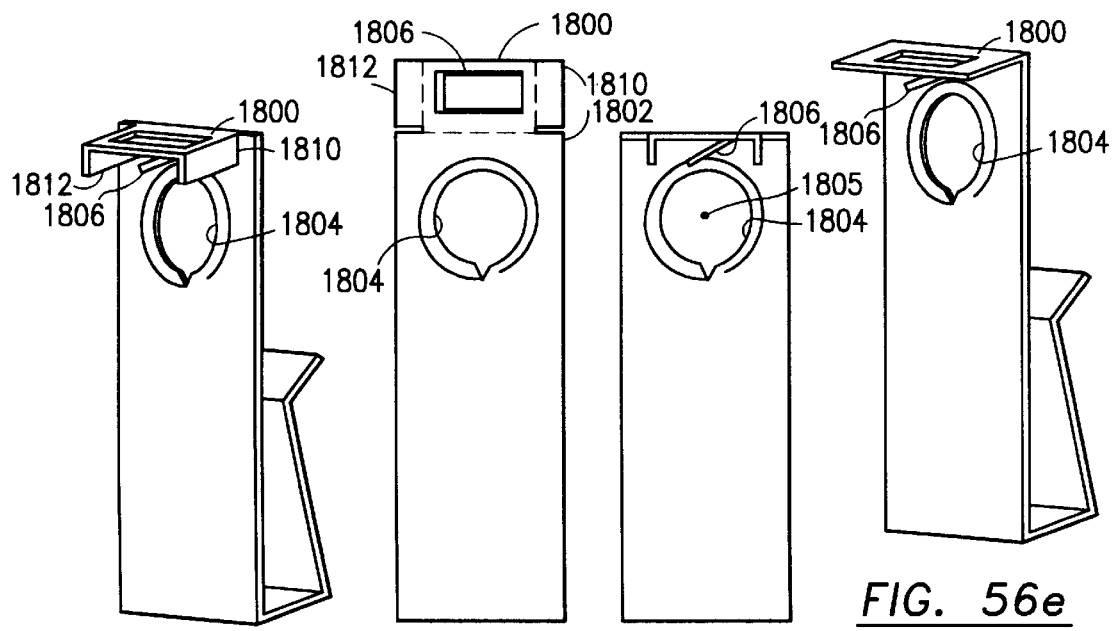
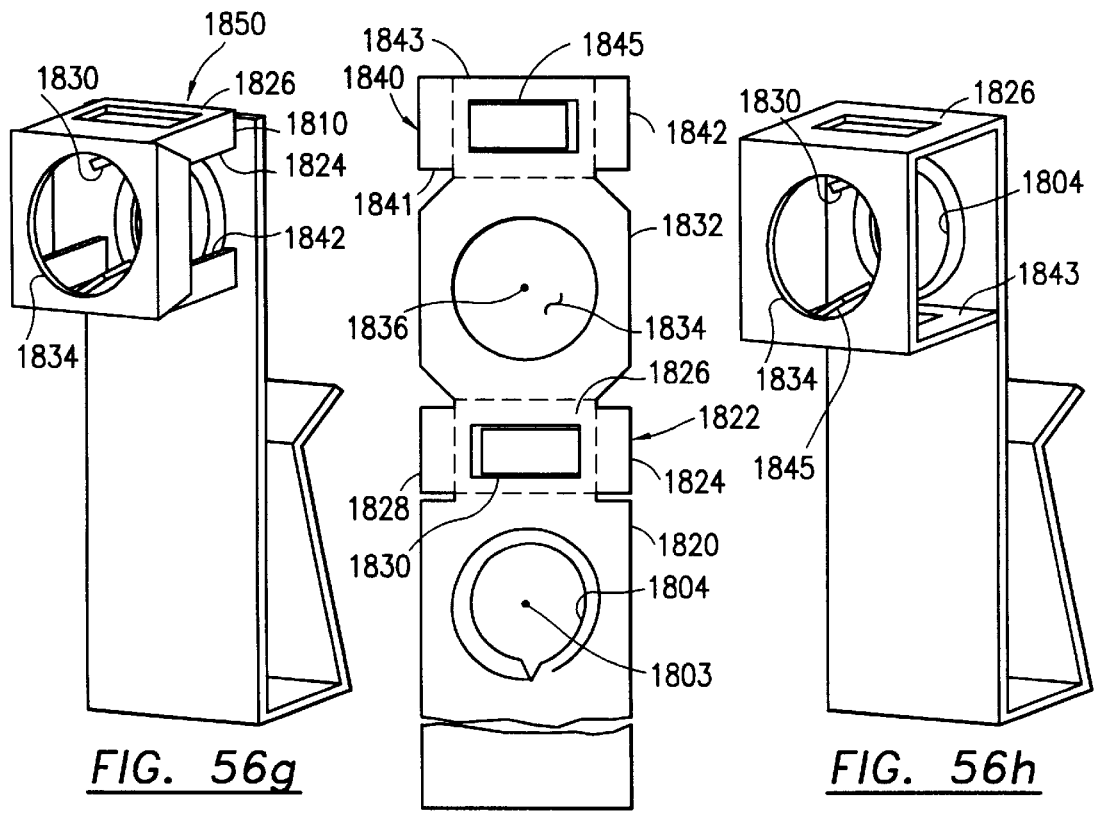

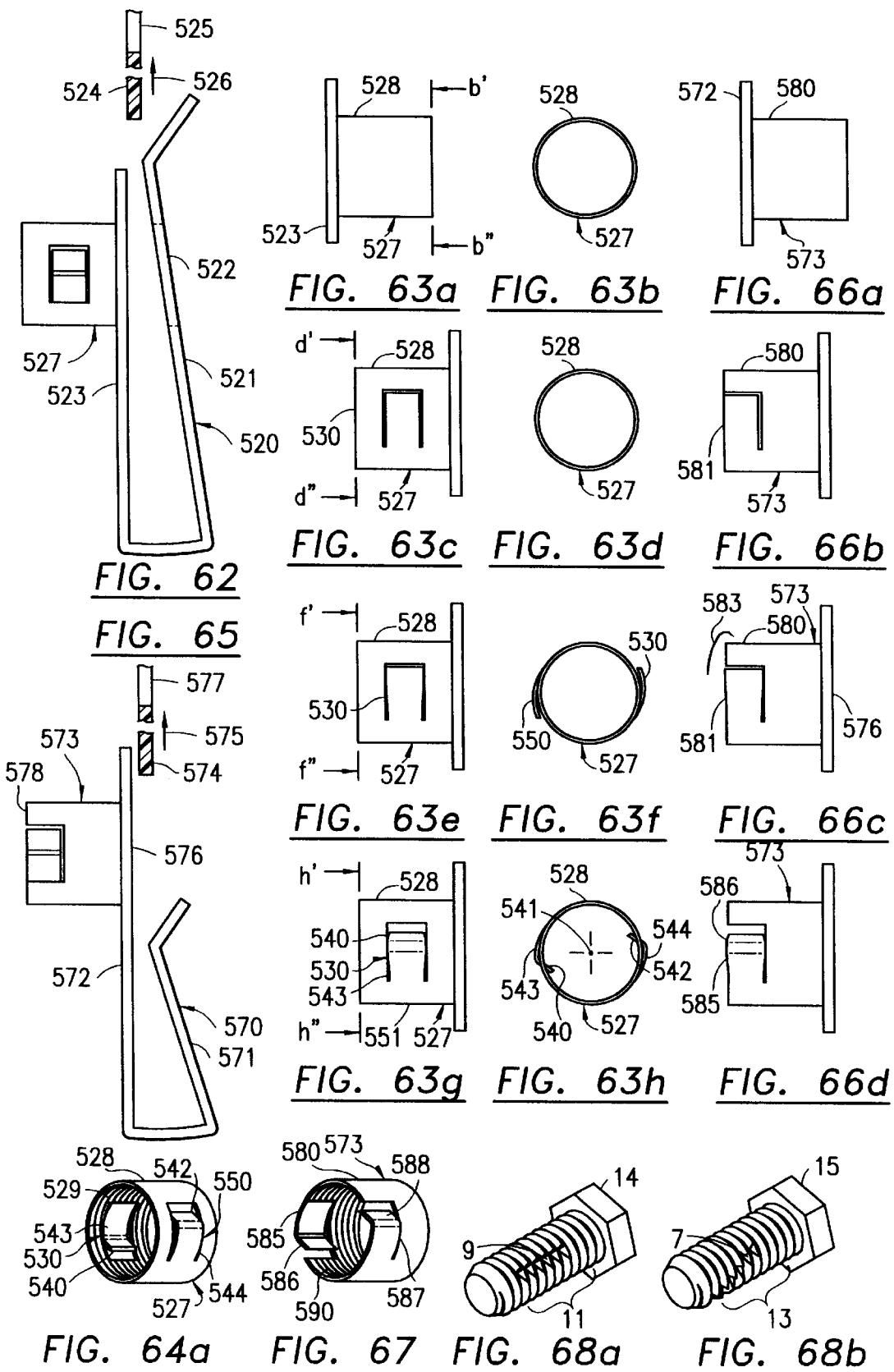

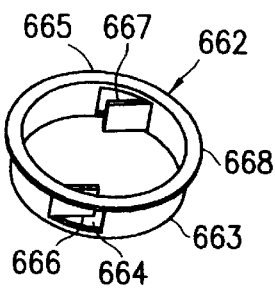
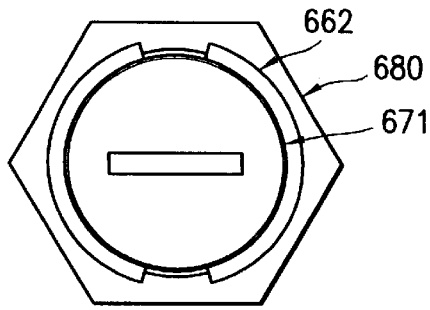
FIG. 75a
FIG. 78
FIG. 76    FIG. 77
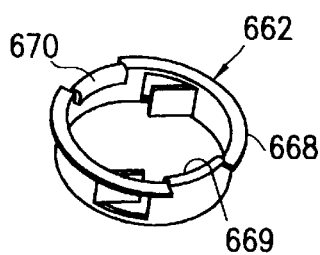
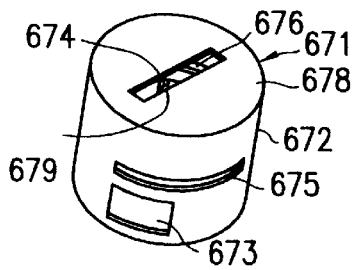
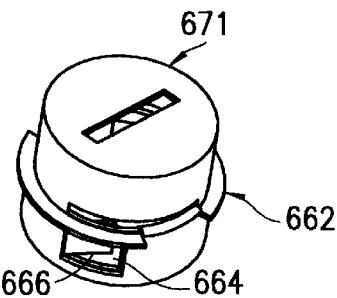
FIG. 75b
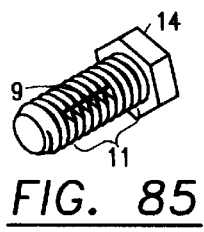
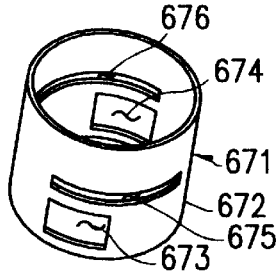
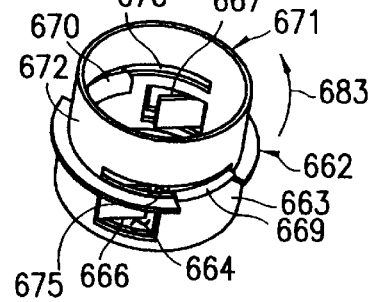
FIG. 85
FIG. 79    FIG. 80
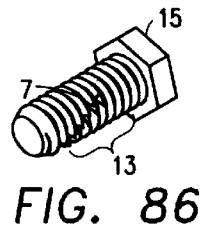
FIG. 86
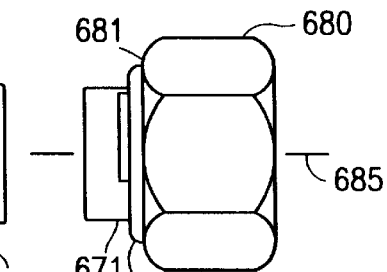
FIG. 81    FIG. 82
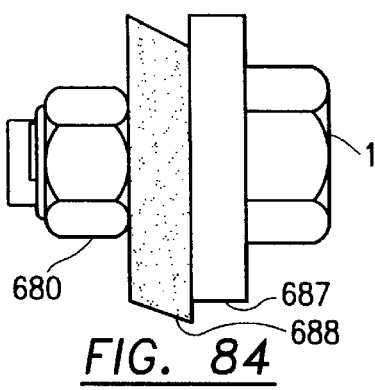
FIG. 84
FIG. 83
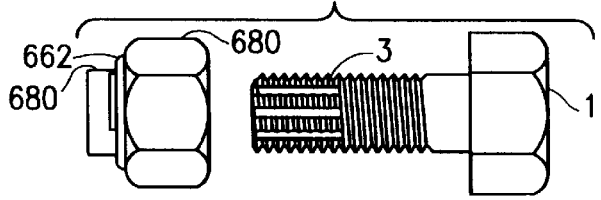

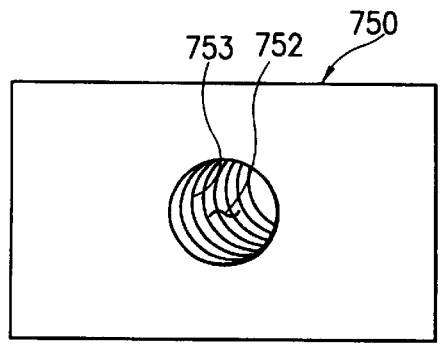
FIG. 94a
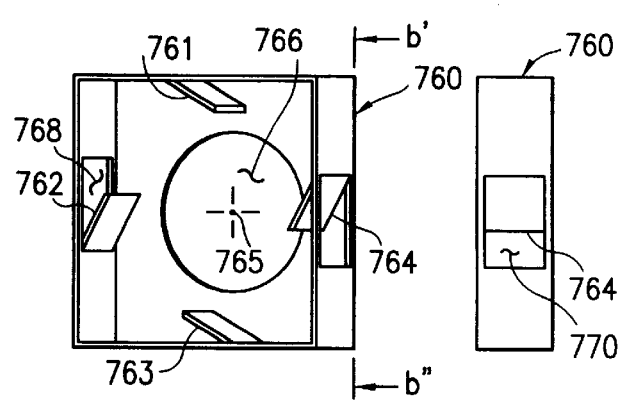
FIG. 95a  FIG. 95b
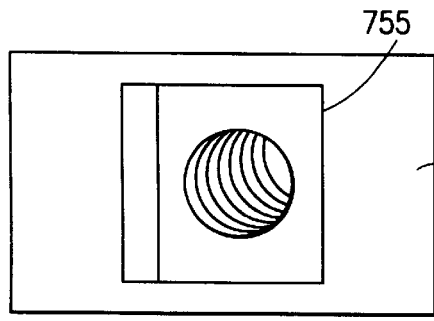
FIG. 94b
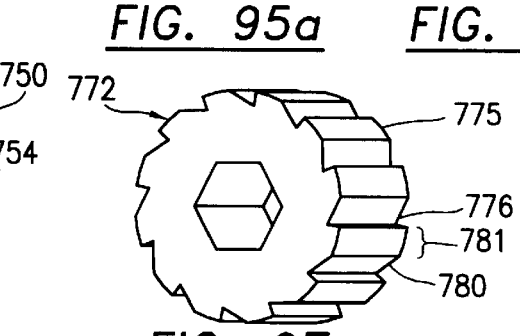
FIG. 97c
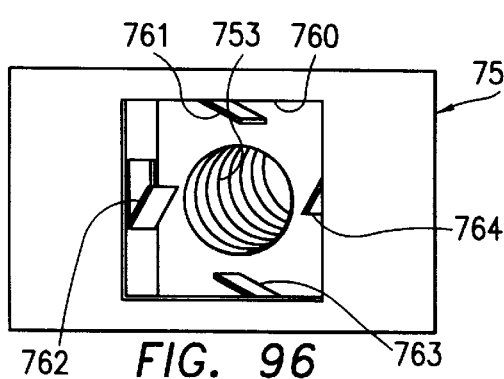
FIG. 96
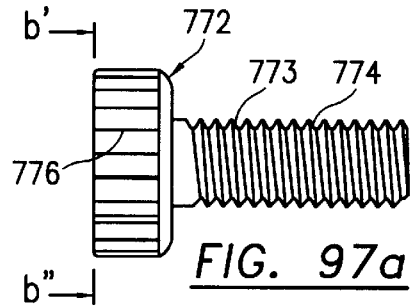
FIG. 97a
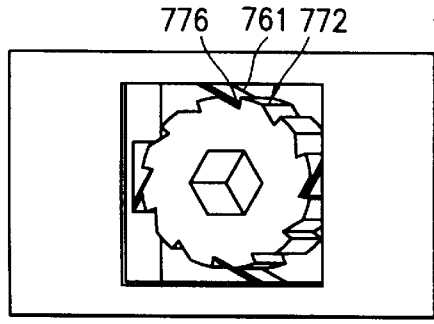
FIG. 98a
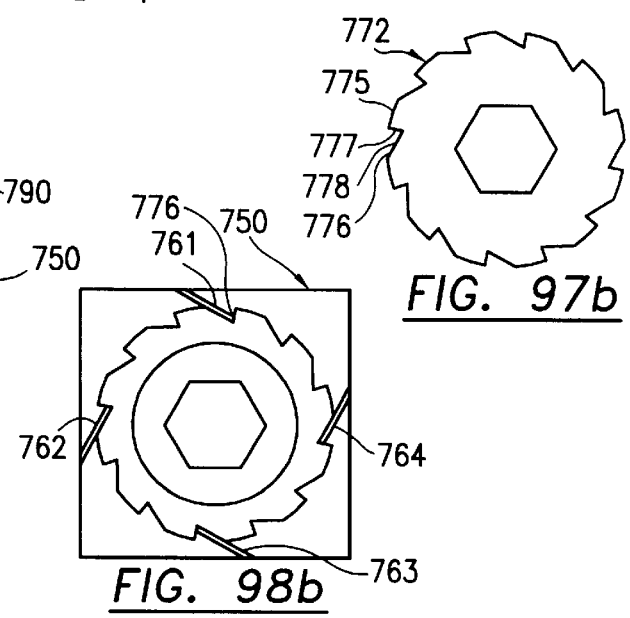
FIG. 97b
FIG. 98b

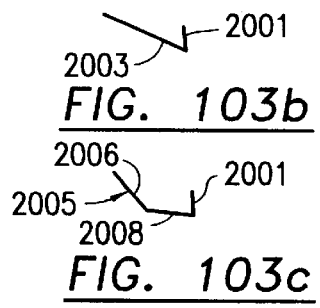
FIG. 103b
FIG. 103c
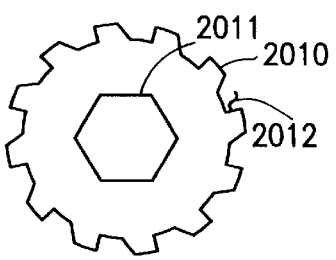
FIG. 104
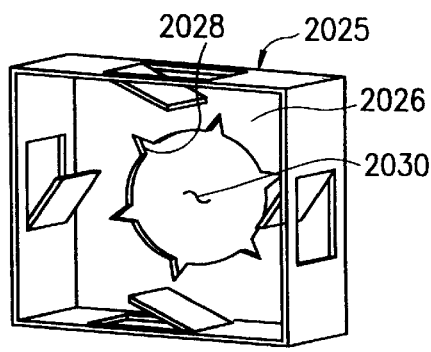
FIG. 106
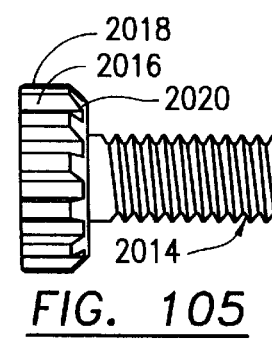
FIG. 105
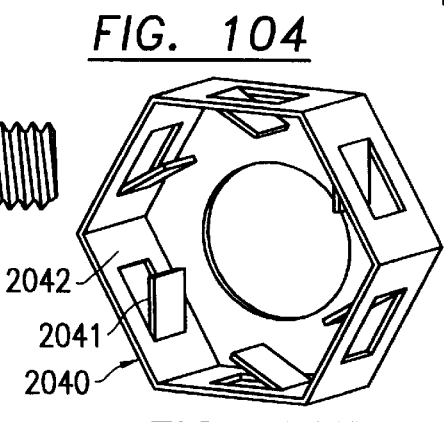
FIG. 107
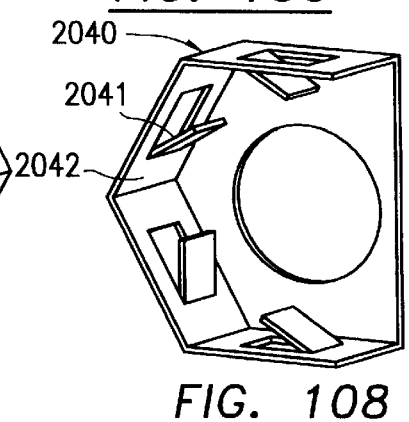
FIG. 108
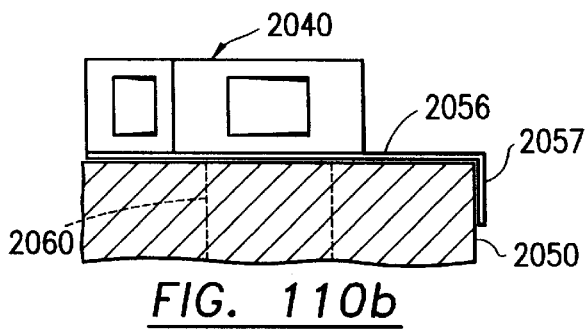
FIG. 110b
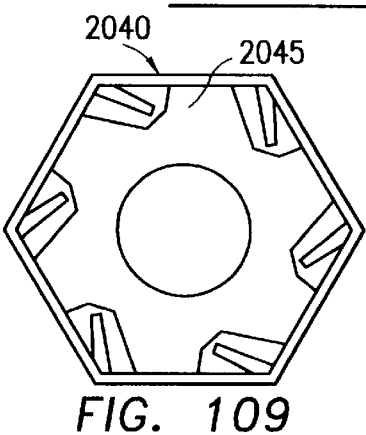
FIG. 109
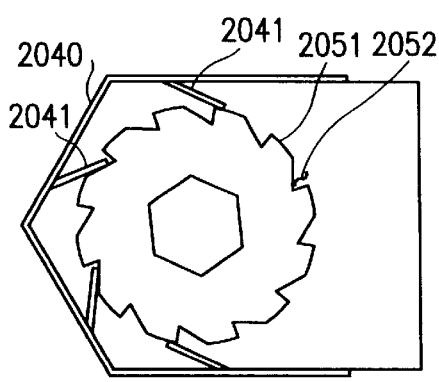
FIG. 110a
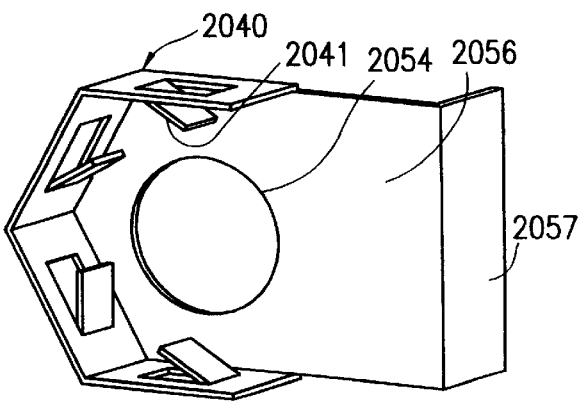
FIG. 110c

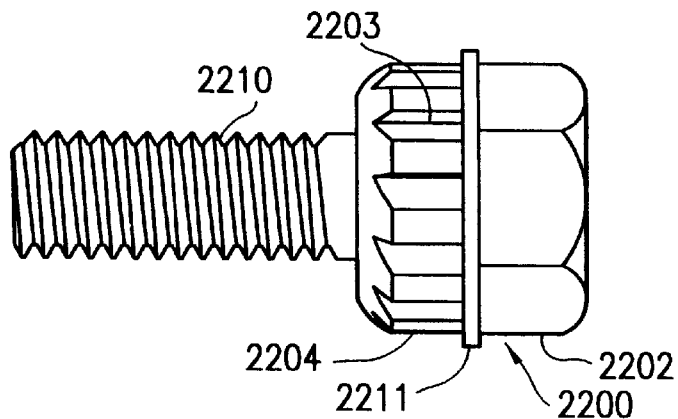
FIG. 113
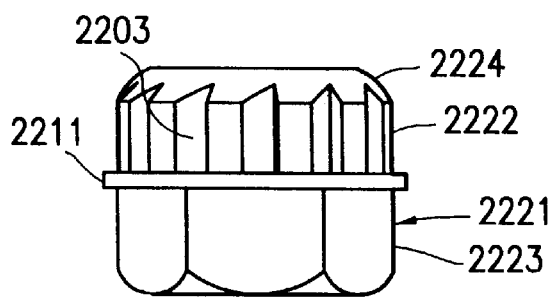
FIG. 114
FIG. 115
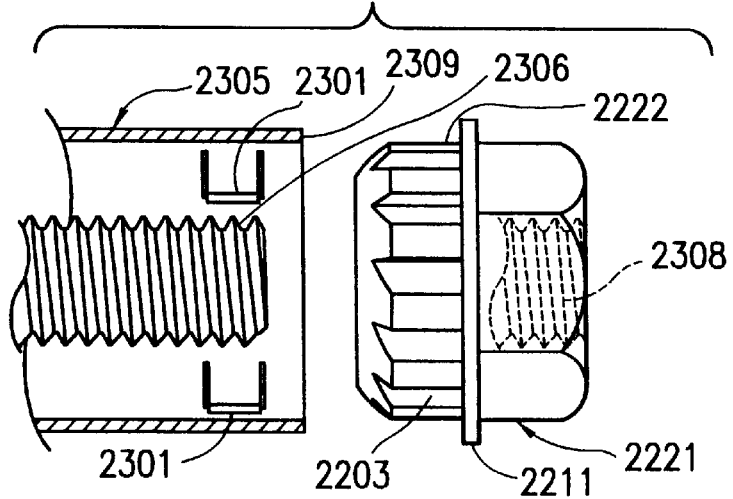

6,010,289

LOCKING NUT, BOLT AND CLIP SYSTEMS AND ASSEMBLIES

The present application is a continuation-in-part of U.S. patent application Ser. No. 08/747,323 filed Nov. 12, 1996, now pending, which claims the priority of provisional patent applications Ser. Nos. 60/015,230 and 60/015,980, respectively filed on Apr. 10, 1996 and Apr. 15, 1996, and the present application is also based upon and claims the benefit of provisional patent application Ser. No. 60/050,487, filed on Jun. 23, 1997.

BACKGROUND ART

U.S. Pat. No. 307,722 to Klemroth discloses a bolt A with longitudinal channel D running through the crest of the threads. The nut has a tine extending above a flat end surface of the nut. The tine pops into and out of channel D. U.S. Pat. No. 591,062 to Smith discloses a bolt with a longitudinal channel which enables a chisel to be placed in a slot in a nut block and further to stop rotation of the bolt with respect to the block. U.S. Pat. No. 1,088,892 to Foreman discloses a screw with a longitudinal channel extending through the threads of the bolt. The tine is located outside of the nut threads.

U.S. Pat. No. 1,136,310 to Burnett discloses small notches cut in the top of the crest of the bolt threads. The notches define radially aligned surfaces. A flexible tine in the interior of the nut moves in and out of the small notches. The tine is inserted in a tangential cavity in the nut. U.S. Pat. No. 1,211,194 to Lang discloses what appears to be a bolt with longitudinal channels on its threads. A sheet steel spring is wrapped around an exterior portion of the nut and a portion of the spring is generally radially inserted through the nut to lock into the bolt channels. U.S. Pat. No. 1,226,143 to Stubblefield et al. discloses a bolt with longitudinal channels having a somewhat radial surface and an angularly disposed surface. The nut has an annular groove or recess on one end face thereof. A semi-circular member fits within the groove. One end of the semi-circular member defines a tangentially oriented tine that pops into and out of the bolt channels.

U.S. Pat. No. 1,245,362 to Lynch discloses a bolt with a single, offset bolt thread crest which catches on a cut-out in the nut. U.S. Pat. No. 1,278,028 to Savory et al. discloses a bolt with a longitudinal channel and tines in a nut which are mounted in an internally located groove. The internal groove has a single radial dimension. U.S. Pat. No. 1,465,148 to Rosenberg discloses a bolt with a longitudinal channel through the thread crest. No nut is shown. U.S. Pat. No. 1,703,947 to Nation discloses a bolt with several longitudinal channels. A single tine is located at an interior position in the nut. The tine in the nut has a terminal end that is radially moved inward based upon the position of a locking cam. The locking cam biases the terminal end of the tine towards the notches in the bolt. The locking cam extends radially through the nut. U.S. Pat. No. 2,232,336 to Meersteiner discloses a bolt with a longitudinal channel. No nut is shown.

U.S. Pat. No. 2,301,181 to Ilsemann discloses non-load bearing or carrying faces of most of the bolt threads which are deformed and which carry locking projections. Locking projections on a plurality of bolt threads are adapted to engage nut threads and compensate for the clearances in the assembly to align and frictionally lock the nut and bolt together. The non-load carrying faces of each bolt thread include two annular series of spaced, rounded projections. The surfaces of the projections are substantially rounded. Bolt projections force the load bearing surface of the bolt against the load bearing surfaces of the nut. U.S. Pat. No. 2,484,645 to Baumle discloses a bolt with longitudinal channels. No nut is shown. U.S. Pat. No. 2,521,257 to Sample discloses a bolt with longitudinal channels. Springy tines are mounted at one end of the nut and the tines flip in and out of channels. The tines are sheared from the threads on the nut. Accordingly, there is no space radially behind the tines when the tine is fully compressed by the crest on the bolt thread.

U.S. Pat. No. 2,834,390 to Stevens discloses bolts which appear to have longitudinal channels through the threads. A plurality of radially inward pointed teeth on the nut provide locking for the combination. U.S. Pat. No. 3,176,746 to Walton discloses that each crest of each thread on the bolt has a gouged out portion. These portions, when aligned, are similar to a longitudinal channel. No nut is disclosed. U.S. Pat. No. 3,517,717 to Orlomoski discloses threads on a bolt which include two outwardly directed prongs. The prongs flex inward when the bolt is screwed onto a nut. The sliced away wedge or prongs do not have a narrow mouth and a deep throat. No nut is disclosed.

U.S. Pat. No. 3,792,757 to Wright discloses a nut with a bore having a triangular cross-sectional dimension. U.S. Pat. No. 3,982,575 to Ollis et al. discloses a thread on each bolt with a plurality of ridges forming wedge surfaces. U.S. Pat. No. 4,024,899 to Stewart discloses a top of each crest of the bolt thread having a slice and a prong protruding therefrom. The prong fits within a cut-out depression in the root of the nut thread. The cut-outs at the root of the threads do not appear to be radially aligned. U.S. Pat. No. 4,168,731 to Taber discloses a root of the nut with a cut-out and the bolt having a plurality of wedges which fit within the nut cut-out.

U.S. Pat. No. 4,790,703 to Wing discloses a nut with a bore with an imperfect, non-symmetrical cross-sectional aspect. U.S. Pat. No. 4,790,208 to Kaiser et al. discloses a bolt with a longitudinal channel through the threads.

U.S. Pat. No. 5,238,342 to Stencel discloses a bolt with a longitudinal channel into which snaps inwardly biased wings from a nut insert. The nut insert has a radially extending top flange (similar to a hat ring) and is formed as an elongated cylinder which fits within a cylindrical end bore in the nut. The wings from the insert protrude inwardly at an angle, tangentially inward towards the bolt's axial centerline. The wings are pressed inward from the elongated cylinder of the nut insert. The terminal end of the wings lock into axial or longitudinal grooves running through the bolt thread. The nut insert is keyed to a certain position on the nut by a key-tab and a complementary lockway. U.S. Pat. No. 5,460,468 to DiStasio discloses a bolt having one or more longitudinal channels through the bolt threads. The nut has one or more tines which cooperate with the channels to prevent counter-rotation of the bolt with respect to the nut. The tine or tines define a narrow mouth leading to a wider throat behind the tine such that the mouth and throat enable the tine to flex therein while the bolt threads radially move the tine back and forth during one-way rotation of the bolt with respect to the nut.

U.S. Pat. No. 1,208,210 to Purcell discloses a locking nut with tangential slot within which is disposed a spring pawl. The terminal end of the pawl interacts with a spiral groove through the bolt thread.

U.S. Pat. No. 827,289 to Bowers discloses a generally circular insert having a key end, fitted into a radial keyway in the nut, and a tine terminal end which cooperates with a longitudinal or axial groove on the bolt thread.

U.S. Pat. No. 589,599 to Hardy discloses a semi-circular nut insert with a generally radially aligned tine. The tine locks into a longitudinal groove in the bolt thread. A space is provided radially behind the tine to permit the tine to flex inboard and outboard as the tine moves into and out of the longitudinal groove on the bolt thread.

U.S. Pat. No. 5,538,378 to Van Der Drift discloses a nut insert which is flat punched to define a series of circumferential tines. The insert has a cut-out region radially behind each tine. The terminal end of each tine falls into a recess at the bottom of the root of the bolt thread. The nut insert is captured in a recess at an end face of the nut.

U.K. Pat. Publication No. 142,748 to Thibert discloses a semi-circular nut insert having a tangentially oriented locking tine. The tine moves tangentially, not radially, when the tine drops into and moves out of the longitudinal groove in the bolt thread.

U.K. Pat. Publication No. 662,298 to Simmonds a swagged nut insert.

OBJECTS OF THE INVENTION

It is an object of the present invention to provide locking nut and bolt systems with one or more compressible tines carried by nut inserts or formed on U, S and J-shaped clips.

It is another object of the present invention to provide a locking nut and bolt system with a latch mechanism which places the compressible tine into a locking position or a closed position.

It is an additional object of the present invention to provide a locking nut and bolt system wherein the bolt head carries notches thereon and the compressible tine or tines block counter-rotational movement by interacting with the notches on the bolt head.

It is another object of the present invention to provide locking nut and bolt systems which utilize bolts having a longitudinal aligned locking channel in the same plane as the bolt's axial centerline and bolts having a locking channel forming a spiral about the axial centerline.

It is an additional object to provide for removal tools for the locking nut and bolt combination.

SUMMARY OF THE INVENTION

The locking nut and bolt system utilizes a bolt with an axial centerline and a bolt thread having one or a plurality of notches generally longitudinally spaced in a predetermined pattern with proximal notches being longitudinally adjacent each other on the bolt thread. Each notch has a lock face and an opposing slope. The nut, with complementary threads, includes a recess on an end face. The recess has a central region, a recessional mouth open to the internal nut thread passage and a tangential cavity tangentially disposed with respect to the nut thread. An elongated tine has a planar tine body, a distal tine end offset from the planar tine body and proximal tine end formed as a loop. The loop has a shape complementary to the tangential cavity shape. The tine loop may be U-shaped with a respective leg exerting radially directed or tangentially directed opposing spring forces against the nut walls forming the tangential cavity or may be a solid planar element sized to fit within the tangential cavity.

In another embodiment, the recess on the end face of the nut defines a circumferential recess about the nut's axial centerline and includes a shoulder. A nut insert is placed in the recess on the shoulder. The nut insert has a planar body defined as a peripheral ring and at least one tine depends from the planar body in a substantially tangential plane with respect to the axial centerline of the bolt.

In both embodiments, the tine has a distal tine end adapted to latch onto the lock face of the notch on the bolt and, when the distal tine end is not disposed in one or more notches, the tine end moves on the bolt thread crest. When the distal tine end is in the notch or notches, the lock face of the notch prevents counter-rotational movement of the bolt with respect to the nut when the distal tine end abuts the lock face.

Preferably, the nut insert includes a plurality of tines circumferentially disposed about the planar peripheral ring of the nut insert. In a further embodiment, the nut insert includes planar support plates extending radially inward toward the axial centerline thereby creating radial free space for the radial movement of the tine beneath the planar support plates and the planar peripheral ring of the nut insert.

In a further embodiment, locking is provided by an elongated locking unit formed as a cylinder. This locking unit cylinder is mounted in the nut recess with an axially rearward ring member disposed in the circumferential nut recess. The cylindrical locking unit axially extends outbound from the nut coaxial with the axial centerline of the bolt. The cylindrical locking unit includes at least one tine, and preferably a plurality of tines, tangentially and radially extending inward toward the axial centerline. In a further embodiment, each tine is disposed adjacent a respective arcuate cut-out on the cylinder. The axial disposition of the cylindrical locking unit with respect to the nut and the cut-out permits the user to visibly identify whether the bolt is locked with respect to the nut because the user can see the disposition of the distal tine ends in and out of the notches. When the distal tine ends are in one or more notches, abutting one or more lock faces, counter-rotational movement is prevented. When the distal tine ends are riding on the bolt thread crest, the nut is not locked with respect to the bolt.

A further embodiment of the present invention utilizes a locking element captured at the end face of a nut by the disposition of a rearward ring member of locking element in the nut recess. The locking element has a plurality of axially protruding legs and each leg has a respective tine protruding tangentially and radially inward toward the axial centerline of the bolt. Each tine has a distal tine end adapted to latch onto the lock face of the notch and either ride on the bolt thread crest or prevent counter-rotational movement when the distal tine end abuts the lock face.

The one way locking features of the present invention are carried forward into U, J and S-shaped locking nut and bolt assemblies. As explained later in detail, these locking assembly clips are utilized in conjunction with bolts having an axially aligned locking channel formed by a plurality of notches or a spiral locking channel formed by a plurality of notches in a predetermined pattern about a longitudinal and axial centerline of the bolt. In one embodiment, an elongated cylindrical locking unit is formed on one of the legs of the U, J or S-shaped clip as a cylindrical locking unit. A nut is formed on the other clip leg. The cylindrical axis of the locking unit is perpendicular to the plane of the clip leg and has at least one tine, and preferably a plurality of tines, protruding tangentially and radially toward the cylindrical axis. The distal tine end of each tine is adapted to latch onto the lock face of the bolt notch or notches. The tines are disposed on the cylindrical locking unit at corresponding cut-outs. A nut is formed on another leg of the clip. When the clip is placed on a bored panel such that the axial centerline of the nut, the panel bore and the cylindrical axis of the cylindrical locking unit are substantially coaxially aligned, the notched bolt can be inserted along this common axis, and threaded onto the nut while the distal tine ends either move in one or more notches prohibiting counter-rotational movement when the distal tine end abuts the locking face of one or more notches or ride atop the bolt thread crest. The user can visually see whether the bolt has locked onto the lock clip assembly because of the tines in the cut-outs. This is particularly helpful when the bolt carries only a small segment of either longitudinally aligned or spirally disposed notches.

In another embodiment, the U, J or S-shaped locking nut and bolt assembly includes a nut formed on one of the clip legs and a locking element formed on another clip leg. The locking element has a locking element bore and a plurality of axially protruding legs perpendicular to the plane of the clip leg. Each locking element leg has a respective tine which protrudes tangentially and radially inward toward the axial centerline of the locking element bore which is coaxial with the axial centerline of the nut on the other clip leg. When the locking element bore and the nut and the bore through the panel are coaxial, and the specially configured bolt is placed through the panel bore and the nut and the locking element bore, the position of the distal tine ends are visible thereby enabling the user to determine whether locking has been achieved by the locking nut and bolt clip assembly.

In another embodiment, a U-shaped locking nut clip assembly includes a U-shaped clip member, a single thread nut having an arc less than 360° formed on one of the clip legs and a locking element having a locking element bore formed on the other clip leg. The locking element bore is coaxial with the axial centerline of the single thread nut. The locking element includes a plurality of axially protruding legs and each leg has a tine extending tangentially and radially inward toward the axial centerline. When the U-shaped clips is placed on the bored panel and the axial centerline of the nut is coaxial with the bore through the panel and the specially configured bolt is placed thereat, the position of the distal tine ends of the locking element are visible to the user enabling visible confirmation of locking action by the distal tine ends into one or more notches and abutment of the tine ends on the locking faces of the notches on the bolt.

In a further embodiment, the U-shaped locking nut assembly includes a U-shaped member, a single thread nut having an arc less than 360° formed on a first clip leg and an elongated, cylindrical locking unit formed on the other clip leg. One tine, and preferably a plurality of tines, protrude tangentially and radially inward toward the cylindrical axis which is coaxial with the axial centerline of the single thread nut. When the clip is placed in a position on the bored panel with the axial centerline of the single thread nut coaxially with the bore and the specially configured bolt placed thereat, the user can determine whether the tines have locked onto the bolt because the position of the distal tine ends are visible. Visibility is enhanced because of cut-outs in the cylindrical locking unit at each tine.

In another embodiment, the U-shaped locking nut assembly includes a U-shaped clip member, a single thread nut having an arc less than 360° formed on one clip leg, and a locking element formed on the same clip leg beyond the arc of the nut thread. The locking element has an axially protruding leg perpendicular to the plane of the clip leg. The axially protruding leg also has a tine protruding tangentially and radially inward toward the axial centerline defined by the single thread nut. When the U-shaped clip is placed on a bored panel and the axial centerline of the single thread nut is coaxial with the bore through the panel and the specially configured bolt is placed thereat, the distal tine end from the locking element prohibits counter-rotational movement when the tine end falls within the notch on the bolt and abuts the lock face. Otherwise, the bolt can be threaded on the single thread nut since the distal tine end rides atop the bolt thread crest.

In a further embodiment, a U-shaped locking nut clip assembly includes a U-shaped clip member, a nut formed on one clip leg, and an elongated locking unit formed as a cylinder on an outboard axial end of the nut. The locking unit has one tine and preferably a plurality of tines protruding tangentially and radially inward toward the axial centerline of both the nut and the cylindrical locking unit. When the U-shaped clip is placed on the bored panel and the axial centerline of the nut is coaxial with the bore through the panel and the specially configured bolt is placed thereat, the user can determine whether the bolt has locked to the U-shaped clip because the position of the distal tine ends are visible. When the distal end falls into the notches and abuts the lock faces on the bolt, counter-rotational movement is prohibited. When the distal tine ends ride atop the bolt thread crest, the bolt can be rotated with respect to the U-shaped clip.

In another embodiment, the U-shaped locking nut clip assembly includes a U-shaped clip, a nut formed as an elongated thin walled cylinder on one of the clip legs and a locking unit formed on an interior region of the nut. The locking unit includes a tine protruding tangentially and radially inward toward the axial centerline. When the U-shaped member is placed on a bored panel and the axial centerline of the nut is coaxial with the bore through the panel and the specially configured bolt is placed thereat, the locking unit on the U-shaped clip prohibits counter-rotational movement when the distal tine end falls within one or more notches and abuts respective locking faces on the specially configured bolt. Otherwise, the bolt can be rotated with respect to the U-shaped clip since the distal tine ends ride atop the bolt thread crest.

In a further embodiment, the locking nut and bolt system includes a latch closure. In this embodiment, the nut has a recess on an end face thereof and an elongated locking unit having a peripheral wall shaped complementary to the recess is disposed in the recess. A latch is moveably disposed on the peripheral wall of the locking unit. The locking unit has at least one tine, and preferably a plurality of tines, protruding tangentially and radially inward away from the peripheral wall toward the axial centerline defined by the nut thread. The latch is moveably disposed on the peripheral wall adjacent the tine and captures the tine between the latch and the peripheral wall in a closed position and, when it moves, fully exposes the tine in a locking position. In a locking position, the distal tine end falls within one or more notches on the specially configured bolt thereby preventing counter-rotational movement when the tine end abuts one or more locking faces. When the distal tine end has not fallen into one or more notches, the tine end rides atop the bolt thread crest. When the latch is in a closed position, the distal tine end is captured between the latch and the locking unit peripheral wall. In one embodiment, the locking unit has a rectangular cross-sectional shape and in another configuration, the locking unit has a circular cross-sectional shape.

In a further enhancement, the locking nut and bolt assembly with a latch can be used in conjunction with a ratchet tool when the latch is formed as a complementary cylinder to a cylindrical locking unit. In this configuration, the latch has a radially extending user actuatable control surface which enables the latch to rotate thereby placing the tines in a closed position enabling the ratchet tool to move the specially configured bolt in both a rotational and counter-rotational manner or to place the tines on the locking unit in a fully exposed position or a locking position thereby permitting the ratchet tool to move the bolt only in a single rotational direction.

In another embodiment, the locking nut and bolt system is utilized in conjunction with a bolt having a plurality of notches defined on the bolt head. A female threaded unit has a nut thread complementary to the bolt thread and also has a recess defined below an end surface of the female threaded unit. Also, the locking unit may be surface mounted on the nut. A locking unit has a peripheral wall complementary to the recess and at least one tine, and preferably a plurality of tines, protruding tangentially and radially inward toward the central axis formed by the female threads on the female threaded unit. The distal tine ends of the locking unit prohibit counter-rotational movement when the tine ends fall within the notches on the bolt head and abut the locking faces. Otherwise, the tines are disposed beyond the notches on the bolt head and permit rotational movement.

In a further embodiment, the locking nut and bolt is operable with a removal tool. The removal tool includes axially outboard and biased legs which are interposed between the proximal tine body and the bolt thread. When rotated, the interposed depending leg withdraws the distal tine end from the notches on the bolt thereby permitting removal of the locking nut from the bolt.

BRIEF DESCRIPTION OF DRAWINGS

Further objects and advantages ofthe present invention can be found in the detail description of the preferred embodiments when taken in conjunction with the accompanying drawings in which:

FIG. 1a illustrates a bolt having a longitudinal locking channel formed thereon;

FIG. 1b illustrates the notch or recess on the bolt thread;

FIG. 2a illustrates a spiral locking channel on the bolt;

FIGS. 3a and 3b illustrate a tine having an offset proximal end loop;

FIG. 4 diagrammatically illustrates the tine placed in a recess in a nut and the tine acting on the bolt threaded onto the nut;

FIGS. 5a and b illustrate a tine having a proximal end loop disposed in parallel planes with respect to the tine body;

FIG. 6a diagrammatically illustrates the tine disposed in the recess in a nut and the bolt threaded onto the nut;

FIG. 8 diagrammatically illustrates the tine disposed in the nut recess and the nut threaded on the bolt;

FIG. 10 diagrammatically illustrates another shape for the proximal end loop as a solid planar element in a recess in a nut wherein the bolt is threaded onto the nut;

FIG. 11 is a perspective view of the nut having an arcuate recess on an end face;

FIG. 23 illustrates a perspective view of a cylindrical locking unit affixed to the nut via a rearward ring member disposed in a recess on the nut end face;

FIG. 24 diagrammatically illustrates the notches on the bolt;

FIGS. 25a and 25b provide perspective views of bolts respectively having (a) a longitudinal locking channel wherein the notches fall in the same plane as the axial centerline of the bolt and (b) a spiral locking channel wherein the lock notches are longitudinally adjacent but fall in a spiral, predetermined pattern about the axial centerline of the bolt;

FIG. 26 diagrammatically illustrates the locking action provided by the tines falling into one or more notches on the bolt;

FIGS. 27a and 27b illustrate the cylindrical locking units respectively having circumferentially disposed tines and circumferentially and axially disposed tines sometimes called the "railroad design";

FIG. 28 diagrammatically illustrates a bolt having a longitudinal locking channel and a nut carrying the cylindrical locking unit;

FIG. 29 illustrates a partial, cross-sectional view of the cylindrical locking unit mounted in the recess on the end face of the nut;

FIG. 30a diagrammatically illustrates the bolt locked onto two panels with a nut and the cylindrical locking unit;

FIGS. 33tt–35xx diagrammatically illustrate pipe or bolt end locking systems;

FIGS. 36 and 37 diagrammatically illustrate an S-shaped locking nut and bolt clip assembly wherein one of the clip legs carries a cylindrical locking unit;

FIGS. 38a and 38b diagrammatically illustrate an S-shaped locking nut and bolt clip assembly wherein one of the clip legs carries a locking element having a plurality of axially protruding legs and diagrammatically shows a manufacturing stage for the locking element;

FIGS. 41a and 4b diagrammatically illustrate stages of manufacture for the locking element;

FIG. 47 diagrammatically illustrates a U-shaped clip or locking nut assembly wherein one of the clip legs carries a single thread nut and the other clip leg carries a locking element with a plurality of axially protruding legs;

FIG. 48 diagramatically illustrates a partial view of the single thread nut;

FIG. 49 diagramatically illustrates a U-shaped clip with a single thread nut on one clip leg and a cylindrical locking unit on the other clip leg;

FIG. 50 diagrammatically illustrates a U-shaped clip with a single thread nut used in connection with either the special bolt with a longitudinal locking channel or the special bolt with a spiral locking channel;

FIG. 51 diagrammatically illustrates a U-shaped locking nut clip assembly having a single thread nut and a locking element formed beyond the arc of the nut thread;

FIGS. 52a and 52b illustrate a side view of the U-shaped and J-shaped clip;

FIGS. 53a and 53b illustrate bolts having longitudinal locking channels and spiral locking channels;

FIGS. 54a and 54b diagrammatically illustrate various stages of manufacture of the clip leg carrying the single thread nut and locking element;

FIG. 55 diagrammatically illustrates a J-shaped clip having a single thread nut and a locking element formed beyond the arc of the nut thread;

FIG. 56a diagrammatically illustrates a clip having a segmented single thread nut with a plurality of locking element legs between each segment;

FIGS 56b–56h diagrammatically illustrate clip fasteners with a single nut thread on a clip leg (the clips may be U, J or S-shaped);

FIG. 62 diagrammatically illustrates a side view of a U-shaped locking nut clip assembly with a thin walled nut and a locking unit formed an interior region of the nut;

FIGS. 63a–h diagrammatically illustrate plan side views and end views ofthe nut and locking unit at various stages of manufacture (with the axial view from the perspective of corresponding section lines in FIGS. 63a, c, e and g);

FIG. 64a diagrammatically illustrates a perspective view of the thin walled nut and intermediate locking unit;

FIG. 65 illustrates a side view of a locking nut clip assembly (a truncated U-shaped clip or a J-shaped) wherein the locking unit is on an interior of the nut adjacent one axial end of the nut;

FIGS. 66a,b c and d diagrammatically illustrate various stages of manufacture of the locking unit formed on the interior of the nut at one axially end;

FIG. 67 diagrammatically illustrates a perspective view of the thin walled cylindrical nut and the locking unit on an interior portion of the nut adjacent one axial end;

FIGS. 68a and 68b illustrate a bolt having a longitudinal locking channel and a spiral locking channel, respectively;

FIGS. 75a and 75b diagrammatically illustrate a perspective view of the locking unit formed as a cylindrical locking unit before and after the formation of channel members;

FIG. 76 diagrammatically illustrates a perspective view of a latch formed as a complementary cylinder;

FIG. 77 diagrammatically illustrates a perspective view of the cylindrical locking unit with the cylindrical latch inserted therein;

FIG. 78 illustrates a top view of the cylindrical locking unit, the cylindrical latch mounted on and in a recess on the end face of a nut;

FIG. 79 diagrammatically illustrates a perspective view of a cylindrical latch (without an axial end cap);

FIG. 80 diagrammatically illustrates a perspective view of a cylindrical latch mounted into a cylindrical locking unit;

FIGS. 81 and 82 illustrate a side view of a cylindrical locking unit and a cylindrical latch and a side view of that same system mounted into a recess in an end face of a nut;

FIG. 83 illustrates a side view of the nut carrying a cylindrical locking unit and a cylindrical latch about to be threaded onto a bolt thread having a longitudinal locking channel;

FIG. 84 illustrates a side view of the locking nut and bolt assembly locking two panels together;

FIGS. 85 and 86 illustrate a bolt carrying a longitudinal locking channel and a spiral locking channel, respectively;

FIGS. 94a and 94b diagrammatically illustrate a female threaded unit in various stages of manufacture;

FIGS. 95a and 95b diagrammatically illustrates a perspective view and a side view, respectively, of a locking unit with a peripheral wall carrying a plurality of tines;

FIG. 96 diagrammatically illustrates the locking unit mounted in the recess of the female threaded unit;

FIGS. 97a, b and c illustrate a side view, an end view (from the section line b'–b") and a perspective view of the bolt having a notched bolt head;

FIGS. 98a and 98b diagrammatically illustrate a perspective view and an end view of the notched bolt head threaded into the female unit wherein the tines lock onto the notches on the bolt head;

FIGS. 100, 101 and 103 respectively diagram the user actuable control surface; the depending leg interposed between the locking body carried by the nut; and the depending leg lifting the distal tine end away from the notch on the bolt after rotation;

DETAILED DESCRIPTION OF THE PREFERRED EMBODIMENTS

The present invention relates to a locking nut and bolt and fastener system and clips forming a locking nut assembly, a locking nut and bolt system having a latch, and a removal tool for such locking systems.

Figures 2B, 2C:
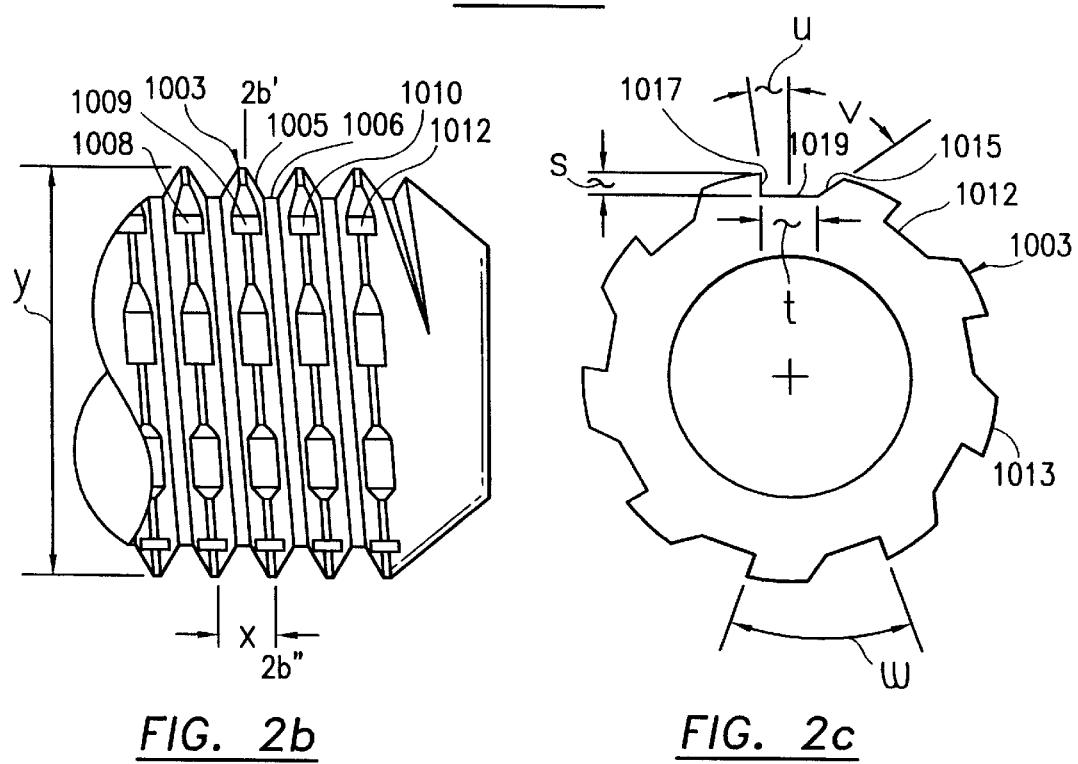
FIGS. 2b and 2c diagrammatically illustrate a partial, axial side view of a notched or grooved bolt thread and a diagrammatic cross-sectional view of the bolt over a thread line 2b'–2b", respectively.
Figures 6B, 6C:
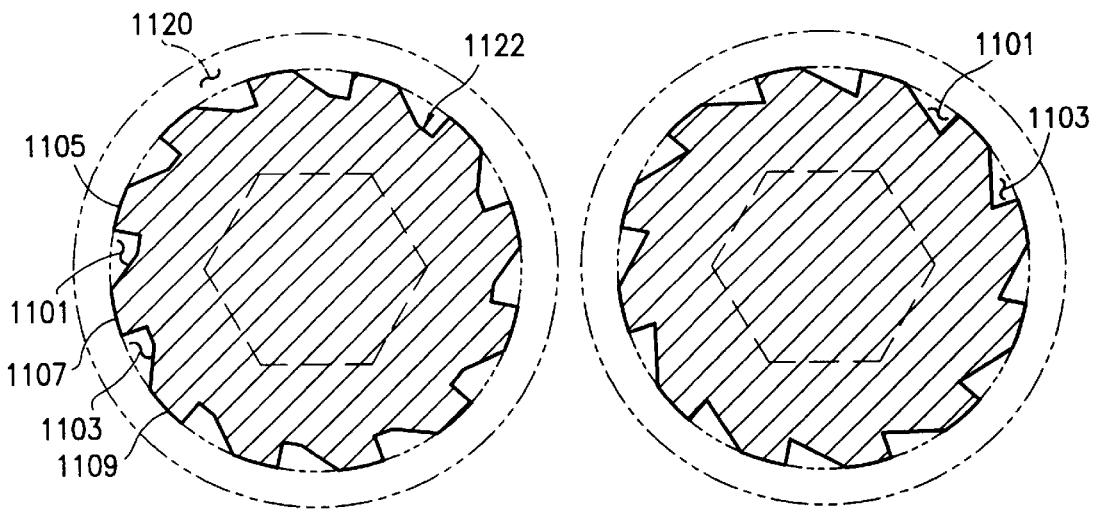
FIGS. 6b–6e illustrate bolts carrying notches or bolt heads carrying lock face notches (for blind hole applications) and FIGS. 6f and 6g illustrate locking protrusions.

FIG. 1a illustrates bolt 20 having a longitudinal locking channel 28 through bolt threads 26. Bolt threads 26 are formed on bolt stem 24. Bolt 20 includes bolt head 22. Bolt 20 includes an axial centerline C–C' numerically identified as centerline 60 in the figure. A nut 40 has been threaded onto bolt thread 26. It should be noted that the longitudinal locking channel 28 may extend the entire length of bolt thread 26 or may occupy a segment or a portion of thread 26. As described later, nut 40 has some type of locking mechanism disposed thereon or therein which generally includes a compressible tine which moves into the notch formed on each bolt thread and out of the notch and rides atop the crest of the bolt thread. As used herein, the term "compressible" refers to a tine that moves generally radially into a locking notch or groove. FIG. 1b diagrammatically illustrates a partial view of the bolt. Bolt thread 26 includes bolt thread crest 30 and a trough 32. Notch 34 may be deeper than trough 32 or may be a shallow notch on crest 30. The longitudinal channel 28 in FIG. 1a is formed by a plurality of notches shown in FIG. 1b as notch 34. Notch 34 includes a locking face 36 and an opposing slope 38. Other notch designs are illustrated in FIG. 2c and 6b. When the distal tine end falls into notch 34, locking action occurs prohibiting counter-rotational movement when the tine end abuts lock face 36. When the distal tine end is circumferentially beyond notch 34, the tine end rides atop bolt thread crest 30. Dependent upon the axial dimension of the distal tine end and the axial distance between circumferentially aligned segments of bolt thread crest 30, the distal tine end may interact with a single notch or may interact with a plurality of notches.

FIG. 1a illustrates a bolt having a longitudinal locking channel formed as a predetermined pattern with proximal notches being longitudinally adjacent each other. FIG. 2a illustrates bolt 41 having a spiral locking channel 43. Spiral locking channel 43 is formed of a plurality of notches, similar to notch 34 in FIG. 1b, however these notches when placed adjacent longitudinally each other form a spiral 43 about the axial centerline D'-D" in FIG. 2a. The spiral locking channel 43 also consists of a plurality of notches generally longitudinally formed on the bolt thread 45 in a predetermined spiral pattern with proximal notches being longitudinally adjacent each other on the bolt thread. In other words, each notch on adjacent circumferential segments of the bolt thread 45 are generally longitudinally adjacent. However, a group of notches form a spiral pattern about the bolt. This notch pattern accommodates the axial dimension of the compressible distal tine end. However, when a plurality of notches is defined on bolt thread 45, the plurality of notches forms a predetermined spiral pattern about axial centerline D'-D". Bolt heads 22, 41 may be hexagonal and may include a recess for an allen wrench or slots for screwdrivers. Further details of the specially configured bolts and other features of the operation of the locking nut and bolt assembly can be found in U.S. Pat. No. 5,460,468 to DiStasio which is incorporated herein by reference thereto. Also, additional details of the locking nut and bolt assembly, the compressible tine and features of the specially configured bolts and the locking nut and bolt assembly consisting of clips can be found in U.S. patent application Ser. No. 08/747,323, filed Nov. 12, 1996, by Robert DiStasio and the contents of that patent application are incorporated herein by reference thereto.

FIG. 2b diagrammatically illustrates a partial, axial side view of bolt 1003 having bolt thread 1005, root 1006 and a plurality of notches or cut-outs 1008, 1009, 1010, 1012 forming an axial channel or groove. FIG. 2c illustrates a diagrammatic cross-section of bolt 1003 along the crest of bolt thread 1005. Bolt 1003 is designed to operate as a locking ratchet. The teeth 1013 (beyond cut-out or notch 1012) are equally spaced apart. The following table provides exemplary dimensions.

| Bolt Thread Groove Table | | |
|---|---|---|
| Outside diameter | y | 0.385" |
| Thread gap | x | 0.059" |
| Ratchet tooth arc | w | 40 degrees |
| Descending slope 1015 angle | v | 55 degrees |
| maximum lock face 1017 angle | u | 10 degrees |
| base 1019 | t | 0.050 |
| lock face 1017 height | s | 0.020 |

Bolt 1003 may be used with the fastening nuts, clips and fasteners rather that bolts 20, 41.

FIGS. 3a, 3b and 4 illustrate an elongated tine and a nut and bolt system. These figures will be discussed concurrently herein. FIGS. 3a and 3b show elongated tine 50 having a generally planar tine body 51, a distal tine end 53 angularly disposed at an offset position with respect to planar body 51 and a proximal tine end loop 55 opposite distal tine end 53. Proximal end loop 55 is angularly offset with respect to planar body 51. Proximal end loop 55 is generally U-shaped and has legs 57, 59.

Elongated tine 50 is placed in recess 62 formed on end face 64 of nut 66 as shown in FIG. 4.

FIG. 11 shows a generic example of nut 66 having a recess 67 on end face 64. Arcuate recess 67 generally shows the shape of recess 62 in nut 66 in FIG. 4. However, nut 66 in FIG. 11 provides a perspective, broken away, partial view of nut 66, nut thread 68 and the central axis E'-E" for nut 66.

Returning to FIG. 4, recess 62 includes a central arcuate region 70 and a recessional mouth 72 open to the internal passageway about the central axis of nut 66. Recess 62 also includes a tangential cavity 74 which is tangentially disposed with respect to the nut thread 68. In FIG. 4, the tangential aspect of tangential cavity 74 is identified by section line F'-F". Proximal tine end loop 55 is disposed in tangential cavity 76 such that the U-shaped legs 57, 59 exert radially directed, opposing spring force against the nut walls forming the tangential cavity. These radially directed forces, one of which is radially directed toward the axial centerline of the nut and the bolt and the other of which is radially directed away from that coaxial centerline, lock tine 50 into recess 62. Distal end 53 of tine 50 moves radially inward and outward dependent upon whether tine end 53 falls in one of the notches or rides atop the bolt thread crest. Recess 62 is large enough and central region 70 is large enough such that distal tine 53 moves radially into central region 70 when the tine end rides on the bolt thread crest. This is the spacial flex zone of this locking system. As an example of the distal tine end moving in the radial space of central region 70, see FIGS. 8 and 10.

When distal tine end 53 abuts the lock face of the notch, counter-rotational movement is prohibited. This occurs when the tine is in the locking zone. Rotational movement shown by arrow 77 is permitted since distal tine end 53 rides the opposing slope 38 of the notch 34 (see FIG. 1b) and moves onto the bolt thread crest 30 based upon the relative position of the bolt and nut 66. Bolt 78 is shown as including four circumferentially disposed locking channels. However, the bolt may include only a single locking channel as shown in connection with bolt 20 in FIG. 1a.

The radially directed tine locking forces affecting the nut walls adjacent U-shaped legs 57, 59 effectively lock tine 50 into recess 62. Tangential cavity 74 is tangentially disposed with respect to central region 70 in that it is slightly radially beyond the nut thread crest and nut trough. See FIG. 11.

FIGS. 5a, 5b and 6 are discussed concurrently herein. FIG. 5a shows an elongated tine 80 having a planar body 81, a distal tine end 82 offset at an angle with respect to planar tine body 81 and a proximal tine end loop 83. End loop 83 consists of a U-shaped body having legs 84, 85. Legs 84, 85 lie either in the same plane as planar body 81 or in a plane parallel to planar body 81.

Tine 80 is placed in recess 90 formed in nut 91. Recess 90 has a central region 92, a recessional mouth 93, and a tangential cavity 94. The recessional mouth is open to the axial centerline of the nut. Tangential cavity 94 is generally in the same plane as central region 92. Legs 84, 85 exert opposing spring forces against the nut walls formed by tangential cavity 94. These forces are generally tangentially disposed with respect to nut thread 95 and the axial centerline of bolt 96.

Recess 90 establishes a radial free space radially behind tine 80 (the spacial flex zone) and particularly planar body 81. This enables tine 80 to move into and out of the radial free space dependent upon the position of distal tine end 82. When distal tine end 82 is disposed in one or more notches on bolt 96 (shown in FIG. 6a), the radial free space is large. When the distal tine end 82 rides atop the bolt crest (see generally FIGS. 8, 10), the radial free space behind tine body 81 and tine 80 is reduced. The parallel plane configuration of legs 84, 85 is illustrated in FIG. 6a. The forces exerted against the nut wall by legs 84, 85 are generally tangentially oriented in plane G'–G".

Sometimes, reference will be made to certain terms explained below.

A "locking zone" is the area where a locking mechanism, such as a tine, engages a locking face, on a bolt or pipe thread, to prevent counter-rotation. In a general sense, the space making up the zone extends from one or more locking faces on the bolt thread (or the bolt head in the so-called "blind hole" locking design shown in FIGS. 97*a*, and 103*b* et al. or the blind hole nut in FIGS. 114–115), and projects out to a perimeter of the bolt or locked item. For example, in a threaded bolt manufactured with a groove or a slot, the locking zone is the volumetric space missing from a comparable threaded bolt without a groove or slot. See FIG. 6*b*. Of course, multiple grooves or slots may be formed in the bolt thread. In another embodiment, such as a protrusion on a polygonal shaped object, the locking zone extends from the outer most point of the protrusion and surrounds and mimics the perimeter of the polygon in a space determined by the height of the protrusion. In a strictly mechanical sense, the locking zone is defined as the difference between the greatest radial distance at the outer edge of the protrusion and the radially inner distance at the base of the protrusion. See FIG. 6*g*. Since the protrusion describes a circle when rotated about an axial centerline, any locking mechanism or tine in the peripheral band or locking zone will engage the protrusion and hence lock the rotating bolt or pipe against the stationary nut or fastener.

Also, the lockable bolt or pipe or bolt head or nut may carry a cut-out, groove or slot. The locking zone in this embodiment is the radial difference between the radially outermost portion of the slot and the root or radially innermost portion of the slot, groove or cut-out. If a tine or locking element falls into the locking zone and engages the locking face, counter-rotational movement is prohibited.

Any body can contain one or more locking zones

A "spacial flex zone" is a spacial area around the locking mechanism, (for example, a tine), once the locking device or mechanism is fully outside of the locking zone. The spacial flex zone allows the locking mechanism (i.e., tine) to operate, flex naturally and retract from the locking zone without permanent deformation.

The "spacial flex zone" whether in clips, nuts or blind hole clips or blind hole bolts: (a) allows tines to flex naturally with a sufficient long straight tine or variations with bent tines; (b) prevents the tine from taking a set; (c) allows variations of engagement angle; (d) allows grooves to be above, or below, the minor of the bolt; and (e) reduces resistance during installation by an end-user who may not need a wrench to spin the nut on the bolt.

The spacial flex zone allows a variety of different shaped tines to accomplish (a) secure engagement during locking; and (b) flexing during inbound installation; and (c) flexing during outbound removal.

The tine design and the spacial flex zone prevents the tine from bouncing out of the locking zone and malfunctioning following installation. For example, in one embodiment the spacial flex zone is a radial space or cavity between the bolt and the tine housing.

Sometimes, the term "angle of engagement" is utilized herein. In preferred embodiments, tines intersect the engagement face in a locking zone at an angle less than 90 degrees to prevent the tine from popping out under stress. See FIG. 6*h*. Keeping the tine from popping out is important. The deeper the tine drops into the slot or locking zone and abuts the locking engagement face, the easier it is to achieve a high quality angle of engagement.

Although a short tine can achieve an adequate angle of engagement, it generally will not flex correctly. A steep angle of engagement also exerts excessive forces on the tine, even deforming the tine should it exceed the yield point, as it flexes in and out of the grooves.

There are certain benefits of a longer tine. A longer tine will generally result in less wear and tear on the bolt and tine when applying the nut to a bolt. See FIG. 64*b*. A tine of sufficient length that has attained an acceptable angle of engagement will keep the tine under its "yield strength" and avoid permanent deformation when turning the nut onto a bolt. A short explanation of yield strength is set forth below.

The longer the tine, the smaller the radial angle of flex of the tine. This lowers the chance of the tine being permanently deformed which could result in either losing the angle of engagement or losing its designed form as it is installed. If the tine loses its "spring" it ceases to function correctly.

The tine can overcome this tendency to permanently deform and/or incorrectly function if there is a sufficient spacial flex zone in the locking system. For example, there should be an adequate spacial flex zone between the outer radial diameter of the bolt and the point where the tine is attached to its base mechanism. This attachment is sometimes referred to herein as the proximal end portion or region of the tine. The portion of the tine that engages the locking face in the locking zone is the distal end or terminal end of the tine.

In other embodiments, the distal end of the tine is juxtaposed or near the circumference of the outer diameter of the male thread. To function without distorting the tine, the spring tine must be bent away from the bolt thread when outside the locking zone and radially moved into the spacial flex zone. A second bend at the distal end of the tine moves the tine back from the bolt at an angle of engagement. See FIG. 14. This permits the tine to be lengthened and, depending on the composition and thickness of the tine, will increase the tine's flexibility and effectiveness.

The issue of yield strength of the tine is important. Without the proper spacial flex zone, deformation of the tine can occur during retraction. For example, if the tine is forced into a concave shape or any other position that results in jamming or distortion of the tine body, it will not function correctly.

General comments regarding certain aspects of the present invention follow.

The stamped fasteners (e.g. FIGS. 35*f*–35*oo*) may be considered a unique sub-group within the locking nut and bolt system.

When referring to a "locking position or closed position", the term "engaged" may better explain the system.

The invention described herein is not limited to "fasteners" but is also relevant to threaded pipe or rod and all other objects that require locking attachments where counter-rotation is undesirable.

General comments regarding bolt and nut combinatory systems follow.

A variety of designs for tines and engagement walls attain a predetermined "angle of engagement".

The system allows an end-user to visually view or inspect the locking mechanism, confirming the locking engagement.

The nut in the system is nearly "free spinning" during assembly. This can only be accomplished by designing the tines to reduce resistance (friction) during one-way rotation.

The tines should be as long as possible and the spacial flex zone around the bolt should be large enough for the longer tine to correctly flex.

An important object of the invention is to establish the correct geometry to attain consistent engagements of tines in grooves at minimal and consistent degrees between engagements based on a mathematical formula. Odd number of tines off-set against an even number of grooves or an even number of tines off-set against and odd number of grooves.

The formula follows: 360 divided by (the number of equally spaced tines) times (the number of equally spaced grooves)=degrees between engagements. Example: 360/8× 9=5 degrees represents 8 tines and 9 grooves or slots.

This mathematical relationship represents a vast improvement over haphazard spacing of tines, i.e., over 100, 120, 160 degrees.

The invention allows the locking system to be re-tightened or re-torqued when necessary.

Once the system is engaged it can be easily disengaged. This is provided by the removal tool and the latch. See FIGS. 99 and 89 and 95*a*.

In many embodiments of the invention, redundant locking features can be provided with simultaneous engagement of tines in locking zones to reduce the locking dependence on single tines and to disperse the locking stresses over multiple tines when necessary within extreme vibrational environments.

In many embodiments, the stamped tine can be installed on the nut without a keyway or orientation with respect to the nut other than the stamped tine and locking nut insert being upside down.

In many embodiments, in order to prevent rotation of the locking mechanism, ridges or striations are formed on the nut end face. The end nut face is the planar, radially aligned, circumferential wall on which the "brim" sits. A cutout on the brim of the top hat nut insert (FIGS. 30*b*–30*e*) allows the swaged wall of the nut to fill the cutout during swaging.

In several embodiments, the V-shaped cutouts in the "brims" of the top hat design or the railroad design are not designed to key the clip or insert to a certain orientation on the nut since circumferential orientation of the locking insert is not necessary. This reduces assembly costs.

In several embodiments of the invention, incorrect installation of the nut by the end user is prevented because the nut can not be inadvertently put on backwards. Because there are no threads easily accessible from the locking tine side, the nut can only be threaded inbound from one side.

The invention has a minimum number of parts for ease of assembly. This makes the system easily manufacturable with a minimum number of secondary processes.

In order to help the end user save time during installation of the nut and bolt system, the present invention does not use cotter pins that require either expensive tools or manual instructions and bending. The present system is simply threaded together. In many embodiments, the user is able to install the locking system with ordinary tools, such as a wrench or nutrunner.

In several embodiments, the invention applies more accurate clamp loads to the locking system since the nut and bolt are more "free spinning" than prevailing torque nuts. Prevailing torque nuts require more torque to install the nut on the bolt which results in additional wear and tear on installation tools and guns and adds to worker fatigue during installation of the fastener systems.

General comments regarding fasteners, clips, formed nuts and nuts follow.

The clip and the tine are manufactured with varying thickness and are adapted to form a positive lock if the distal tine is altered to mate properly with grooves in a screw and the tines are long enough to allow proper flexing.

The distal tines can be beveled to permit an angle of engagement and/or a mating of tine "shape" with screw grooves to assure mechanical locking.

The radial spring arms of the tines in certain clip designs are protected from being accidentally crushed in shipment or during installation using protective structures. See, e.g., FIGS. 46*c*, 56*h*.

In certain clip and tine designs, a locking clip or tine is integrated into an extension of a threaded extruded barrel which has been extruded to a wider diameter to accommodate a spacial flex zone that is not threaded. FIGS. 46*h*–46*j*. This double extrusion design serves to save material costs and space.

A locking clip is integrated into a lanced threaded extruded barrel that permits increased clamp load due to an increase number of threads which surround the locking mechanism.

Locking bolt and screw systems have the following general features.

The bolt has an engagement face, within a groove perpendicular or helical to the threads, that engages a locking tine mechanism at an angle, which prevents counter-rotation of the bolt or screw.

The "angle of engagement" between the tine or locking device and the engagement wall should be less than 90 degrees to prevent the tine from disengaging from the bolt notch.

The rising face of the notch, opposite the engagement face, in the three face groove design, is an innovation to increase the load carrying thread surface, allowing for increased torque tension strength within the locking zone of the fastener. FIGS. 2*c*, 6*k*, 6*n*, 6*q*.

Figures 6F, 6G:
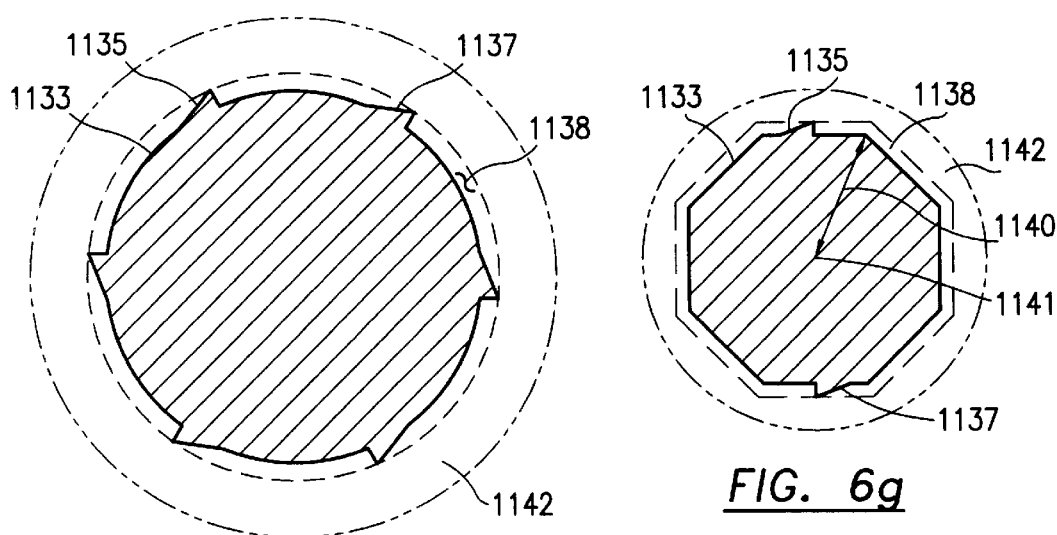

A three-faced pattern for grooves is utilized to permit better "angle of engagement" for the tines. FIGS. 6*k*, 6*n* and 6*q*.

The three-faced pattern for grooves allows either a thicker tine to engage on the engaging wall or a variety of distal tine designs, in a variety of materials to seat properly on the engagement wall.

The bolt having a concave engagement wall (FIG. 60) deflects the tine into the core of the groove and thereby decreases the angle of engagement at the upper portion of the engagement wall.

The bolt having an "overhung" engagement (FIG. 61) wall deflects the tine into the core of the groove and thereby decreases the angle of engagement along the engagement wall.

Screw and bolt designs permit the screws or bolts to be rolled with roll dies requiring no secondary processes to make engagement grooves.

The screw or bolt designs have grooves in the bolt or screw limited to a zone on the bolt or screw such that the clampload of the fastener is contained on the full threads of the bolt and the locking device can fully engage in the grooves.

All clips that have a tine on the locking mechanism engage in a locking zone in a groove above minor.

The "V" cuts in the blind hole clip allow proper seating in a beveled blind hole or a funnel shaped blind hole. FIG. 106.

Four (4) tines or four (4) engagement locking devices can be manufactured with an economy of material by cutting metal prior to folding in a pattern that offsets the tines.

FIGS. 6b–6g graphically illustrate the locking zone and spacial flex zone for certain locking bolts and locking bolt heads. Locking bolt heads are used in connection with the blind hole design (see FIG. 9b). With respect to FIG. 6b, a plurality of locking zones 1101, 1103 are created intermediate protrusions 1105, 1107 and 1109. Of course, locking zones 1101 and 1103 are sometimes referred to as grooves or slots herein. The spacial flex zone 1120 is the area around locking zones 1101, 1103 and graphically identifies the peripheral area in which the distal end of the locking tine travels when that portion of the locking tine has not fallen into locking zones 1101, 1103. As described later, solid body 1122 may be the core or stem of the bolt or may be a bolt head.

With respect to FIG. 6c, locking zones 1101, 1103 have a different shape (a triangular shape) as compared with locking zones 1101, 1003 in FIG. 6b. In FIG. 6b, the locking zones are generally four-sided. One side is open to the outermost peripheral dimension of the body.

Figures 6D, 6E:
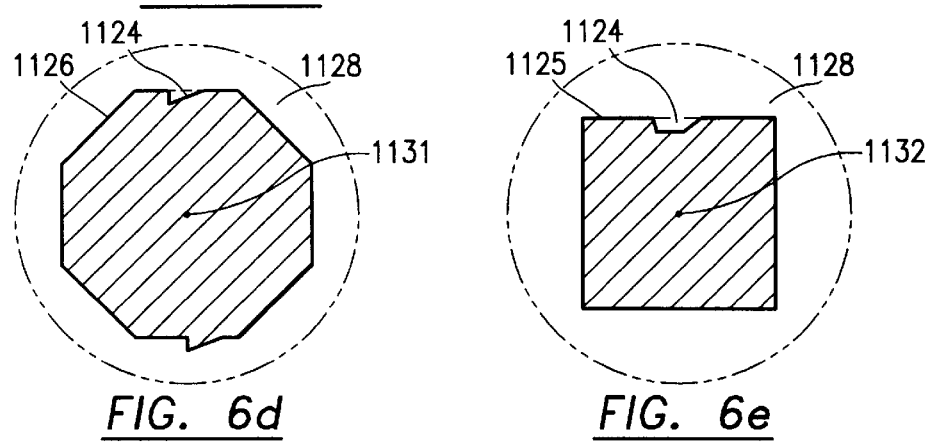

FIG. 6d graphically illustrates locking zone 1124 formed within a polygonal shape body 1126. Spacial flex zone 1128 represents the area in which the distal end of the tine moves when that end has not fallen into locking zone 1124. In a strict mechanical sense, assuming body 1126 rotates about central axis 1131, the locking zone describes a circular band defined by the outer radial dimension of locking zone 1124 and the radially inward dimension of that zone.

In a like manner, FIG. 6e includes locking zone 1124 and a square body 1125. Square body 1125 rotates about axially center line 1132 and the polygonal cut-out shape describes a similar circumferential locking zone band and a spacial flex zone 1128. The tine, when outside the polygonal cut-out, moves in the spacial flex zone.

FIGS. 6f and 6g show bodies 1133 having protruding elements 1135, 1137 which establish the outer boundary of locking zone 1138. With respect to FIG. 6g, the mechanically accurate locking zone is a peripheral ring or band established by the radially outermost dimension of protrusions 1135, 1137 and dimension 1140 which represents the largest radial dimension of the body other than protrusion 1135, 1137. Body 1133 rotates about axially center line 1141. Spacial flex zone 1142 is graphically illustrated in FIG. 6f and 6g. It should be noted that the locking zone and spacial flex zones shown in FIGS. 6b–6g are only illustrative of these zones and the actual dimensions of the zones are normally smaller dependent upon the mechanical operation of the tine and the depth of the groove or the height of the protrusion from the respective rotating body.

Figure 6H:
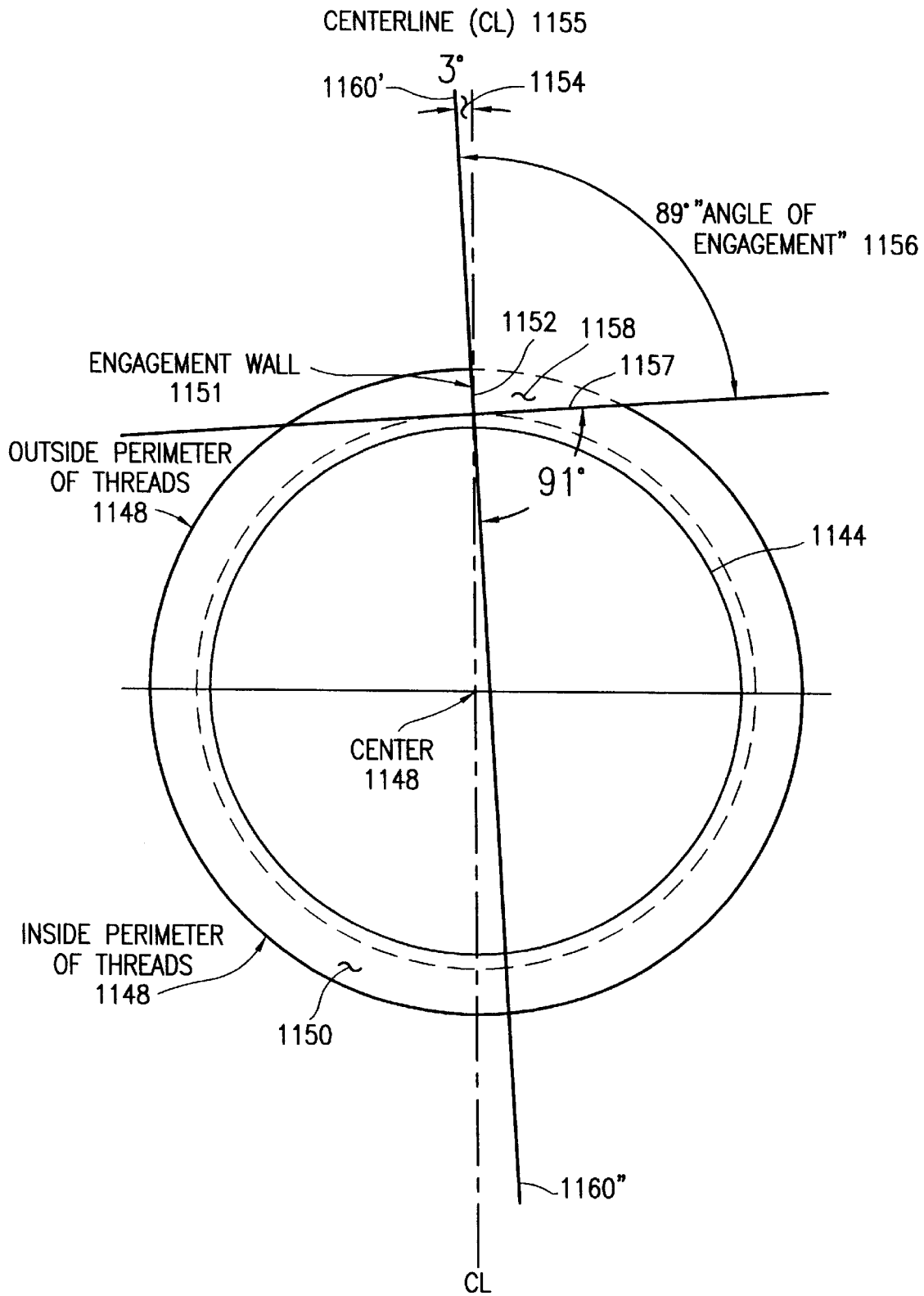
FIG. 6h graphically illustrates the geometry of the angle of engagement.

FIGS. 6h graphically illustrates the preferred angle of engagement. Rotating body 1144 rotates about axial centerline 1146. The root or inside perimeter of the threads 1147 and the outside perimeter of the threads 1148 establish locking zone 1150. Engagement wall 1151 includes a locking face 1152 that has a slope 1154 offset approximately 3 degrees from diametric centerline 1155. The angle of engagement 1156 is approximately 89 degrees and the descending slope 1157 of cutout or groove 1158 has an angle of approximately 91 degrees offset from imaginary line 1160'–1160". That imaginary line is coextensive with locking face 1152 of the cutout or groove 1158.

Figure 6I:
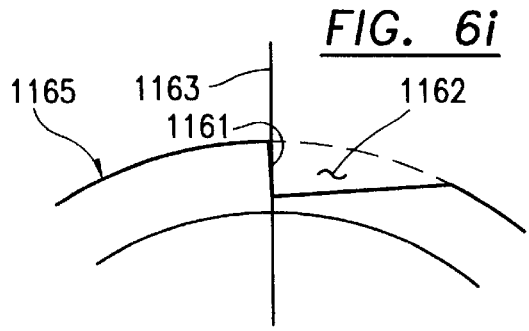
FIGS. 6i–6q diagrammatically illustrate engagement or locking face wall designs.
Figure 6J:
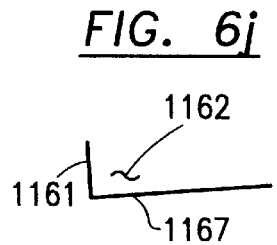
Figure 6K:
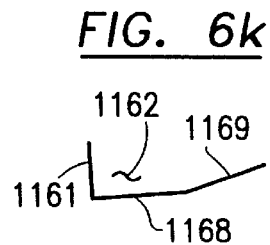
Figure 6L:
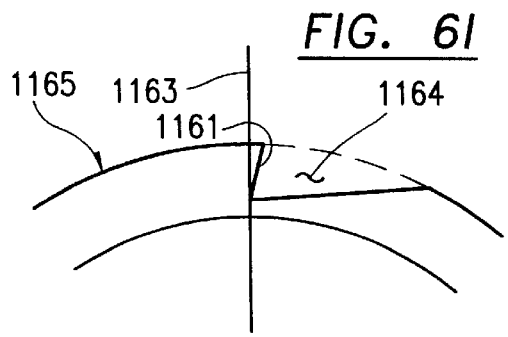
Figure 6M:
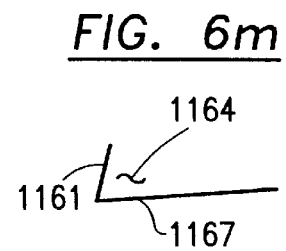
Figure 6N:
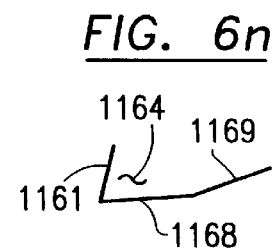
Figure 6O:
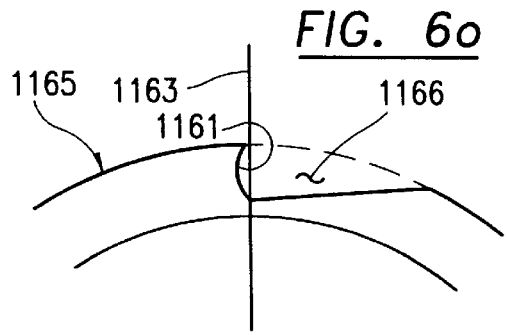
Figure 6P:
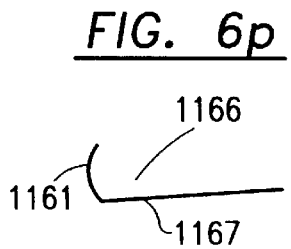
Figure 6Q:
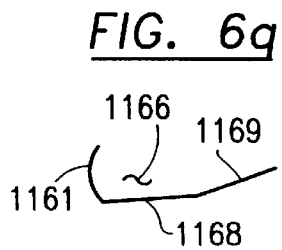

FIGS. 6i, 6l and 6o graphically illustrate a straight wall groove or cutout 1162, and overhang cutout or groove 1164 and a concave cutout or groove 1166. A radial line 1163 passes through the axial centerline of rotating body or bolt 1165. Preferably, that the angle of engagement between groove or cutout 1162, 1164, 1166 and the distal tine end (not illustrated) be less than 90 degrees in order to prevent the tine from disengaging from the groove. FIGS. 6j, 6m and 6p diagrammatically illustrate a flat descending wall 1167. In contrast, FIGS. 6k, 6n and 6q graphically illustrate a base wall 1168 and an angularly offset descending wall 1169. The overhang on the walls shown in FIGS. 6m, 6n, 6p and 6q tend to decrease the angle of engagement along locking or engaging wall 1161. It is believed that the "three wall" groove design shown in FIGS. 6k, 6n and 6q (and FIG. 2c), increases the load carrying thread surface and permits increased torque tension strength within locking zone 1162, 1164, 1166. This, as a result, results in a better angle of engagement for the distal end of the tine. Further, the three wall pattern for locking zone or groove 1162, 1164, 1166 enables the use of a thicker tine and permits the designer to select different materials (different types of steel, metal or plastic).

Figures 7A, 7B, 7C, 7D:
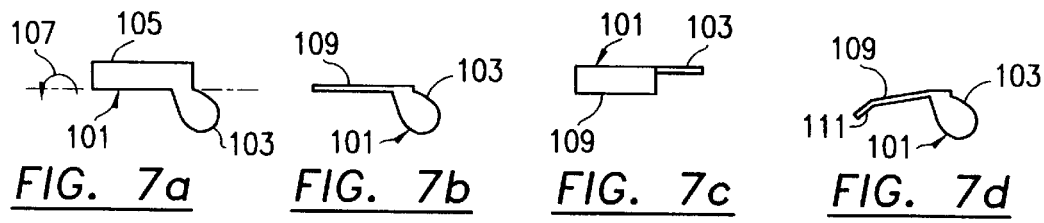
FIGS. 7a, b, c and d diagrammatically illustrate a tine with a proximal end loop formed as a solid planar element and the tine body twisted and the depending normally from the solid body proximal end loop plane.

FIGS. 7a, b, c and d and FIG. 8 are discussed concurrently herein. FIGS. 7a–d show various manufacturing stages for tine 101. In FIG. 7a, tine 101 is formed by stamping or cutting the tine from a sheet of metal. Although the tines described herein are preferably made of metal, and particularly spring steel metal, plastic tines and plastic nuts and bolts may also be utilized. Tine 101 in FIG. 7a includes a proximal end loop 103 which is formed as a solid planar element. In FIG. 7a, tine segment 105 includes both the planar tine body and the distal tine end. Tine segment 105 is rotated out of the plane established by solid planar element 103 by rotating segment 105 in the direction shown by arrow 107. In FIG. 7b, tine 101 has a sold planar element 103 and a planar tine body 109 which is perpendicular with respect to solid planar element 103. FIG. 7c is a side view of tine 101. FIG. 7d illustrates tine 101 as having a solid planar element 103 which establishes the proximal tine end loop of tine 101, a planar tine body 109 and a distal tine end 111 which is angularly offset with respect to planar tine body 109. Distal tine end 111 is formed by bending a tine segment to an angle offset with respect to planar tine body 109.

In FIG. 8, tine 101 has been mounted into arcuate recession 112 in nut 114. Recess 112 is generally similar to recess 90 in FIG. 6a and recess 62 in FIG. 4. As such, recess 112 includes a recessional mouth open to the internal passageway of nut 114, a central region forming a radial free space behind tine body 109 and a tangential cavity tangentially disposed with respect to nut thread 116. The tangential cavity is generally similar to tangential cavity 94 in FIG. 6a. As such, the tangential cavity is generally coplanar with respect to central region 117 of recess 112. Distal tine end 111 moves into and out of the notches formed in bolt 118. The solid planar element 103 is sized to conform with the tangential cavity of recess 112. As shown in FIG. 8, distal tine end 111 is riding atop the bolt thread crest of bolt 118. Accordingly, the planar tine body and the distal tine end 111 are disposed in the radial free space of the recess 112 which has been diminished by the radially outward movement of the distal tine end 111.

Figure 9:
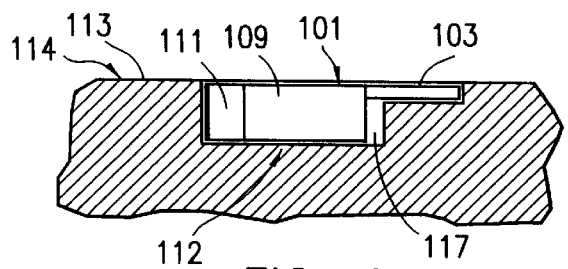
FIG. 9 diagrammatically illustrates a cross-sectional plan view of the tine with the solid planar element from the perspective of section line a'–a" in FIG. 8.

FIG. 9 diagrammatically illustrates a partial, cross-sectional view of tine 101 from the perspective of section line a'–a" in FIG. 8. Distal tine end 111 and tine body 109 move within central region 117 of recess 112. This recess is formed or cut into end face 113 of nut 114. The solid planar element 103 is trapped in a shallow recess in nut 114.

FIG. 10 shows nut 114 having a recess 119 having a slightly different shape. Also, tine 120 has a solid planar proximal tine end loop 121 which is shaped complementary to tangential cavity 122. Tine 120 also has a tine body that is tangential with respect to the axial centerline of bolt 123 and is perpendicular to solid planar element 121 which defines the proximal end loop of tine 120.

Figure 12:
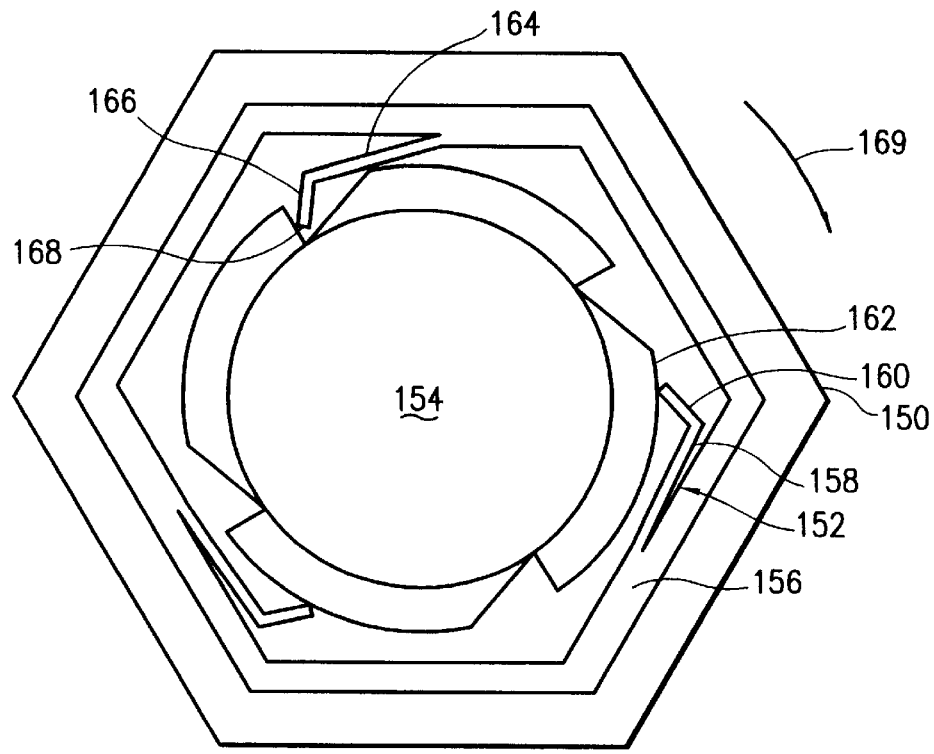
FIG. 12 illustrates a nut having a nut insert disposed in a circumferential recess and a bolt threaded into the nut.

FIG. 12 illustrates nut 150 carrying nut insert 152. The nut insert is disposed in a circumferential recess on the end face of the nut. Bolt 154 is threaded onto nut 150. Nut insert 152 includes a peripheral ring 156 and a plurality of tines one of which is tine 158. Tine 158 includes a distal tine end 160. In FIG. 12, distal tine end 160 is riding atop bolt thread crest 162. Tine 164, and in particular distal tine end 166, has fallen into notch 168. Distal tine end 166 prevents counter-rotational movement in the direction shown by arrow 169 with respect to a fixed nut position for nut 150.

Figure 13:
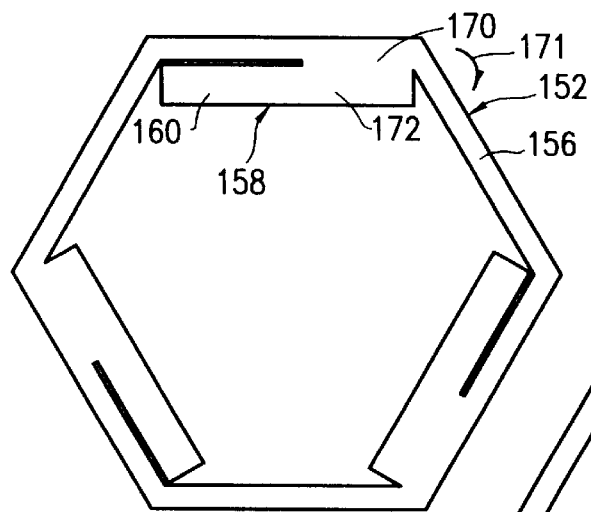
FIGS. 13 and 14 illustrate the nut insert at various production stages before and after the tines have been twisted from the plane defined by the peripheral ring body of the nut insert.
Figure 14:
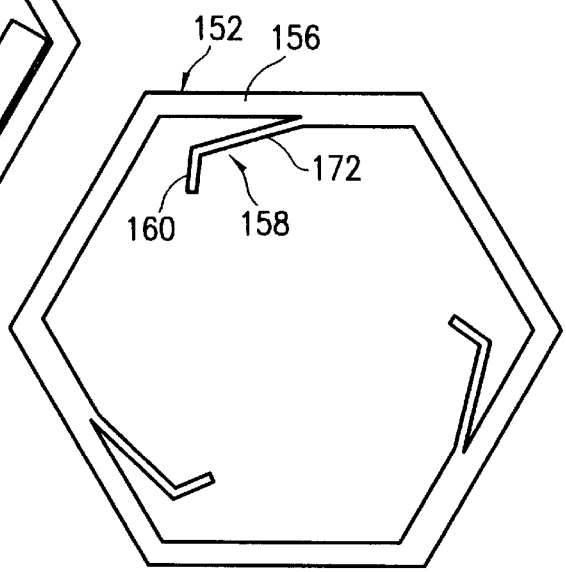

FIGS. 13 and 14 show various manufacturing stages for nut insert 152. In FIG. 13, nut insert 152 has been stamped or cut from a planar sheet of metal, such as spring metal. Alternatively, plastic may be used. Each tine, one of which is tine 158, includes a proximal tine portion 170, a tine body 172 and a distal tine end segment 160. In FIG. 14, tine body 172 has been rotated in direction shown by arrow 171 in FIG. 13 such that tine body 172 is in a plane perpendicular to peripheral ring 156 of nut insert 152. Further, the distal tine end 160 has been bent and angularly offset with respect to the generally planar tine body 172.

Figure 15:
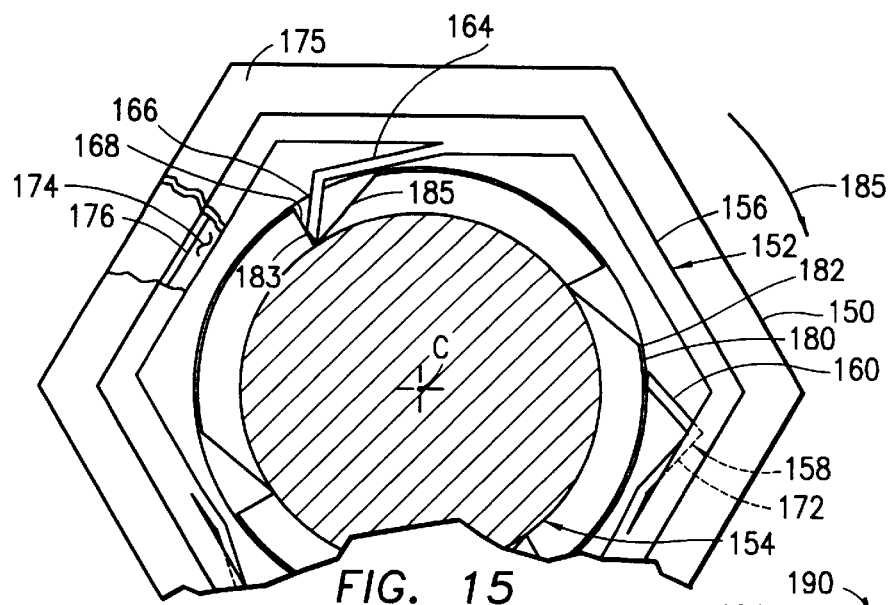
FIG. 15 illustrates a partial, cut-away view of the nut insert and particularly shows the shoulder in the recess and the displacement of the distal tine end and a portion of the tine body in a radial space beneath the nut insert.

FIG. 15 shows a partial, cross-sectional, broken away axial end view of nut 150 and nut insert 152. Nut insert 152 is placed in a recess 174 and is specifically disposed atop a shoulder 176 in recess 174. Recess 174 is established below the nut end face 175. In the illustrated embodiment, nut insert 152 is formed with a complementary shape as compared with recess 174. Since nut insert 152 is placed atop shoulder 176, the nut insert 152 forms a radial free space there below within which tine 158 moves. Distal end 160 rides atop bolt thread crest 180. The peripheral ring 156 of nut insert 152 is established about the crest of nut thread 182. Although three tines are shown in FIGS. 12 and 15, the nut insert may operate with a single tine. When distal tine end 166 falls in notch 168 and abuts locking face 183, counter-rotational movement of the bolt with respect to a fixed nut in the direction shown by arrow 185 is prohibited. Rotational movement opposite to direction 185 permits distal tine end 166 to move along opposing slope 185 of notch 168 and also to move atop bolt thread crest 180. When the distal tine end rides atop the bolt thread crest, the tine body and a portion of the distal tine end flex within the radial free space defined beneath the peripheral ring 156 of nut insert 152. As shown with respect to tine 158, tine body 172 generally falls within a substantially tangential plane with respect to the axial centerline C of bolt 154.

Figure 16:
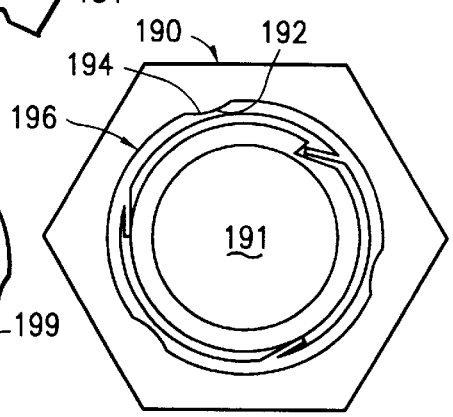
FIG. 16 shows a nut insert mounted to a nut and a bolt threaded on the nut.

FIG. 16 shows nut 190 having a plurality of keys 192 which are aligned with keyways 194 on nut inserts 196. In this manner, the nut insert can be aligned in a certain circumferential position with respect to the nut 190. Of course, nut insert 196 could define the keys and the keyways could be defined in the recess established in nut 190.

Alternatively, keyways 194 are simply cut-outs that permit the locking nut insert to be swaged and "locked" into the nut end face. No keys on the nut face are necessary. It is not necessary to orient the locking nut insert on the nut. The nut end face material, during the swaging process fills the keyway 194 thereby locking the insert on the nut.

Figure 17A:
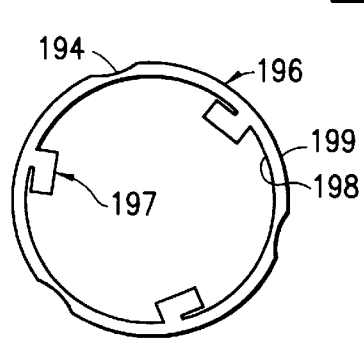
FIGS. 17a and 17b show the nut insert in various stages of manufacture with the tines in the plane of the peripheral ring and the tines depending below the plane.
Figure 17B:
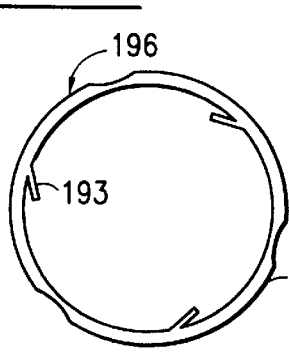

FIGS. 17a and 17b show various stages of manufacture of the nut insert. In FIG. 17a, nut insert 196 is flat cut or punched from a sheet of steel (preferably spring steel).

Keyway or cut-out 194 is clearly shown in FIG. 17a. A plurality of tines, one of which is tine 197, are formed on a radially inward peripheral edge 198 of peripheral ring 199 of the nut insert 196. In FIG. 17a, these tine bodies 197 have been rotated such that they depend beneath the plane established by peripheral ring 199. Accordingly, the distal tines ends, one of which is distal tine end 193, extend generally tangentially and radially inward toward the axial centerline of the specially configured bolt. The tines are circumferentially disposed around edge 198 of the planar peripheral ring 199 of nut insert 196. Each tine 193 has a planar body which is generally tangentially disposed with respect to the axial centerline of bolt 191.

Figure 18:
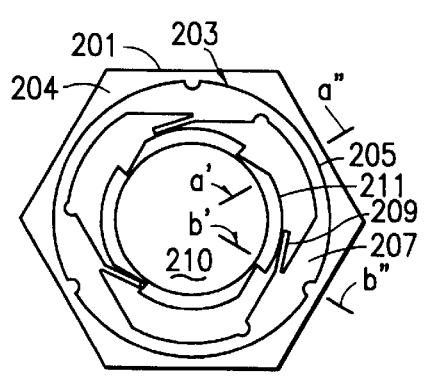
FIG. 18 illustrates a nut insert having planar support plates for the tines with a bolt threaded onto the nut.

FIG. 18 shows nut 201 having a nut insert 203 disposed in a recess below nut face 204. Nut insert 203 includes a peripheral ring 205 and a plurality of planar support plates, one of which is support plate 207 associated with tine 209. Tine 209 rides atop bolt thread crest 211 for bolt 210. Bolt 210 may be similar to the bolt shown in FIG. 1a, that is, having a longitudinal locking channel, or may be similar to the bolt shown in FIG. 2a, that is, having a spiral locking channel.

Figure 20:
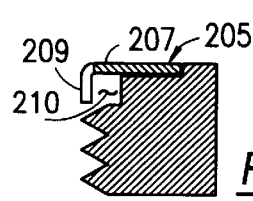
FIGS. 19 and 20 illustrate partial, cross-sectional views of the nut insert and nut from the perspective of section lines a'–a" and b'–b" in FIG. 18.
Figure 19:
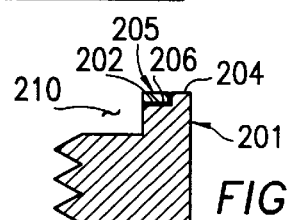

FIGS. 19 and 20 are partial, cross-sectional views taken from the perspective of section line a'–a" and b'–b" in FIG. 18. FIG. 19 shows nut 201 having a nut face 204 and a recess 202 there below. Peripheral plate 205 of the nut insert is disposed on the first level of recess 202 or on a shoulder 206. The recess 202 has a lower region 210. FIG. 20 shows that tine 209 is spaced away from the peripheral walls defining lower recess area 210. In order to provide this radial free space, insert 205 utilizes planar support plates 207 for each tine. The free space is the spacial flex zone.

FIG. 19 also shows that the outer peripheral planar section of nut insert 205 has substantially the same radial dimension as the shoulder 202 in recess 206. This permits the insert to be firmly seated in the recess.

Figure 21:
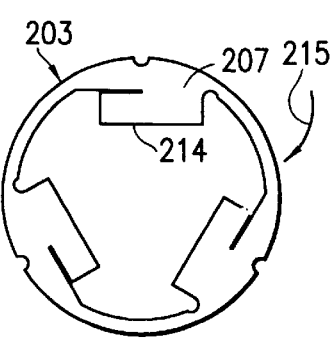
FIGS. 21 and 22 illustrate various stages of manufacture of a nut insert before and after the tines have been rotated or twisted from the nut insert plane.
Figure 22:
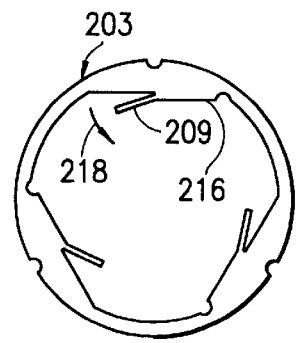

FIGS. 21 and 22 show various manufacturing stages for nut insert 203. In FIG. 21, nut insert 203 is pressed, stamped or cut from a single sheet of metal or plastic. Tine segments 214 extend from planar support plate 207. Tine 209 (FIG. 22) is formed when tine segment 214 is rotated in the direction shown by arrow 215 such that tine body 216 is tangentially disposed with respect to the nut thread and bolt thread. Distal tine 209 is then rotated in the direction shown by arrow 218 such that distal tine end 209 extends tangentially and radially inward toward the axial centerline of the locking unit.

In this configuration, the distal tine ends flex radially inward when the distal tine end is disposed in one or more notches (see FIG. 18, and the tine at 8 o'clock) and the distal tine ends move radially outward into the radial free space (FIG. 20, space 210) when the distal tine end rides on the bolt thread crest as shown with respect to distal tine end 209 in FIG. 18.

FIG. 23 shows nut 220 carrying an elongated locking unit 221 formed as a cylinder on nut end face 222. Elongated locking unit 221 has a rearward ring member 223 which is disposed in a nut recess (see FIG. 29). The elongated locking unit 221 has a cylindrical body 225 with a plurality of tines 226, 228 formed thereon. Each tine has a distal tine end 227 and a proximal tine portion 229. Proximal tine portion 229 is adjacent cylindrical body 225 of elongated locking unit 221. Preferably, distal tine end 227 is formed by cutting out region 230 from cylindrical body 225. A plurality of tines, in a preferred embodiment, are circumferentially disposed about cylinder 225. Additionally, the tines may be axially disposed such that tine 228 is axially inboard with respect to tine 232.

FIG. 24 shows bolt 231 having a bolt thread trough 233, a bolt thread crest 234 and a plurality of notches, one of which is notch 235. Each notch includes a locking face 236 and an opposing slope 237.

FIGS. 25a and 25b show bolt segments 11 and 13 carrying a plurality of notches thereon. With respect to bolt segment 11 in FIG. 25a, the plurality of notches are longitudinally aligned to form longitudinal locking channel 9. With respect to bolt segment 13 in FIG. 25b, the notches are aligned in a predetermined spiral pattern to form spiral locking channel 7.

FIG. 26 shows nut 220 threaded onto bolt 231. Locking unit 221 is locked onto bolt 220. Tine 228 is in a locked or engaged position with its distal tine end abutting a locking face in the locking channel. This is the locking zone. In contrast, distal tine end 232 is riding atop the opposing slope in the flex zone. Tine 240 is riding atop bolt thread crest 234.

FIG. 27a shows an elongated locking unit 241 having a cylindrical body 225 with circumferentially disposed distal tine ends 226, 232. FIG. 27b shows locking unit 221 with distal tine ends 226, 228 and 232 both circumferentially disposed about cylinder 225 and axially disposed about cylinder 225. The locking mechanisms in FIGS. 27a and 27b are sometimes referred to herein as "railroad" designs.

FIG. 28 illustrates bolt 1 having a plurality of longitudinal locking channels 3 about to be threaded onto nut 220 carrying elongated locking unit 221.

FIG. 29 shows elongated locking unit 221 having an axially rearward ring 223 disposed in a recess 242 beneath end face 222. One method of attaching rearward ring 223 in recess 242 is by swaging the nut face 222. Otherwise, the ring may be snap fit into recess 242. The ring may also be inserted via a key and rotated to block or trap the key in a keyway. The key and keyway locking is not the preferred embodiment.

FIG. 30a shows bolt 1 locking panels 4, 5 via nut 220 and locking unit 221. The user can easily determine whether the tines 228, 232 have fallen into one of the locking channels 3 by viewing the position of the tine in the cut-out. For example, with reference to tine 228, cut-out 230 enables the user to visually identify whether the tine has been placed in the locking channel.

Referring to FIG. 26, tines 228, 232 and 240 protrude both tangentially and radially toward the axial centerline of bolt 231. The placement of tines 232, 228 and 226 (FIG. 23) in respective cut-outs (for example tine 228 in cut-out 230) enhances the visibility of the locking action of each tine. As shown in FIG. 26, the rearward ring 223 of locking unit 221 has a complementary key and keyway fit in region 246. As shown, the rearward ring defines the keyway and the nut recess or nut end surface 222 defines a complementary key. This key and keyway fit permits the circumferential alignment of locking unit 221 with respect to a certain position on nut 220. In the railroad design, liquid will not accumulate in the locking mechanism.

Figure 30F:
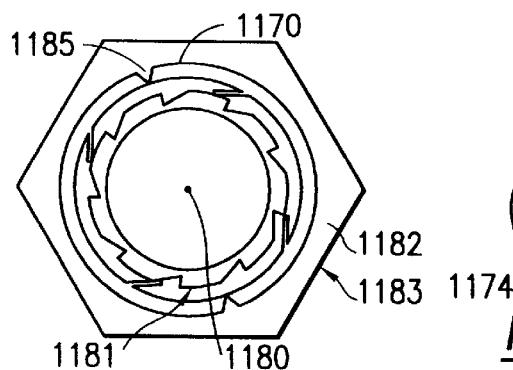
FIG. 30f diagrammatically illustrates the top hap design or insert mounted in a nut.
Figure 30B:
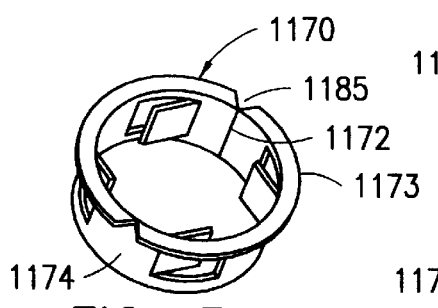
FIGS. 30b–30e diagrammatically illustrate the top hat design which includes a single, radial end plate above a cylindrical locking unit.
Figure 30C:
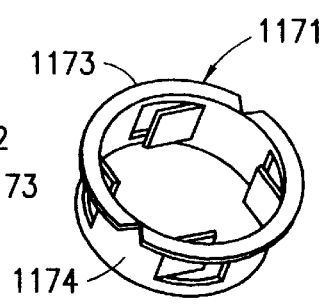
Figure 30E:
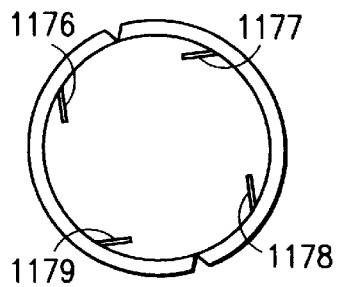
Figure 30D:
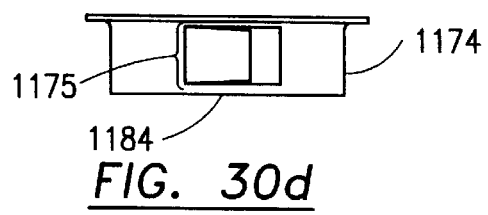

FIG. 30b diagrammatically illustrates a top hat design or nut insert. Elongated locking unit 1170 is substantially similar to elongated locking unit 1171 shown in FIG. 30c except that unit 1170 includes a seam 1172 whereas locking unit 1171 does not have a seam. Unit 1171 is manufactured by poking a "bubble" in a thin metal sheet, breaking through the bubble, forming a tube, lancing the tube and then creating axially forward ring plate member 1173. In contrast, locking unit 1170 is created from a flat strip of metal (or plastic) which is cut, folded, and wrapped on a mandrill to form barrel or the cylinder. Any material which can be cut, folded and wrapped may be utilized. Seam 1172 is spot welded or is left open such that the cylinder acts a spring. Both locking units 1170, 1171 include a cylinder 1174. The cylinder has a central region 1175 shown in FIG. 30d and carries at least one, and preferably, a plurality of tines. The top hat design illustrated in FIGS. 30b–30e include four tines 1176, 1177, 1178 and 1179 carried by the cylindrical lock body shown in FIG. 30e. These tines protrude tangentially and radially towards axial centerline 1180 of rotating bolt or body 1181. Axially centerline 1180 is shown in FIG. 30f.

The top hat design is unique in that tines 1176–1179 are disposed in a central region 1175 in cylinder 1174. This central disposition of the tines provides stability and extra strength since cylinder 1174 has a lower peripheral axial ring section 1184 shown in FIG. 30d and an upper ring normal to radial top hat lip 1173. When locking unit 1170 is placed in a recess defined on the end face of a nut (see the recess in FIGS. 11, 19 and 20 for example), the locking unit is swagged onto end face 1182 of nut 1183 (FIG. 30f) and the swagged portion of end face 1182 "flows up" to lock into the V formed on axially forward radial ring 1173. Other cut-outs are useful. See FIGS. 17a, 18. V 1185 is shown on forward axial radial ring 1173 of locking unit 1170 in FIG. 30b. V 1185 is swagged into nut end face 1182.

Since there is no reason to circumferentially orient the top hat or locking unit 1170, 1171, the top hat design is easier to assemble. It is only necessary to orient the top hat design such that lower axial edge 1184 (FIG. 30d) is disposed near the nut end face such that the locking nut insert drops into the recess on the nut face. Further, the present top hat or locking unit design 1170, 1171 is easily handled by automatic feeding units. The lower circumferential ring 1184 prevents the nut inserts from locking together and also ensures that tines 1176–1179 are not altered, deformed or otherwise harmed during the automatic feeding and insertion into the nut recess. If the tines become dented, the locking ability of the system is adversely effected. It is important to note that the automatic sorting and handling of these fasteners is an important feature of the present invention.

Figure 30G:
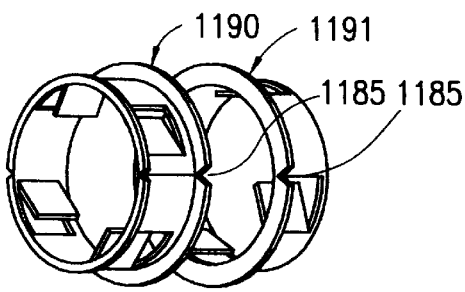
FIGS. 30g–30i diagrammatically illustrate axially stacked locking units or inserts.
Figure 30H:
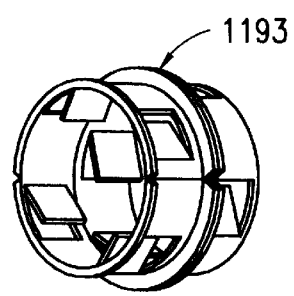
Figure 30I:
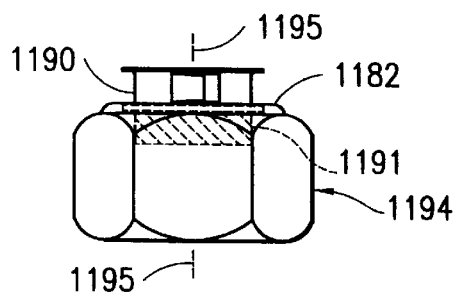

FIGS. 30g–30i diagrammatically illustrate axial stacking of two top hat locking units 1190 and 1191. Locking units 1190 and 1191 are aligned such that V cutouts 1185 on each locking unit are axially aligned. Thereafter, the two top hat locking units are attached by adhesion, spot welding or otherwise to form a composite unit 1193. The top ring of the assembled units as smaller in diameter to allow an installation toll to reach the area to be fastened. Composite unit 1193 is then inserted into nut 1194. Lower or axially inboard locking unit 1191 is placed in the recess on the end face 1182 of nut 1194. The upper locking unit or axially outboard locking unit 1190 extends axially outboard from nut face 1182. Of course, the dual locking units 1190, 1991 are coaxial with axially centerline 1195 of nut 1194. The dual top hat locking unit 1190, 1191 provides multiple, circumferentially disposed tines thereby enhancing the locking capability of the system. This peripheral and axial distribution of tines both axially and circumferentially is described above in connection with the railroad design shown in FIG. 27b.

The top hat locking unit design (FIGS. 30b, 30c) are different from prior art designs in that the present invention is a single part and not a multiple part piece. The prior art does not have a lower circumferential ring 1184 (FIG. 30d) and hence, is difficult to sort, automatically feed and assemble in a nut recess. These features are important in the present invention.

General comments regarding the axial end locking mechanism follow.

The invention relates to a cylinder extending axially from an end of a nut wherein the cylinder carries locking elements thereon.

The invention also relates to a locking clip or insert with tines supported in an axial manner (with respect to the axial centerline of the nut), and tines emanating from the axially disposed cylindrical body that pass through a spacial flex zone and engage grooves in a screw.

Since the locking mechanism is axially outboard from the nut, water or other liquid cannot pool in the locking mechanism. This reduces the possibility of corrosion of the mechanism in adverse environments or outdoors.

General comments regarding the "top hat" design follow.

A protective rim or peripheral wall axially above and below, alongside the tine (a) protects the integrity of the locking mechanism at all stages of manufacture including shipping, storage, handling and installation; (b) allows shipping of tine components in bulk, preventing entanglement prior to installation in the nut and allowing for high speed installation in any swaging process; and (c) will shield any sharp edges of the tines when protruding from the locking mechanism. This makes the locking mechanism safer to handle and reduces the risk of something catching on the locking mechanism including loose clothing.

General comments on the axial stacked embodiment follow.

In an axial stacked mode (two top hat designs stacked together), one locking insert is keyed to the second insert. This provides a maximum amount of tine engagements equally separated for either maximum engagements with the lowest possible degrees between engagements (see, for example, the earlier example of 8 tines operating on 9 grooves or slots), or the maximum engagements with a specification for multiple or duplicate simultaneous tine engagements (e.g., 8 tines in 8 grooves).

Figure 31:
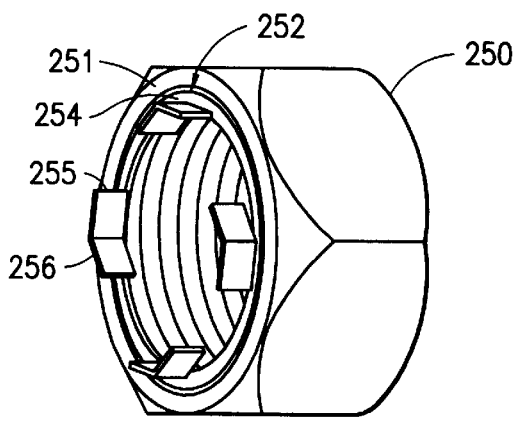
FIG. 31 provides a perspective view of a nut carrying a locking element having a plurality of axially protruding legs and a corresponding plurality of tines.
Figure 32:
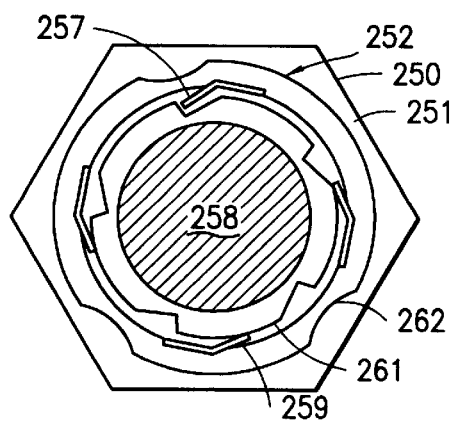
FIG. 32 illustrates the locking action provided by the tines on the locking element, on the nut and on the specially on configured bolt.

FIG. 31 illustrates a perspective view of nut 250 having a locking element 252 disposed in a recess on nut face 251. The recess is similar to recess 242 in FIG. 29. Locking element 252 includes a rearward ring member 254 and a plurality of axially protruding legs 255 extending normally therefrom. Each axially protruding leg includes a tine 256 that protrudes tangentially and radially inward toward the axial centerline of the bolt. FIG. 32 shows an end view of nut 250 with locking element 252 attached to the end face 251 of the nut. Tine 257 is in a locked position in a notch in bolt 258. In contrast, tine 259 is riding on top of bolt thread crest 261. Locking element 252 is keyed to a certain position with respect to nut 250 based upon key and keyway combination 262. As explained earlier, it is not critical whether locking element carries the key or keyway as long as the complementary key or keyway element is formed on the appropriate portion of nut end face 251. Alternatively, the cut-outs or keyways on the locking element may be locked to the nut end face by swaging the radially extending lip of the locking unit to the nut end face. In a swaged mode, nut end face material "flows" into to keyway to lock both units together. This swaged., locking feature is discussed earlier herein.

Figure 33A:
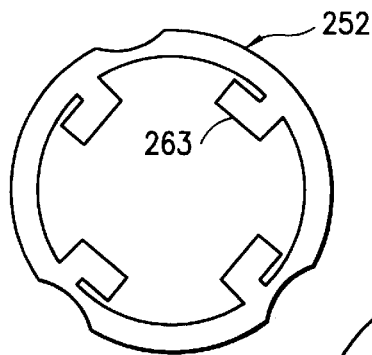
FIGS. 33a and 33b illustrate various stages of manufacture of the locking element with the axially protruding legs and tines.
Figure 33B:
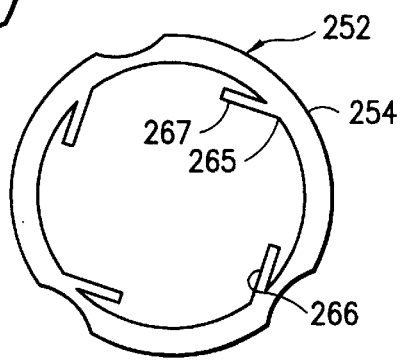

FIG. 33a and FIG. 33b show various stages of manufacture of locking element 252. In FIG. 33a, locking element 252 is cut, stamped or pressed from a single sheet of steel or metal, preferably spring steel. Alternatively, plastic may be utilized. A tine segment 263 is formed by cutting, pressing or otherwise. In FIG. 33b, tine segment 263 has been rotated such that it is in a plane perpendicular to the plane of rearward ring member 254. Tine segment 263 includes a proximal tine portion 265 and a distal tine end 267. A proximal tine portion 265 is generally perpendicular to radially inward edge 266 of ring member 254. The distal tine portion 267 protrudes tangentially and radially inward toward the axial centerline of the bolt. This centerline is coaxial to the centerline of the nut.

Figure 34:
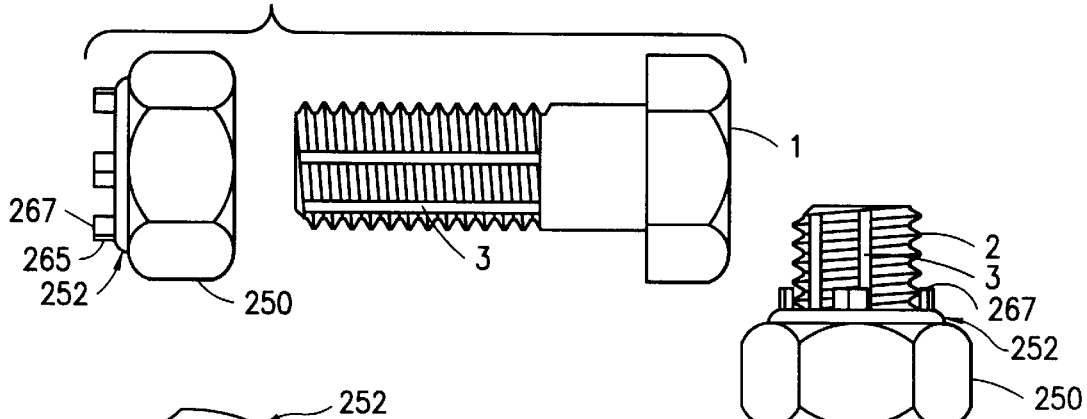
FIG. 34 illustrates a specially configured bolt and a nut carrying the locking element with the axially protruding legs.

FIG. 34 shows bolt 1 having a plurality of longitudinal locking channels 3 and nut 250 carrying locking element 252. The axially protruding legs of the proximal tine portion 265 are clearly shown. These legs protrude normally from the ring member of the nut insert. The distal tine portion 267 is angled inward to catch one or more notches in the longitudinal locking channel 3. Of course, a spiral locking channel 7 shown on bolt segment 13 in FIG. 25b may be utilized. A plurality of tines are circumferentially spaced about locking element 252.

Figure 35A:
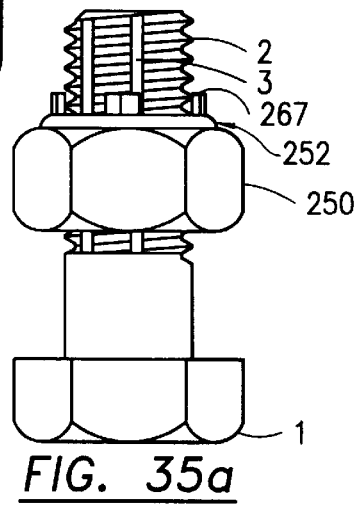
FIG. 35a shows the nut carrying the locking unit threaded onto the special bolt.

FIG. 35a shows nut 250 carrying locking element 252 and locking onto bolt 1. The user can visibly confirm whether one or more of the distal tine ends 267 have locked into locking channel 3. Also, when the distal tine ends 267 ride atop bolt thread crest 2, this can be visibly confirmed by the user. Locking element 252 can be swaged onto nut face 251 as shown in FIG. 29 or snapped into the recess FIGS. 35b–35e diagrammatically illustrate various mechanisms to swage or attach or affix the axially disposed radially extending rim or lip of various locking units or nut inserts. For example, rim 1173 in FIG. 30b; plate 156 in FIG. 13; plate 205 in FIGS. 18, 19; plate 223 in FIG. 29; among others. FIG. 35b diagrammatically shows nut 1202 having primary nut recess 1204 and radial wall or ledge 1206. In addition, nut end face 1208 includes an axial protrusion 1210. In FIG. 35c, locking unit or nut insert 1213 has been disposed in nut recess 1204. Locking unit 1213 includes at an axial end, a radial plate 1215. In order to secure locking unit 1213 in nut recess 1204, axial protrusion 1210 has been flattened or deformed as shown as deformation 1211 to cover a reasonable portion of radial end plate 1215. This mechanism effectively locks the locking unit 1213 or nut insert into nut recess 1204.

Figure 35D:
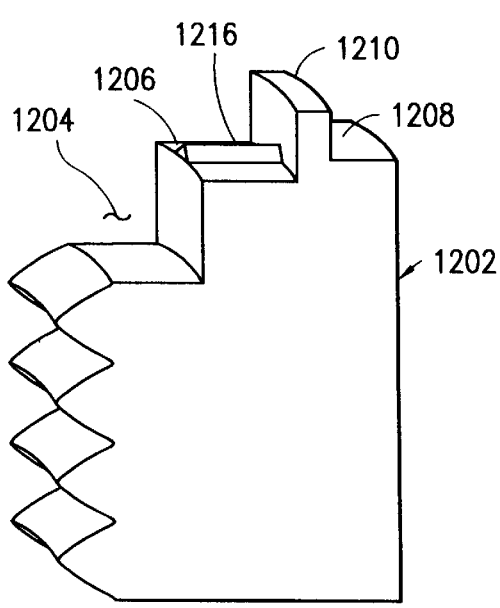
FIGS. 35b–35e diagrammatically illustrate radial rim locking features on and about nut faces to affix the locking inserts or locking units into the nut.
Figure 35E:
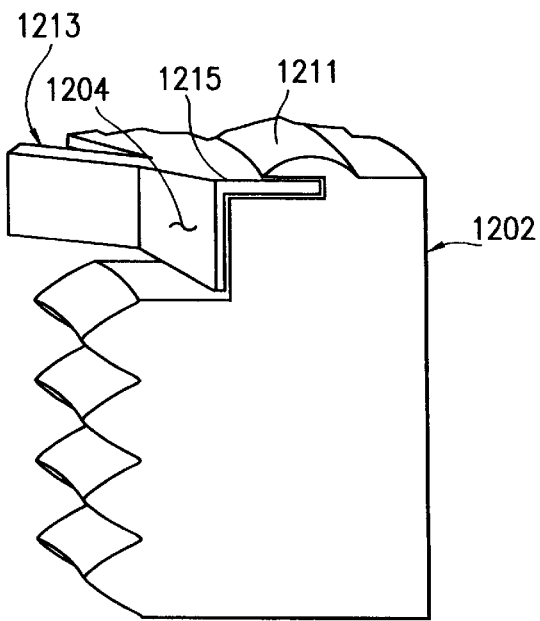
Figure 35B:
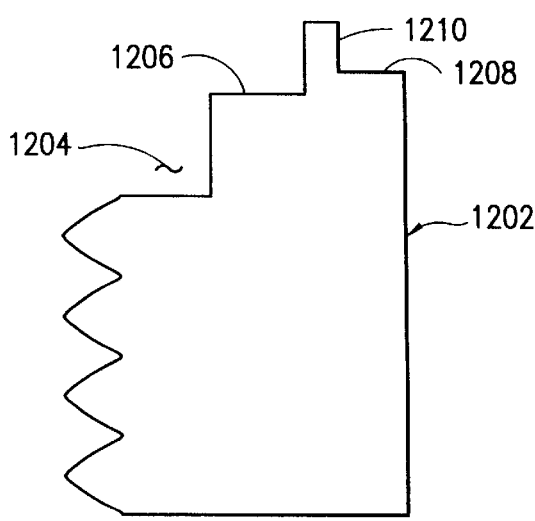
Figure 35C:
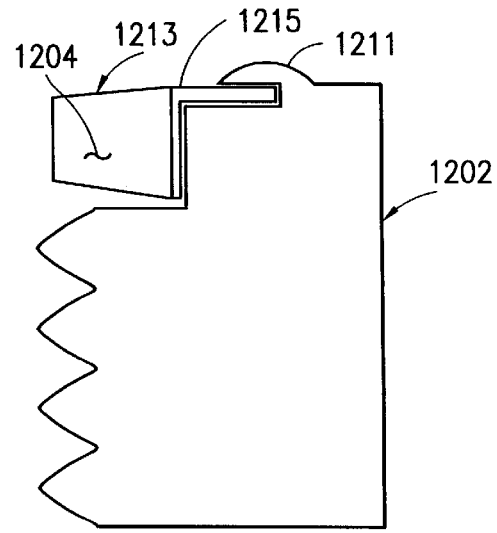

In FIGS. 35d–35e, radial ledge 1206 of nut 1202 includes a striation or slight radially aligned, axial protrusion or ridge 1216. When nut insert 1213 is placed in nut recess 1204 and radial ring or plate 1215 is placed thereon, upon deformation of axial ridge 1210 to form deformation 1211, the bump or striation 1216 provides a sturdy anti-rotation lock between deformation 1211 and ridge 1216. This anti-rotation lock results in a similar deformation of radial ring 1215 on nut insert 1213.

FIGS. 35h–35oo relateto fasteners, clips or nuts formed from essentially sheet metal. Similar numerals designate similar items in this group of figures. In the industry, these structures may alternatively be called locking fasteners, locking nuts or locking clips. Further, it should be noted that these locking fastener structures may be mounted on a clip leg established by a U, J or S-shaped clip. The fastener on a U-shaped clip is shown in FIG. 46c. The fastener on a clip leg on a J-shaped clip is shown in FIG. 46k. S-shaped clips are shown in FIGS. 37 and 38a. Generally, U, J or S-shaped fastener designs are interchangeable, i.e., it does not matter whether the fastener is mounted on a U, J or S-shaped clip body.

Figure 35H:
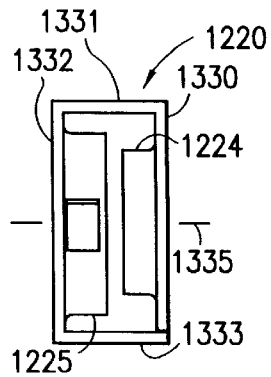
FIGS. 35f–35oo diagrammatically illustrate stamped (and partially extruded) locking nuts or fastener clips.
Figure 35I:
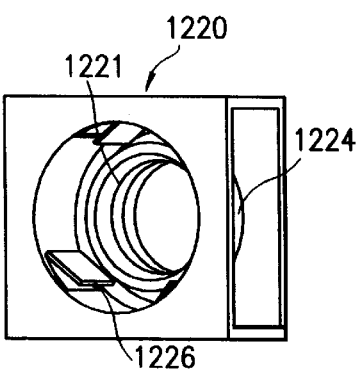
Figure 35K:
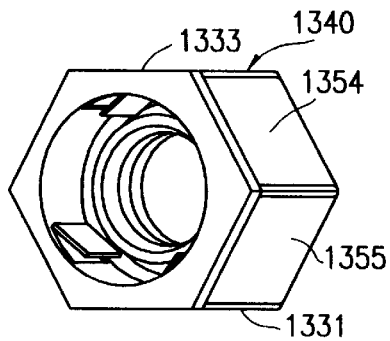
Figure 35F:
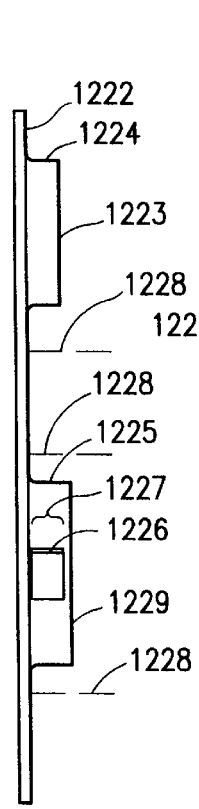

FIGS. 35f–35i ultimately form nut, clip or fastener 1220. FIG. 35h diagrammatically illustrates a side view of fastener 1220 and FIG. 35i diagrammatically illustrates a prospective view of the fastener. In FIG. 35f, the fastener is shown at an early manufacturing stage wherein sheet metal plate 1222 has been partially extruded to form thread barrel 1224 and cylindrical body 1225. The extrusion has been threaded. Tines 1226 have been punched or tooled into a medial portion 1227 of cylinder 1225. The dashed lines 1228 in FIG. 35*f* identify hinge or bend regions for partially manufactured sheetplate 1222. Dashed lines 1228 in this group of FIGS. 35*f*–35*oo* indicate bend lines.

To partially manufacture sheet metal plate 1222, a bubble is created to form thread barrel 1224. The bubble is then lanced or cutoff to form axial edge 1223. In a similar manner, a bubble is formed on plate 1222 in order to form locking cylindrical body 1225. That bubble is cut or lanced to form edge 1229. Thereafter, cylinder 1225 is put on a mandrel or other properly shaped tool or dye and a radial stamp tool is radially inserted at medial region 1227 to form tine 1226.

Figure 35G:
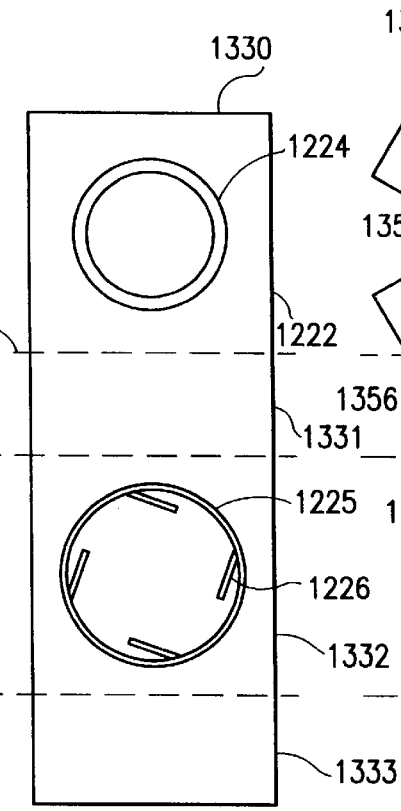

As shown in FIG. 35*g*, thread barrel 1224 and cylindrical body 1225 extend above sheet plate 1222. Tines 1226 extend tangentially and radially inward towards the axial centerline.

In order to form fastener 1220 shown in FIGS. 35*h* and 35*i*, plate section 1330 is bent at bend planes 1228 shown in dashed lines in FIG. 35*g*. Intermediate section 1331 becomes a side wall for fastener 1220. Cylindrical locking body 1225 carried by plate section 1332 is axially disposed, in a coaxial manner along axial centerline 1335. The axial centerline of threaded barrel 1224 and the axial centerline of cylindrical locking unit 1225 is coaxial. Plate section 1333 is bent to form another side of fastener 1220. The completed product is shown in perspective in FIG. 35*i* wherein tines 1226 extend radially and tangentially towards the axial centerline 1335 and threads 1221 are visible on thread barrel portion 1224.

Although sheet metal is currently used to make these fasteners, other composite materials or plastic may be used.

Figure 35J:
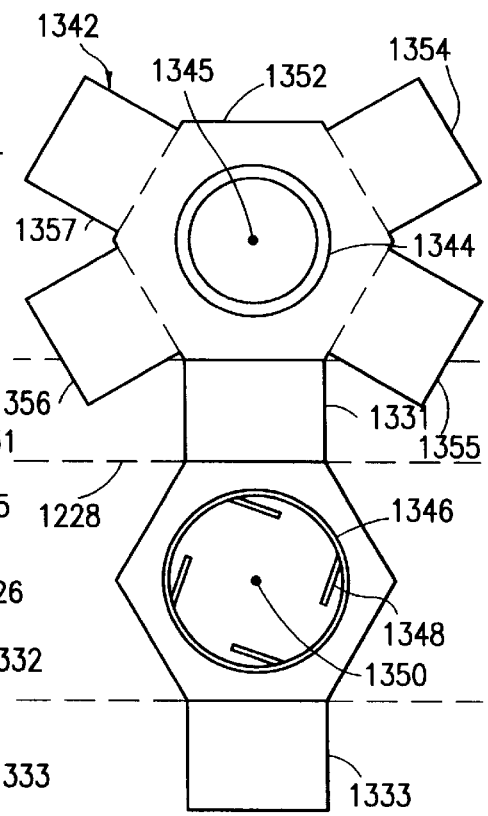

FIGS. 35*j* and 35*k* show an initial manufactured phase and a final manufactured phase for fastener 1340. Partially manufactured sheet plate 1342 in FIG. 35*j* has an extruded threaded barrel 1344 and an extruded locking cylinder 1346. A plurality of tines 1348 extends radially and tangentially in the axial centerline 1350 of locking cylinder 1346. Partially manufactured sheet plate 1342 is bent as shown in FIG. 35*j*. Additionally, nut or fastener end plate 1352 has extending therefrom face plates 1354, 1355, 1356 and 1357. Prior to or subsequent to axially alignment of axial centerline 1350 and axial centerline 1354 (related to threaded barrel 1344), side faces 1354–1357 are bent to enclose fastener 1340. Plate sections 1331 and 1333 enclose the other sides of fastener 1340. The completed fastener is shown in FIG. 35*k*. Plate sections 1331, 1333 protect the tines from damage during shipping etc., and provide axial stability and support for the clip fastener.

Figure 35N:
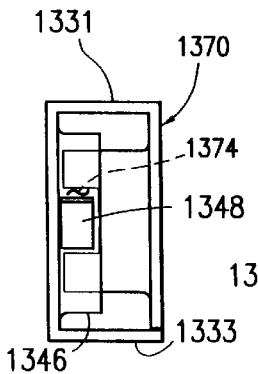
Figure 35O:
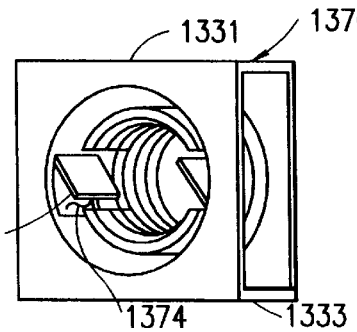
Figure 35Q:
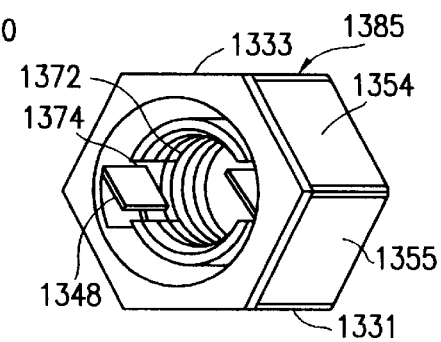
FIGS. 35pp–35ss diagrammatically illustrate a locking drawn barrel fastener.
Figure 35L:
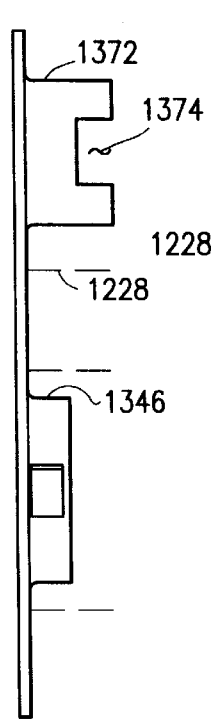
Figure 35M:
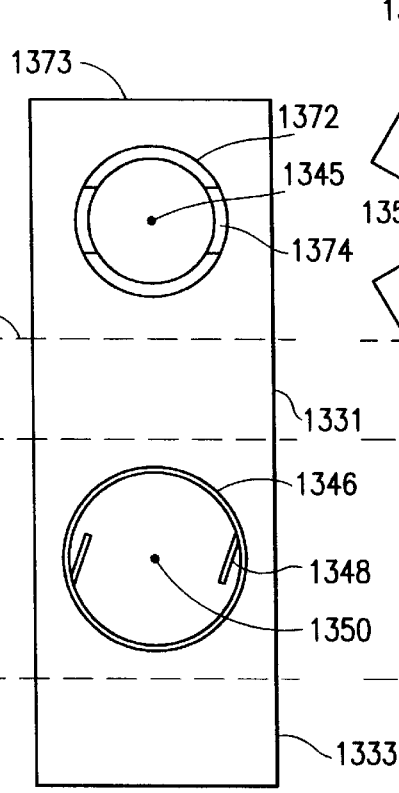

With respect to FIGS. 35*l*–35*q*, similar numerals designate similar items. Only significant differences in the structures will be discussed herein. FIGS. 35*l*–35*o* diagrammatically illustrate the partially manufactured and finished version of fastener 1370. In FIG. 35*l*, extruded threaded bore 1372 has been partially cut to form cutout 1374. Before or after establishing cutout 1374, cylinder 1372 is threaded. Partially manufactured plate 1373 is bent at lines 1228 such that axial centerline 1345 of threaded bore 1372 is coaxial with axial centerline 1350 of locking cylinder 1346. Further, tines 1348 are disposed in cutouts 1374. This is shown in perspective in FIG. 35*o*. As a result, fastener 1370 has a compact shape and threaded bore 1372 carries a greater number of threads thereby enhancing the fastening capability of fastener 1370.

Figure 35P:
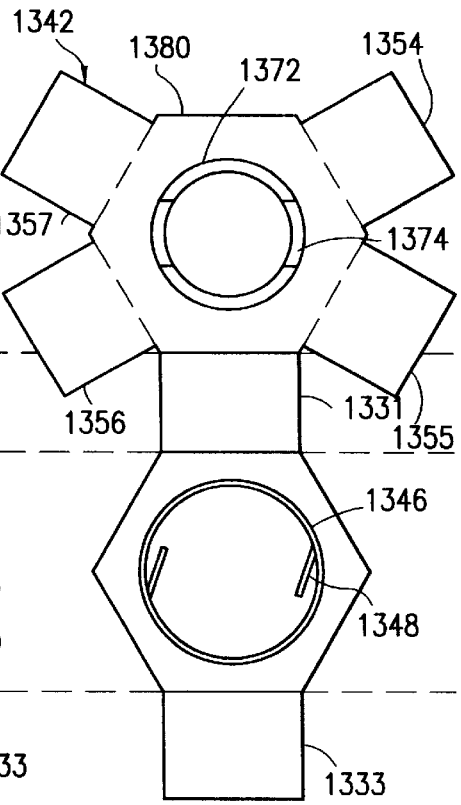
Figure 35L:
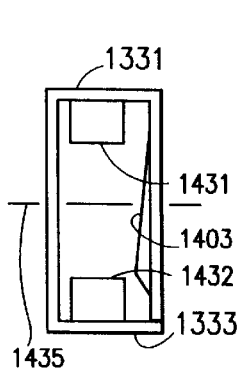
Figure 35M:
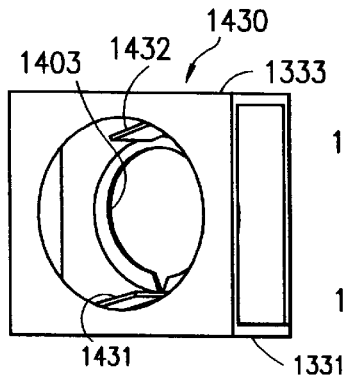
Figure 35O:
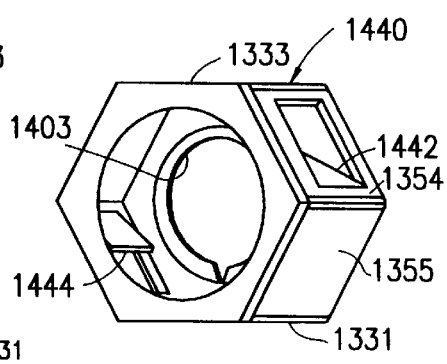
Figures 35J, 35K, 35N:
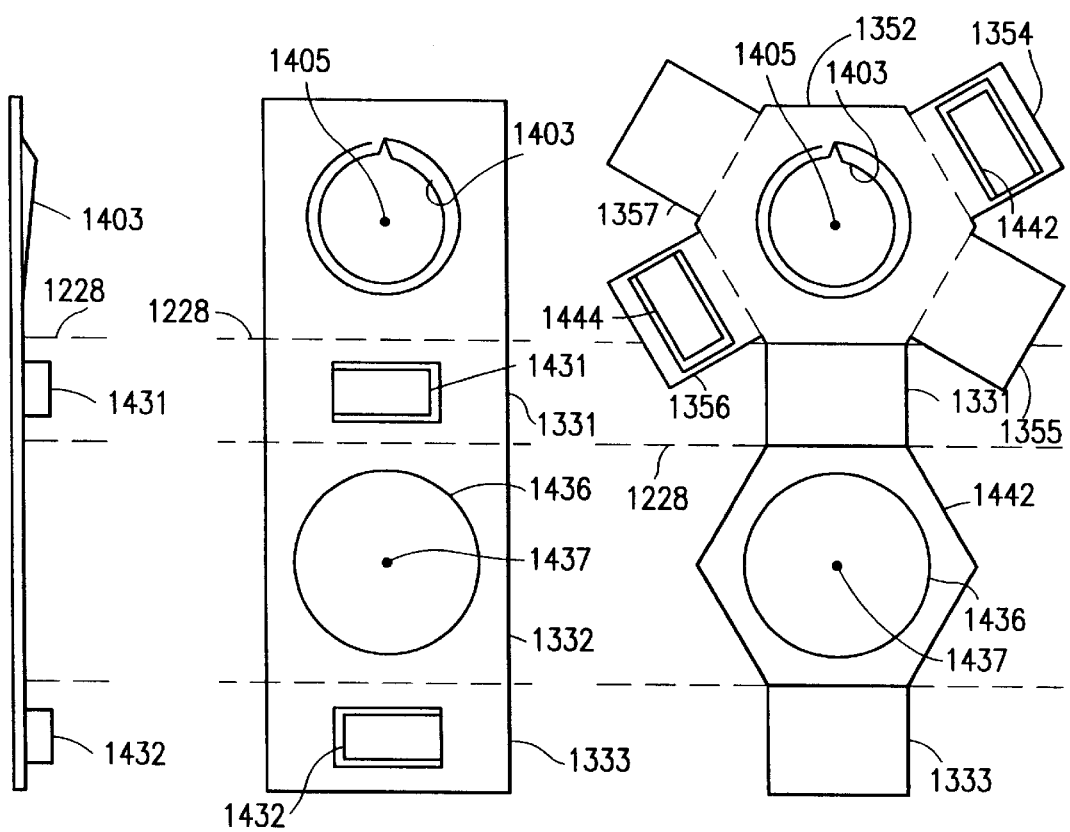

In FIGS. 35*p* and 35*q*, the same concept is carried forward. Partially manufactured sheet plate 1380 has a threaded bore 1372 with cutouts 1374. The cutouts accommodate tines 1348. In a final manufactured stage, fastener 1385 includes one or more tines 1348 which are disposed in cutouts 1374 in threaded bore 1372. The side plates protect the tines and add axial stability to the locking system.

FIGS. 35*r*–35*u* diagrammatically illustrate partial and final manufactured versions of fastener 1390. In FIG. 35*r* threaded bore 1372 includes a cutout 1374. However, rather than a cylindrical locking body as shown in FIG. 35*o*, a rectangular locking body 1391 carries at least one, and a preferably a plurality of tines 1348. In FIG. 35*s*, tine 1348 includes tine body 1392 and distal tine end 1393. Tine body 1392 is rotated with respect to the sheet plate along the dashed bend line and distal tine end section 1393 is bent along the dashed bend line. Distal tine end 1393 is positioned in cutout 1374 when the axial centerline 1345 of threaded barrel 1372 is coaxial with axial centerline 1350 of rectangular locking body 1391.

Figures 35T, 35V:
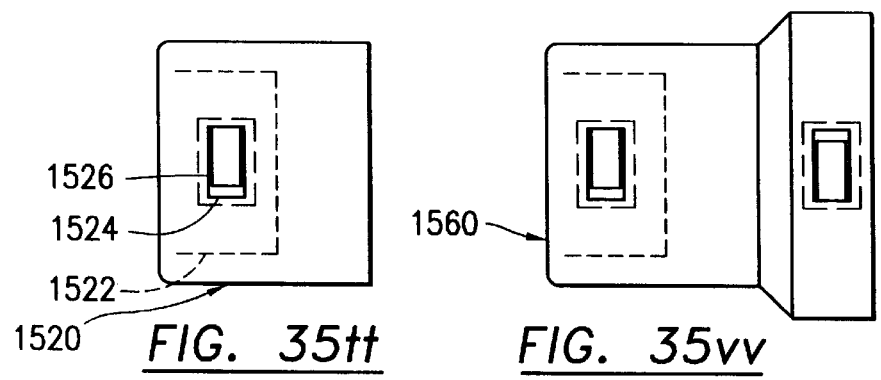
Figure 35U:
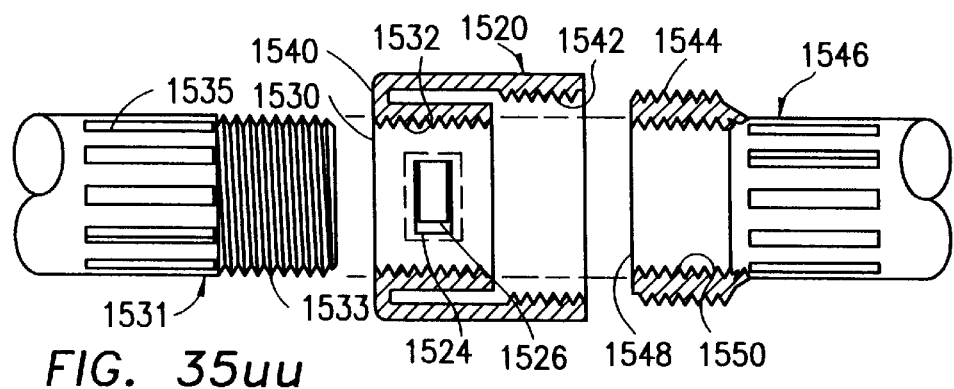
Figure 35W:
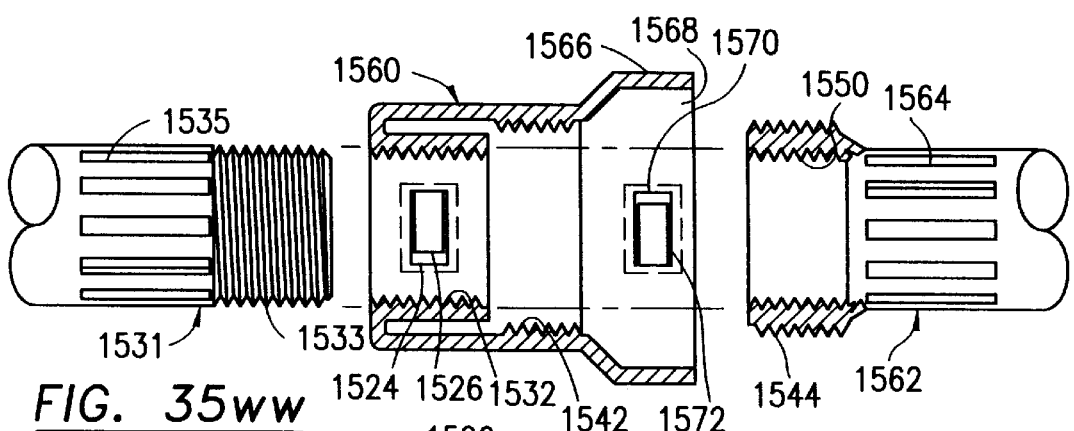

With respect to FIGS. 35*v* and 35*w*, those figures diagrammatically illustrate fastener 1395. Similar numerals designate similar items in FIGS. 35*r*–35*w*. Fastener 1395 includes tine 1393 mounted on rectangular locking body or structure 1391. In its fully manufactured state shown in FIG. 35*w*, tine 1393 is disposed in cutout 1374 of threaded barrel 1372.

Figure 35X:
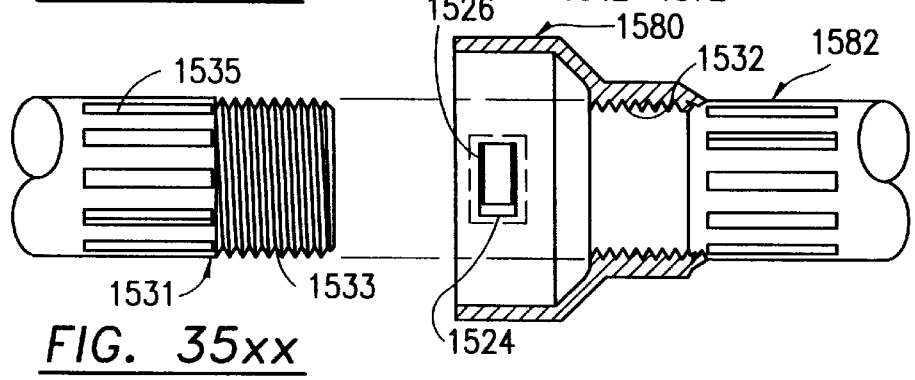

FIGS. 35*x*–35*aa* diagrammatically illustrate fastener 1401 having a single thread 1403 on plate section 1404. Single thread 1403 in FIG. 35*y* has a center point 1405. When the axial centerline 1350 of locking cylinder 1346 is place coaxial with respect to center point 1405 of single thread 1403, the finished fastener 1401 is created as shown in FIG. 35*aa*. FIG. 35*z* shows that single thread 1403 rises above the planar plate surface 1406. This enables the single thread to travel on the inclined plane of the threaded bolt operating on fastener 1401.

FIGS. 35*bb* and 35*cc* show a partial manufactured view and a final manufactured view of fastener 1410. When center point 1405 is made coaxial with respect to axial centerline 1350 of cylindrical locking cylinder 1346, tines 1378 protrude radially and tangentially into the axial centerline of fastener 1410. The operation of single thread 1403 is discussed in greater detail later in connection with FIGS. 47–50, among others.

FIGS. 35*dd*–35*gg* diagrammatically illustrate partial manufactured views and final manufactured views of fastener 1420. Fastener 1420 includes a single thread 1403 and a rectangular locking body or structure 1391 carrying at least one and preferably a plurality of tines 1393. Tines 1393 are distal end sections protruding from tine body 1348 and particular main tine body 1392. When center point 1405 of single thread 1403 is made coaxial with respect to axial centerline 1350, tines 1393 protrude radially and tangentially into the axial centerline of the entire fastener 1420.

FIGS. 35*hh* and 35*ii* also utilize a single thread 1430 and a rectangular tine carrying structure 1391 which supports a plurality of tine 1348. Particularly, distal tine end section 1393 projects tangentially and radially inwards towards the axial centerline of the entire fastener 1425. As discussed earlier, the channeled bolt moves longitudinally along the axial centerline.

FIGS. 35*jj*–35*mm* diagrammatically illustrate various stages of manufacture and the final version of fastener 1430. Fastener 1430 includes a single thread 1403 which cooperates with the bolt thread. Plate sections 1331 and 1333 are stamped out and tines 1431,1432 are formed in those plate sections. Plate section 1332 includes a through bore or hole 1436. Bore 1436 includes a center point 1437. When center point 1405 of single thread 1403 is coaxial with center point 1437 of bore 1436, the fastener 1430 has an axial centerline of 1435. Tines 1431 and 1432 extend tangentially and radially towards axial centerline 1435 of fastener 1430. The channeled bolt travels along the axial centerline of the fastener.

Fastener 1440 is diagrammatically illustrated in FIGS. 35*nn* and 35*oo*. In FIG. 35*nn*, plate section 1442 includes a through bore 1436. Bore 1436 includes a center point 1437. Further, side panels 1354 and 1356 have been punched out, stamped or tooled to create tines 1442, 1444. When fastener 1440 is bent along bend plane lines 1228 (perforated lines) and side faces 1354, 1355, 1356 and 1357 are placed perpendicular to end plate 1352, tines 1442, 1444 protrude radially and tangentially through and towards the axial centerline of fastener 1440. The axial centerline of fastener 1440 passes through center point 1405 of single thread 1403 and center point 1437 of through bore 1436.

FIGS. 35*pp*–35*ss* diagrammatically illustrate a locking drawn barrel 1500. Locking drawn barrel 1500 in FIG. 35*qq* includes an axially inboard radial lip 1502. In contrast, the thread carrying cylinder 1504 for locking barrel 1500 in FIG. 35*pp* does not include an axially inboard, radial lip. Both drawn barrels include a cylindrical locking structure 1506 from which tangentially and radially extends tine 1510. A plurality of tines may be utilized to increase the clamping factor of the fastener system.

FIG. 35*rr* shows locking barrel 1500 mounted in a recess in nut 1511. Tines 1510 are shown extending tangentially and radially toward the axial centerline of the composite locking barrel 1500 and nut 1511. The term "composite" refers to the insert and nut combination. Threads 1512 are disposed axially inboard on thread barrel 1504.

FIG. 35*ss* shows thread barrel cylinder 1504, locking cylindrical structure 1506 and tine 1510.

Lip 1502 in FIG. 35*qq* helps lock the extrusion into a plastic or composite nut body. This locking feature is an important feature of the present design because the locking drawn barrel 1500 can be mass assembled. Further, this feature may enable a composite nut/locking structure to be cheaply manufactured while maintaining the strength of the locking structure in the nut insert and the lightness of the system by using a plastic nut body. Hence, the term "composite" is appropriate for a plastic nut and a metal nut insert as described in FIGS. 35*pp*–35*ss*.

FIGS. 35*tt*–35*xx* diagrammatically illustrate a double reverse extrusion (FIG. 35*tt*) which can be further utilized as a pipe lock (FIGS. 35*tt*–35*xx*). The locking nut or fastener may be utilized in conjunction with a threaded pipe or rod in order to provide a locking mechanism for the pipe or rod. If the outside of a flanged female pipe (or possibly a standard female pipe) is threaded, the lock of the present invention can be threaded onto the pipe and the locking engagements may drop into axial grooves on the outside of the male end of the pipe. Threads may not be necessary under the grooves on the male side of the pipe.

FIG. 35*tt* shows a cylindrical body 1520 carrying, in an internal region, a threaded bore 1522. Threaded bore 1522 includes a cutout 1524 through which protrudes a tine 1526. The tine may be supported by a further internal body in body 1520.

FIG. 35*uu* shows a diagrammatic, cross-sectional view of cylindrical structure 1520. Structure 1520 has an open end 1530 into which pipe 1531 is inserted. Pipe 1531 includes threads 1533 and axial grooves 1535. Threads 1533 are complementary to female threads 1532 disposed on the interior of cylindrical structure 1520. Threaded bore 1532 has a cutout 1524 and a tine 1526 extends there through. If cylindrical structure 1520 were truncated at face 1540, the structure would define a smaller cylindrical structure and operate to lock on to and cap pipe 1531. Of course, rather than utilizing a pipe 1531 any type of cylindrical item or rod carrying threads 1533 and axial grooves 1531 could be locked onto cylindrical structure 1520.

In the absence of a truncation at face 1540, the locking joint shown in FIG. 35*uu* includes a second set of female threads 1542 which is complimentary to male threads 1544 on pipe 1546. Further, pipe end 1548 includes internal female threads 1550. Internal female threads 1550 enable male threads 1533 on pipe 1531 to be fully inserted and ride not only on female threads 1532 of cylindrical unit 1520 but also on pipe 1546.

The structure illustrated in FIG. 35*uu* enables the user to lock on the cylindrical unit 1520 while being able to disassemble or withdraw pipe 1546 from lock unit 1520.

Similar numerals designate similar items and are carried forward into FIGS. 35*ww*, 35*vv* and 35*xx*.

FIG. 35*ww* diagrammatically illustrates pipe lock or coupler 1560. FIG. 35*vv* diagrammatically illustrates the outside appearance of pipe lock 1560. Pipe lock 1560 includes, on its left hand side, a similar pipe lock as described above in connection with FIG. 35*uu*. On the right hand side, pipe lock 1560 includes female threads 1542 which are complimentary to male threads 1544 on pipe 1562. Pipe 1562 includes axial grooves or cutouts 1564. Pipe 1562 also may include internal female threads 1550 in a manner similar to the pipe lock shown in FIG. 35*uu*. Further, pipe lock 1560 includes a larger diameter section 1566. The internal wall 1568 of larger diameter section 1566 includes a cutout 1570. A tine 1572 extends through the cutout and coacts with axial grooves 1564 of pipe 1562. Accordingly, the user may lock pipe 1531 on the left hand side of coupler 1560. The user may subsequently lock pipe 1562 on the right hand side of pipe lock 1560.

FIG. 35*xx* shows a modified pipe lock 1580 disposed at a terminal end of pipe 1582. Female threads 1532 have been moved axially inboard away from tine 1526. Accordingly, male threads 1533 of pipe 1531 can be mounted on female threaded coupling 1532. Accordingly, tine 1526 pops into and out of the grooves 1535 on pipe 1531 thereby locking the pipe onto the terminal end of pipe 1582.

FIG. 36 diagrammatically illustrates an S-shaped locking nut and bolt assembly 270. All illustrations of the clips are expanded to better show the critical features of the invention. The S-shaped member includes legs 271, 272 and 273. It is important to remember that leg 271 may be truncated at any location above line 274 thereby eliminating the leg portion toward terminal end 275. As used herein, "S-shaped" refers to the S-shape shown in FIG. 36 or a truncated S-shape which eliminates all or a portion of the segment from line 274 to terminal end 275 of leg 271.

Leg 272 includes a nut formed as cylindrical unit 276. On leg 273, an elongated locking unit 277 is formed. In view of the length of leg 271, that leg also has a bore 278. The axial centerline through bore 278 and nut 276 and cylindrical locking unit 277 is coaxial. As shown in FIG. 37, panel 280 includes a panel bore 282. The panel bore is coaxial with clip leg bore 278, nut 276 and cylindrical locking unit 277. A bolt similar to that described above in connection with FIGS. 25*a* and 25b is inserted through bore 278, 282 and threaded through nut 276 and ultimately locking onto cylindrical locking unit 277.

Cylindrical locking unit 277 includes at least one, and in the illustrated embodiment, a plurality of tines, one of which is tine 282. In a preferred embodiment, tine 282 is established by cutting out a region 283 from the cylindrical locking unit 277. As discussed earlier, tine 282 has a distal tine end which tangentially and radially protrudes inward toward the cylindrical axis of the specially configured bolt. When the tine end abuts a locking face (for example, locking face 236 in FIG. 24 for bolt 231), the tine and the locking face prevent counter-rotational movement of the bolt with respect to the locking nut and bolt clip assembly 270. Otherwise, when the bolt is moved in a rotational manner, the distal tine end rides on opposing slope 237 and bolt thread crest 234 and further rotational movement is permitted.

Cylindrical locking unit 277 has a cylindrical axis perpendicular to the plane of leg 273. As shown with respect to FIG. 42, cylindrical locking unit 277 may be disposed on intermediate leg 272 and nut 276 may be disposed on laterally distant leg 273.

FIG. 37 shows that bored panel 280 is placed between clip leg 271 and clip leg 272 of S-shaped clip 270 such that bore 278 is coaxial with panel bore 282 and the nut thread 285 of nut 276. Cylindrical locking unit 277 is also coaxial with this bolt passageway. The locking action of tine 282 is visibly confirmed since tine 282 is disposed in cut-out 283.

FIG. 38a shows an S-shaped locking nut and bolt clip assembly having an S-shaped clip 290 and clip legs 291, 292 and 293. Clip leg 291 includes bore 294 since the terminal end 295 of that leg extends above nut thread 296 of nut 297. S-shaped clip 290 is adapted to be slid or placed, as shown by arrow 298, onto panel 299. Panel 299 includes bore 301. Bore 301 is placed coaxially with respect to bore 294 and nut thread 296 of nut 297.

A locking element is configured or formed on leg 293. This locking element includes a plurality of perpendicular panels 303, 304, 305 and 306. These panels are perpendicular to the generally planar surface of clip leg 293. More importantly, these panels 303, 304, 305 and 306 define axially protruding legs which are perpendicular to clip leg 293 and, more importantly, are tangentially disposed with respect to an axial centerline passing through bore 294 and nut 297. As such, the locking element forms a locking element bore 307 through which protrudes the specially configured bolt. See FIGS. 25a, 25b. Each axially protruding leg 303, 304, 305 and 306 also includes a respective tine 310, 311, 312 and 314. These tines protrude tangentially and radially toward the axial centerline defined by bore 294, nut thread 296 and locking element bore 307. As discussed in detail earlier, each tine has a distal tine end adapted to latch onto a lock face of one or more notches in a specially configured bolt. See bolt segment 11, 13 in FIGS. 25a, 25b, and particularly longitudinal locking channel 9 and spiral locking channel 7. Each tine also includes a proximal tine portion attached to the corresponding axially protruding leg 303, 304, 305 and 306. When the specially configured bolt is inserted through bore 294, bore 282 in panel 280 (FIG. 37), and threaded onto nut thread 296 of nut 297, and further when the locking channels pass tines 310, 311, 312 and 314, the position of each distal tine end is visible to the user. This visibility is provided not only by the cut-outs defined adjacent each tine 310, 311, 312 and 314 but also because of the tangential orientation of the small axially protruding leg segments 303, 304, 305 and 306.

FIG. 38b shows a manufacturing stage for the locking element formed by the plurality of axially protruding legs 303, 304, 305 and 306 in FIG. 38a. In FIG. 38b, clip leg segment 293 is generally planar and locking leg segments 303', 304', 305' and 306' have been formed by stamping, cutting or otherwise forming leg segments on clip leg segment 293. Each axially protruding leg segment clearly defines the distal tine end and proximal tine portion. For example, with respect to locking leg segment 303', distal tine end 310' is identified. Proximal tine portion 316 is immediately adjacent protruding leg segment 303'. Accordingly, in order to form axially protruding legs 303, 304, 305 and 306 as shown in FIG. 38a, leg segments 303', 304', 305' and 306' are rotated out of the plane formed by clip leg segment 293. Thereafter, the distal tine portions 310, 311, 312 and 314 are pressed radially inward toward the axial centerline running through bore 294 and nut thread 296.

Figure 39:
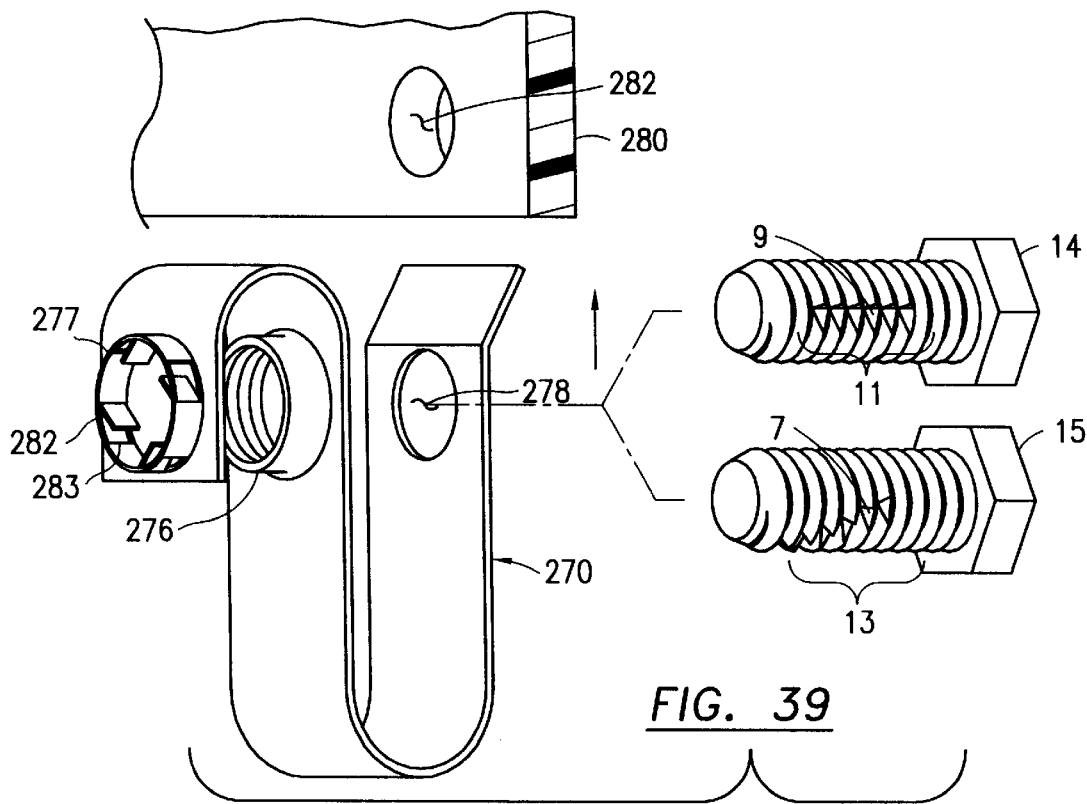
FIG. 39 diagrammatically illustrates the S-shaped clip utilized in conjunction with a bolt having a longitudinal locking channel and a bolt having a spiral locking channel and a panel having a bore.

FIG. 39 diagrammatically illustrates that S-shaped clip 270 can be utilized in conjunction with bolt 14 carrying longitudinal locking channel 9 on bolt thread segment 11 or bolt 15, carrying spiral locking channel 7 on bolt thread segment 13. Either one of these specially configured bolts can be threaded through bore 278 after S-shaped clip 270 is placed onto panel 280 such that bore 278 is coaxial with panel bore 282. Bolts 14, 15 threaded through bores 278, 282 and threaded onto nut 276 ultimately engage cylindrical locking unit 277. Distal tine ends 282 visibly engage locking channels 7, 9 due to the tine's position in cut-out 283. Also, the axially extending nature of the locking unit enhances visibility.

Figure 40:
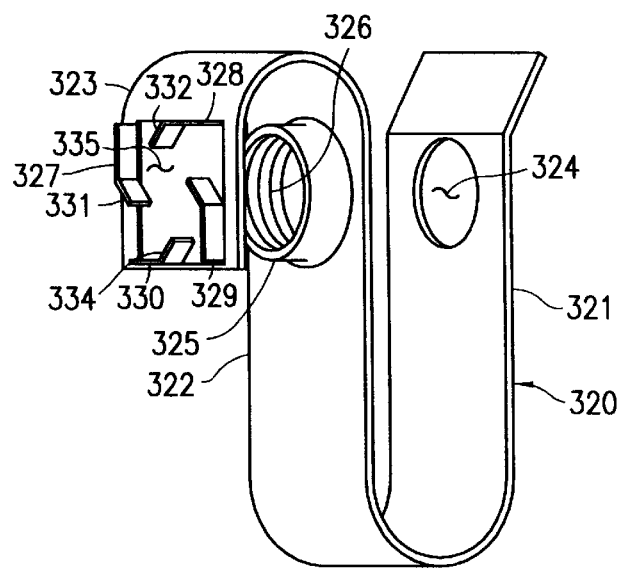
FIG. 40 diagrammatically illustrates an S-shaped clip having a locking element with a plurality of axially protruding legs formed on one clip leg.

FIG. 40 diagrammatically shows S-shaped clip 320 having clip legs 321, 322 and 323. Clip leg 321 defines bore 324. Clip leg 322 carries nut 325 having nut thread 326 thereon. Clip leg 323 carries a locking element formed of a plurality of axially protruding legs 327, 328, 329 and 330. Each axially protruding leg includes a distal tine end 331, 332, 333 and 334. Additionally, the locking element establishes a locking element bore 335. These tines are not cut-out from the locking element legs but are simply angularly offset with respect to the legs. It should be noted that clip legs 321, 322, 323 may be bent inward towards nut thread 326 rather than outboard away from the thread. This will protect the integrity of the tines, i.e., limit damage during shipping and installation. Also, the terminal end of clip leg 323 may include a depending spacer leg as shown in FIG. 43, leg 362.

Figure 41A:
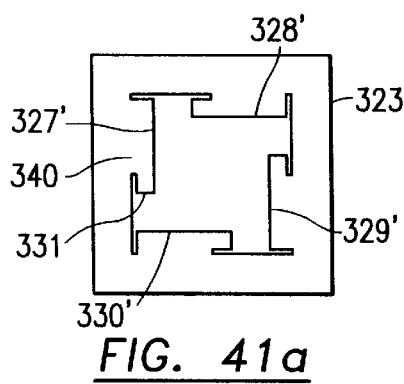
Figure 41B:
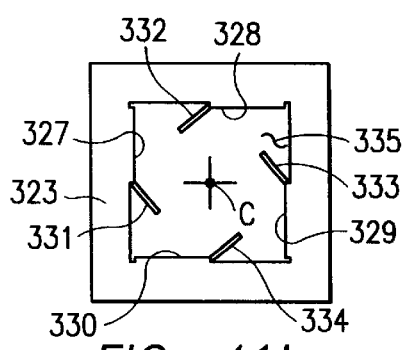

FIGS. 41a and 41b show various manufacturing stages for the locking element. Clip leg segment 323 in FIG. 41a shows that protruding leg segments 327', 328', 329' and 330' are stamped or cut from a generally planar sheet of metal or plastic. Each protruding leg segment clearly defines a distal tine end, for example distal tine end 331 for leg 327' is identified in FIG. 41a. Further, leg segment 327' also establishes proximal tine portion 340. In order to form the locking element shown in FIG. 40, protruding leg segments 327', 328', 329' and 330' are rotated out of the plane formed by clip leg segment 323. FIG. 41b shows a front view of clip leg segment 323. Axially protruding legs 327, 328, 329 and 330 are normal to the plane established by clip leg segment 323. Distal tine ends 331, 332, 333 and 334 protrude tangentially and radially inward toward the axially centerline C in locking element bore 335.

Figure 42:
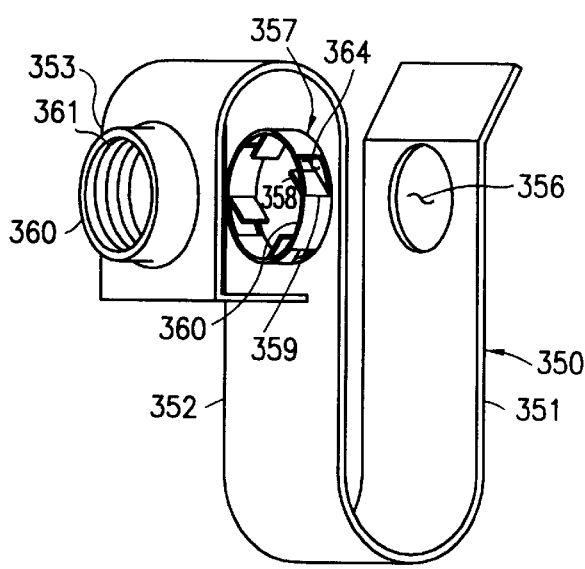

FIG. 42 diagrammatically illustrates S-shaped clip 350 having clip legs 351, 352 and 353. As shown in FIG. 43, S-shaped clip 350 is placed on bored panel 354 as shown by arrow 355. Clip leg 351 includes a bore 356. Clip leg 352 includes a cylindrical locking unit 357. Cylindrical locking unit 357 has a plurality of circumferentially spaced apart tines, one of which is distal tine end 358. Alternatively, cylindrical locking unit 357 may include only a single tine. Distal tine end 358 has a proximal tine portion 359 adjacent cylindrical body 360 of cylindrical locking unit 357. Clip leg 353 includes nut 360 having nut threads 361 thereat. Nut 360 is coaxial with cylindrical locking unit 357 and bore 356.

Figure 43:
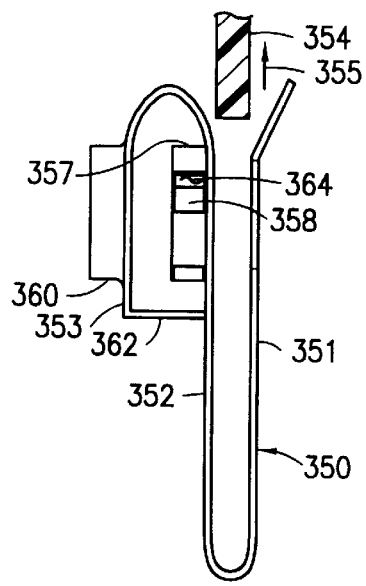
FIGS. 42 and 43 diagrammatically illustrate an S-shaped clip and locking nut and bolt assembly wherein one clip leg carries a cylindrical locking unit.

As shown in FIG. 43, clip leg 353 includes depending spacer leg 362. FIG. 43 also shows that distal tine end 358 is visible during locking and unlocking due to cut-out 364. Basically, the distal tine end 358 moves into and out of one or more notches forming longitudinal locking channel 9 (FIG. 25*a*) or spiral locking channel 7 (FIG. 25*b*). The depending spacer leg 362 ensures that when the bolt segment 11, 13 (FIGS. 25*a*, 25*b*) are threaded onto thread 361, nut 360 maintains its coaxial position with respect to the axial centerline of the bolt. In other words, when the bolt pulls clip legs 351, 352 and 353 together, the coaxial nature of nut 360 with respect to the axial centerline of the bolt is maintained due to depending spacing leg 362.

Figure 44:
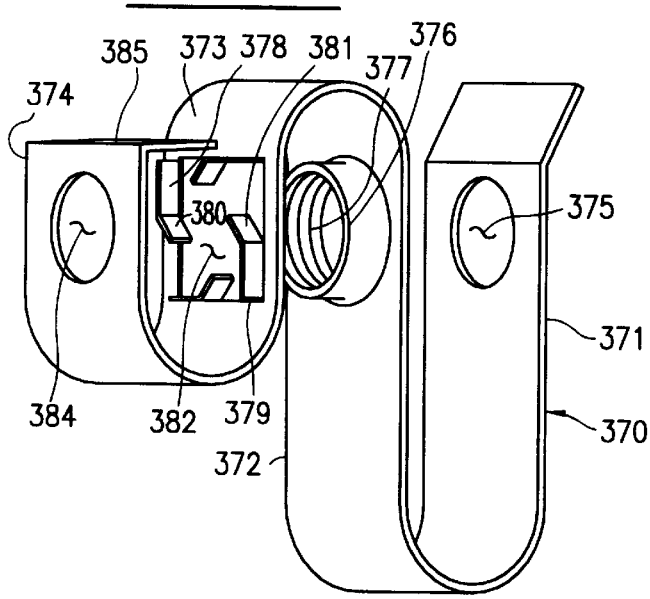

FIG. 44 diagrammatically illustrates S-shaped clip 370 having clip legs 371, 372, 373 and a fourth clip leg 374. Clip leg 371 includes bore 375. Clip leg 372 includes a nut 376 having a nut thread 377. Clip leg 373 includes a locking element formed of a plurality of axially protruding legs, two of which are axially protruding legs 378, 379. Each axially protruding leg includes a distal tine end 380 and 381 which extends tangentially and radially inward toward the axial centerline formed by bore 375, nut thread 377 and nut 376 and the locking element bore 382. In the illustrated embodiment, another pair of opposing axially protruding legs is formed on clip leg 373. Clip leg 374 includes a supplemental bore 384. Supplemental leg 374 includes a depending spacer leg 385.

Figure 45B:
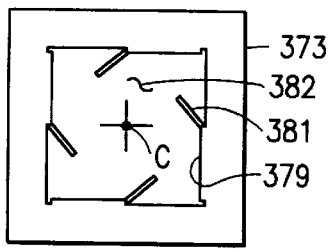
FIGS. 44, 45a, 45b and 46a diagrammatically illustrate an S-shaped clip wherein one clip leg carries a locking element having a plurality of axially protruding legs, diagrammatically shows various stages of manufacture of the locking element and diagrammatically shows a side view of the S-shaped clip with the bored panel.
Figure 45A:
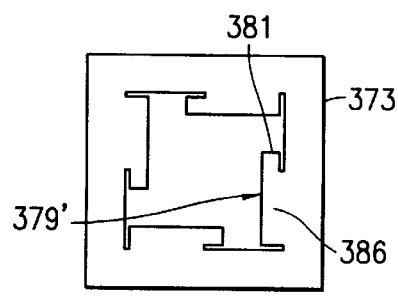

FIGS. 45*a* and 45*b* illustrate various manufacturing stages for the axially protruding legs. Clip leg segment 373 is stamped or pressed or cut to form a number of locking leg segments, one of which is segment 379'. Leg segment 379' includes a distal tine end 381 and a proximal tine portion 386. Proximal tine portion 386 is adjacent clip leg segment 373. In FIG. 45*b*, protruding leg segment 379' (FIG. 45*a*) is rotated out of the plane formed by clip leg segment 373 to form axially protruding leg 379. In order to form the distal tine end 381, the tine end is pressed radially inward toward centerline C of locking element bore 392.

Figure 46A:
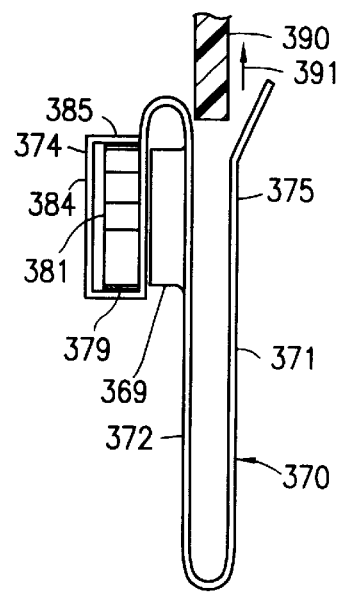

FIG. 46*a* diagrammatically illustrates a side view of S-shaped clip 370 being placed on bored panel 390 in the direction shown by arrow 391. FIG. 46*a* also shows that bore 375 in clip leg 371 is coaxial with nut 376 on clip leg 372 and the locking element formed by axially protruding legs 379 and distal tine end 381. Bore 384 on leg 374 is also coaxial with bore 375 on leg 371. Depending leg 385 spaces supplemental leg 374 away from locking element formed by axially protruding legs 379. In this configuration, supplemental clip leg 374 and depending spacing leg 385 protect the axially protruding nature of legs 379 and 378. Supplemental clip leg 374 also protects the radially protruding nature of distal tine ends 381.

Figure 46B:
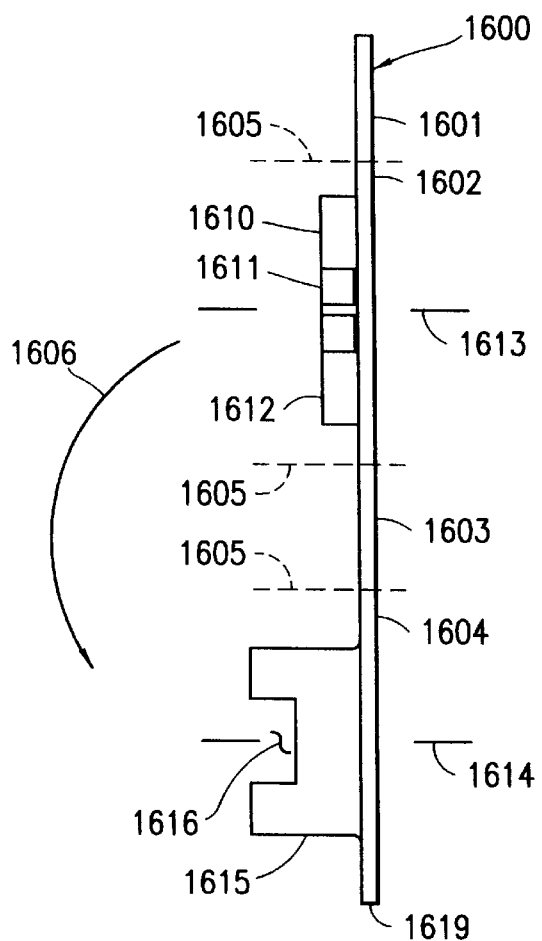
FIGS. 46b–46g diagrammatically illustrate various clip locks, clip fasteners or nuts which may be configured as separate locking nuts or fasteners (see FIGS. 46f and 46h) or may be disposed on a leg of a U, J or S-shaped clip.
Figure 46C:
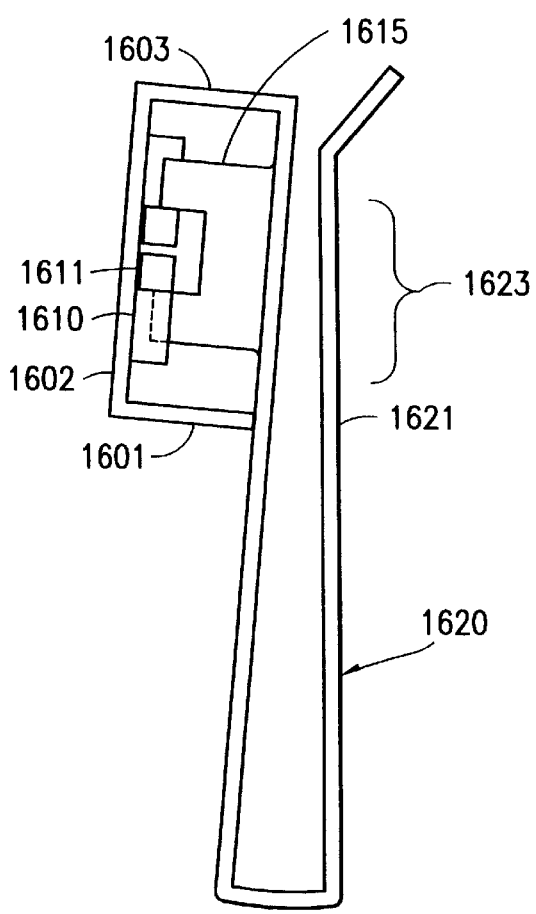
Figure 46F:
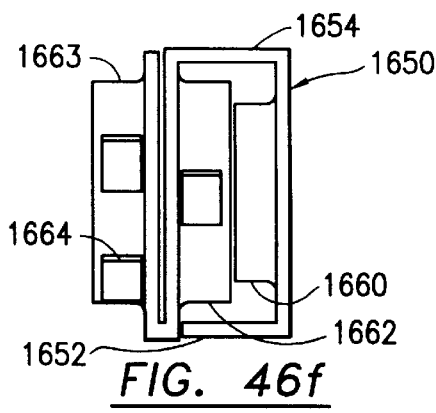
Figure 46G:
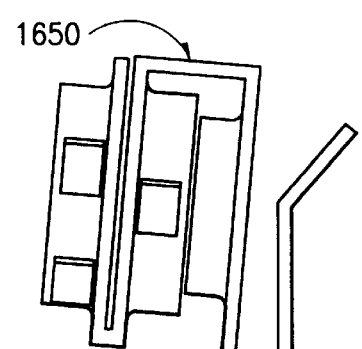
Figure 46D:
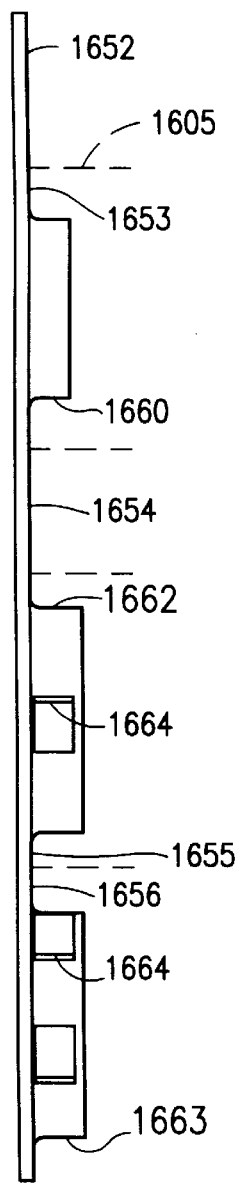
Figure 46E:
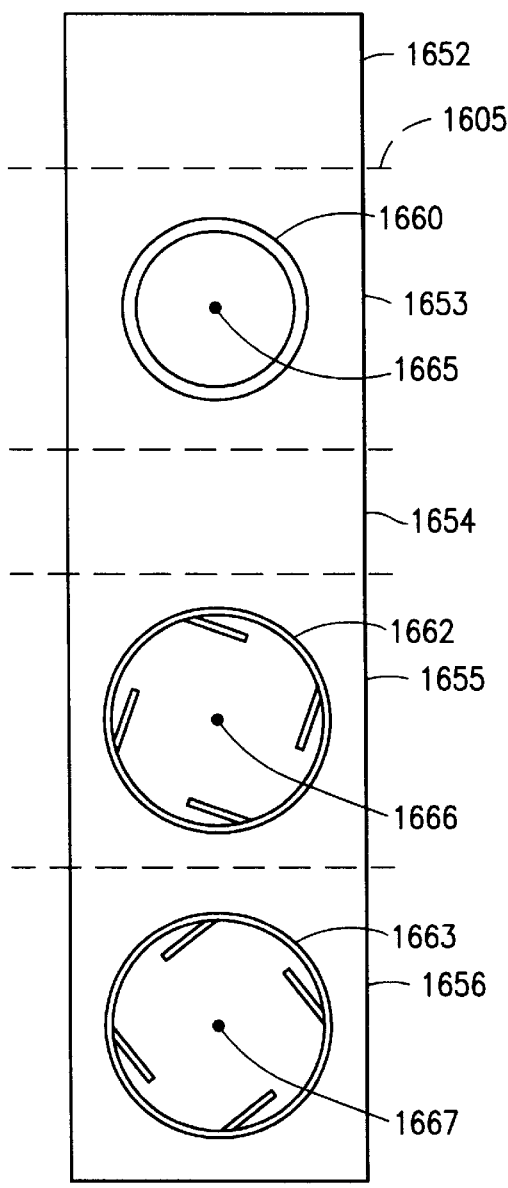
Figures 46H, 46I, 46J:
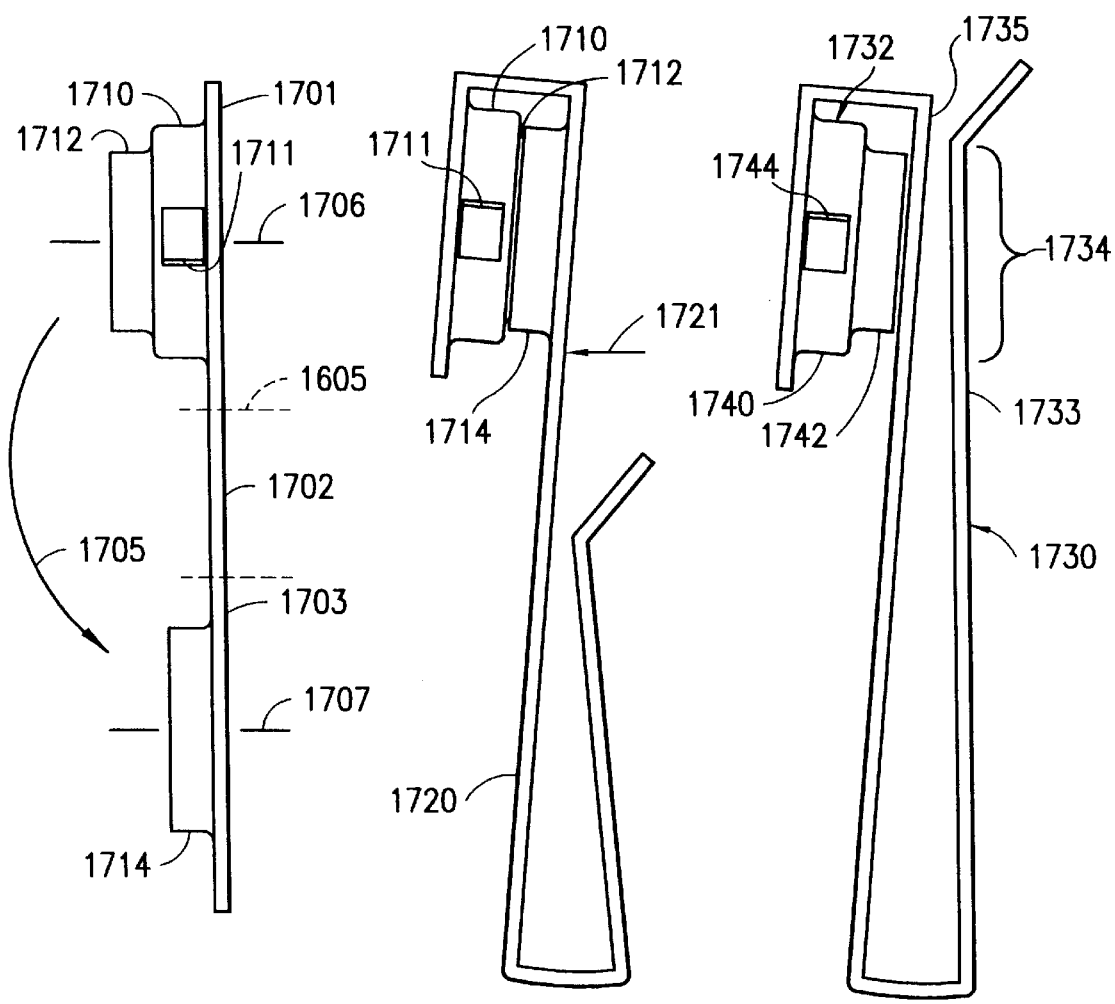
FIGS. 46h–46j diagrammatically illustrate a locking mechanism with the threaded nut barrel disposed on a axial end of a cylindrical, tine carrying locking unit or structure.

FIGS. 46*b*–46*j* diagrammatically illustrate another embodiment of fastener clips or fastener nuts. FIG. 46*b* shows partially manufactured plate 1600 having plate segments 1601, 1602, 1603 and 1604. These various plate segments are bent along bend lines 1605 as shown by arrow 1606. Plate section 1602 includes axially extending structures 1610 and 1612. These structures carry tines 1611. Plate section 1604 carries a threaded barrel 1615. Threaded barrel 1615 has a cutout 1616. The barrel is extruded or is otherwise formed on the plate. Thereafter the cylindrical shaped body is threaded.

FIG. 46*c* shows a U-clip 1620. It should be noted that when the axial centerline 1613 of tine carrying structures 1610, 1612 is made coaxial with the axially centerline 1614 of threaded barrel 1615 (by bending and forming the structure), a single nut or fastener is created. Further, the fastener made in accordance with FIG. 46*b* may include a U-clip, J-clip or an S-shaped clip attached to end 1619. Hence, the fastener may be a stand alone unit or may be part of a U, J or S-shaped clip system.

FIG. 46*c* shows the rolled up fastener or nut. Similar numerals designate similar items in FIGS. 46*b*–46*j*. Of course, clip leg 1621 includes a through bore at region 1623 in order to permit the specially configured bolt or pipe or other rod-like structure to pass through and to activate the locking mechanism created by tines 1611.

FIGS. 46*f*–46*g* diagrammatically illustrate another type of nut or fastener 1650. In FIG. 46*f*, fastener 1650 stands alone. In FIG. 46*g*, fastener 1650 is attached to a U-shaped clip 1651. Of course, U-clip 1651 may be a J-shaped clip or may be a S-shaped clip.

In FIG. 46*d*, clip 1650 is created by utilizing a sheet metal plate having sections 1652, 1653, 1654, 1655 and 1656. Bend planes 1605 are shown in FIGS. 46*d* and 46*e*. Axial stability is enhanced by the axial "stacking" of these structures.

A threaded bore 1660 is extruded from section 1653. A cylindrical locking structure 1662 is extruded from sections 1655 and 1656. Tines 1664 are stamped or cut from cylindrical locking cylinders 1662, 1663. The plate is bent such that axial centerline 1665 of threaded bore 1660 is coaxial with the axial centerline 1666 of cylindrical locking structure 1662. Further, the axial centerline 1667 of cylindrical locking structure 1663 is also made coaxial with the other axial center lines 1665 and 1666. The resulting structure for fastener or nut 1650 is illustrated in FIG. 46*f*.

FIG. 46*g* shows that fastener 1650 can be mounted on U, J or S-shaped clips. In FIG. 46*g*, U-shaped clip 1651 is utilized.

Fastener 1650 in FIG. 46*f* is partially protected by depending end wall 1652 and the opposing joining wall 1654. Wall 1652 provides additional axial support. Further, multiple cylindrical (or rectangular) structures may be added to additional plate sections. Rectangular tine supporting structures are discussed above in connection with FIGS. 35*dd*–35*ii*, among others.

FIGS. 46*h*–46*j* diagrammatically illustrate additional locking fasteners. In FIG. 46*h*, the metal plate is divided into section 1701, 1702 and 1703. Bend planes 1605 are shown in dashed lines. The fastener is created by rotating plate 1701 in the direction shown by arrow 1705 such that axial centerline 1706 is coaxial with axial centerline 1707.

The fastener includes a cylindrical tine carrying support 1710 and a threaded barrel 1712 at an axial end of the cylindrical support 1710. Support 1710 has one or more tines 1711 stamped, tooled or created in its cylindrical wall. Plate section 1703 includes an extruded guide cylinder 1714.

As shown in FIG. 46*i*, guide cylinder 1714 captures threaded barrel 1712 in its interior. Cylindrical locking structure 1710 provides support for locking tine 1711. Of course, a single fastener may be created by truncating J-shaped clip 1720 at point shown by arrow 1721. The axial capture of the thread barrel greatly enhances stability and clamping forces.

FIG. 46j diagrammatically illustrates a U-shaped clip 1730 carrying a fastener 1732 at one end thereof. Clip leg 1733 will include a through bore at region 1734. Clip leg 1735 will include a similar through bore coaxial with through bore 1734. Fastener 1732 includes a cylindrical or a rectangular tine carrying structure 1740 and an threaded bore 1742 adjacent thereto. Tines 1744 provide locking for fastener structure 1732.

FIG. 47 diagrammatically illustrates a U-shaped clip 400 which is adapted to be placed onto a bored panel 401 as shown by arrow 402. Panel 401 includes a bore 403 there through. U-shaped clip 400 includes clip leg 404 and clip leg 405. Clip leg 404 has a single thread nut 406 thereon. The single thread nut 406 has an arc less than 360°. In the illustrated embodiment, the arc of single thread nut is approximately 350°. The single thread nut, shown in a partial, broken away view in FIG. 48, is formed by cutting or stamping a strip 407 from clip leg 404. Strip 407 remains attached to clip leg 404 via region 410.

A locking element is formed on clip leg 405. See FIG. 47. The locking element includes a plurality of axially protruding legs 412, 413, 414 and 415. Each axially protruding leg includes a corresponding tine 416, 417, 418 and 419. The distal tine ends 416, 417, 418 and 419 protrude tangentially and radially inward toward the axial centerline C of locking element bore 420. Axial centerline C is coaxial with the axial centerline through single thread nut 106. This axial centerline is also normal or perpendicular to planar clip legs 404 and 405. As explained earlier in connection with FIGS. 40 and 44, the distal tine ends 416,417,418 and 419 latch onto the lock face 36 FIG. 1b) of either a longitudinal locking channel 9 in bolt segment 11 (FIG. 25a) or a spiral locking channel 7 for bolt segment 13 (FIG. 25b). When the distal tine ends abut lock face 36 (FIG. 1b) counter-rotational movement is prohibited. Otherwise, during rotational movement, the distal tine ends 416, 417, 418 and 419 ride on opposing slope 38 and bolt thread crest 30.

FIG. 50 shows bolts 14, 15 carrying longitudinal locking channel 9 and spiral locking channel 7, respectively, adapted to be fed into single thread nut 406 on clip leg 404. Clip leg 405 is truncated since that clip leg may carry a cylindrical locking unit (FIG. 49) or a locking element with axially protruding legs.

FIG. 49 diagrammatically illustrates a U-shaped clip 420 having clip leg 404 and a second clip leg 421. A single thread nut 406 having an arc less than 360° is formed on clip leg 404. On clip leg 421, a cylindrical locking unit 422 is formed. Cylindrical locking unit 422 includes a plurality of tines extending tangentially and radially inward toward the cylindrical axis of cylindrical locking unit 422 which is coaxial to the axis of single thread nut 406. Cylindrical locking unit 422 may utilize a single tine 423 having a proximal tine portion 424 extending from cylinder 425. Distal tine end 423 is cut-out from cut-out 426 of cylinder 425. Accordingly, the user can easily identify whether distal tine end 423 has fallen into spiral locking channel 7 (FIG. 50) or longitudinal locking channel 9 (FIG. 50). In a like manner, distal tine ends 416, 417, 418 and 419 (FIG. 47) can be viewed by an observer in order to determine whether the distal tine ends have fallen into spiral locking channel 7 (FIG. 50) or longitudinal locking channel 9 (FIG. 50).

FIG. 51 diagrammatically illustrates U-shaped clip 430 having a clip leg 431 and clip leg 432. A bore 433 is defined at an upper region 434 of clip leg 431. If upper region 434 is eliminated or truncated, a J-shaped clip is provided. See FIG. 55.

Clip leg 432 also defines a single thread nut 436. Single thread nut has an arc less than 360° and the axial centerline of single thread nut 436 is coaxial with bore 433. A locking element 438 is defined on nut bore 437. Locking element 438 includes an axially protruding leg 439 and a tine 440 protruding tangentially and radially inward toward the axial centerline of nut bore 437 which is coaxial with bore 433. In the illustrated embodiment, the single thread nut 436 defines an arc of about 2250°. Leg 439 is disposed beyond the arc of the nut thread.

FIGS. 52a and 52b diagrammatically illustrate U-shaped clip 430 and J-shaped clip 450. FIG. 52a shows U-shaped clip 430 with the axial extending leg 439 of locking element 438 directed radially inward. Axially extending leg 439 is perpendicular to the plane of clip leg 432. Tine 440 protrudes tangentially and radially inward toward the axial centerline generally located at imaginary line 441. A panel 442 having a bore 443 is used in connection with U-shaped clip 430. Clip 430 is placed on panel 442 as shown by arrow 444. In operation, U-shaped clip 430 is placed on bored panel 442 such that the axial centerline 441 for the apertures in clip 430 is coaxial with bore 443. Thereafter, one of the specially configured bolts shown in FIGS. 53a and 53b can be inserted along axial centerline 441. Bolt 14 has a longitudinal locking channel 9 along bolt thread segment 11. Bolt 15 includes spiral locking channel 7 along bolt thread segment 13. When tine 440 falls in one or more of the notches in bolt segments 11, 13, the distal end of the tine, when it abuts the locking face of the notch (see lock face 36 in FIG. 1b), prevents counter-rotational movement. Otherwise during rotational movement, the distal tine end moves on opposing slope 38 (FIG. 1b) and rides atop bolt thread crest 30.

FIG. 52b diagrammatically illustrates a J-shaped clip 450 which is placed on panel 451 as shown by arrow 452. Panel 451 includes bore 453. Bore 453, when clip 450 is place thereon is coaxial with the axial centerline 454 of the locking element nut bore.

FIG. 55 diagrammatically illustrates J-shaped clip 450 having a first leg 455 and a second clip leg 456. A single thread nut 457 is defined on clip leg 456. The single thread nut 457 includes an arc less than 360° and, in the illustrated embodiment, an arc spanning approximately 225°. The single thread nut also is utilized in cooperation with a locking element 458. Locking element 458 includes an axial protruding leg 459 and a distal tine end 460. Axially protruding leg 459 is best illustrated in FIG. 52b. Leg 459 is perpendicular to clip leg 456. Distal tine end 460 extends tangentially and radially inward toward axial centerline 454 of the nut bore. Locking element bore 461 is shown in FIG. 55. The locking element is formed at a radially inward edge of the locking element bore. The locking element bore in this embodiment is identical to the nut bore.

It should be noted that although panels 442, 451 in the figures are shown as being made of insulated material, those panels may be wood, plastic, metal or any other type of composite panel. Also, when used herein, the term U-shaped clip also includes the J-shaped clip construction. A J-shaped clip is simply a U-shaped clip with a certain portion of a terminal end of a clip leg truncated. For example, U-shaped clip 430 FIG. 51 can be converted into a J-shaped clip simply by truncating segment 434.

As in FIG. 55, locking element 458 is formed on nut bore 461 at a point beyond the arc of the single thread nut 457.

FIGS. 54a and 54b illustrate various stages of manufacture for the locking element. Clip leg segment 456 includes a locking element segment 458'. Locking element segment 458' shows a distal clip end segment 460', a leg segment 459' and a proximal tine segment 463. In order to further relieve stress, clip leg 456 may include a stress cut or slice at a 45 degree angle on the right side of proximal tine segment 463. Also, rather than the "squared" cut defining the right side of segment 458', the cut or slice may be at a 45 degree angle.

In FIG. 54b, clip leg segment 456 has been further cut, stamped or otherwise configured to establish single thread nut 457 with the locking element 458 on the nut bore. Axially protruding leg 459 has been formed by bending leg 459 out of the plane established by clip leg 456. Distal tine end 460 has been formed by bending the tine leg radially inward toward nut bore 461 away from the plane of axial leg 459.

FIG. 56a shows a J-clip 470 having a truncated clip leg 471 and a second clip leg 472. Clip leg 472 has a nut bore 473 and a single thread nut 474. Single thread nut 474 includes nut segments 475, 476 and 477. These nut thread segments define arcuate regions around the nut thread bore 473.

In addition, clip leg 472 includes a locking element consisting of axially protruding legs 480 and 481. Each axially protruding leg includes a distal tine end 482, 484. Distal tine ends 482, 484 flex into and out of the notches in longitudinal channel 9 (FIG. 53a) or spiral locking channel 7 (FIG. 53b) of a specially configured bolt. Counter-rotational movement is prohibited when the distal tine ends 482, 484 abut the locking face of one or more notches. Rotational movement is permitted because the distal tine ends 484, 482 ride on the opposing slope of the notch or notches and the bolt thread crest. The operation of the distal tine ends is shown earlier herein. As shown in FIG. 56a, the axially protruding legs are disposed circumferentially at certain regions beyond nut thread segments 475, 476 and 477.

FIGS. 56b–56h diagrammatically illustrate another type of locking fastener or clip. In FIGS. 56b–56d, tine support plate 1800 is bent normal to clip leg 1802. Clip leg 1802 includes a single thread bore 1804. Support plate 1800 is punched or tooled to define tine 1806. Side sections 1810, 1812 are bent normal to plate 1800 to provide additional support for the plate. See FIG. 56d. Axial compression of the fastener is limited by wall sections 1826, 1843. FIG. 56c is a head on view of the fastener clip. As shown, tine 1806 protrudes radially and tangentially towards center point 1805 of single thread 1804.

With respect to FIG. 56e, plate 1800 carries tine 1806. That tine cooperates with a groove or channel on the bolt secured to single thread 1804. Support plate 1800 does not include support end sections 1810, 1812 shown in FIGS. 56b–56d. The structure in FIGS. 56b–d is slightly more stable and less likely to twist upon application of excessive fastening torque.

FIGS. 56f–56h diagrammatically illustrate another type of construction for the single thread system. In FIG. 56f, single thread bore 1804 is carried by plate section 1820. Plate section 1822 is divided into end panel 1824, central panel 1826 and opposing side panel 1828. A tine 1830 is defined in central panel section 1826. The fastener includes a further plate section 1832 having a through bore 1834 therethrough. Through bore 1834 has a center point 1836. Single thread bore 1804 also has a center point 1803. The fastener further includes a trisected panel section 1840. Panel section 1840 includes side panels 1841, 1842 and central panel section 1843. A tine 1845 is defined in central panel section 1843.

To construct the fastener, center point 1836 of through bore 1834 is placed coaxial with respect to center point 1803 of single thread bore 1804. The plate is bent accordingly. FIG. 56g illustrates the completed fastener 1850. Similar numerals designate similar items in FIGS. 56f–56h. Side panels 1824, 1842 provide additional support for central panel 1826, 1843 which carry tines 1830, 1845. The side panels enhance axial compression and limit twisting of the fastener.

FIG. 56h is similar to the fastener discussed above in connection with FIGS. 56f and 56g. However, the fastener of FIG. 56h does not include supporting side panels. Instead, central panels 1826, 1843 carry tines 1830, 1845. This fastener utilizes less manufacturing steps than FIG. 56f.

Figures 57, 58:
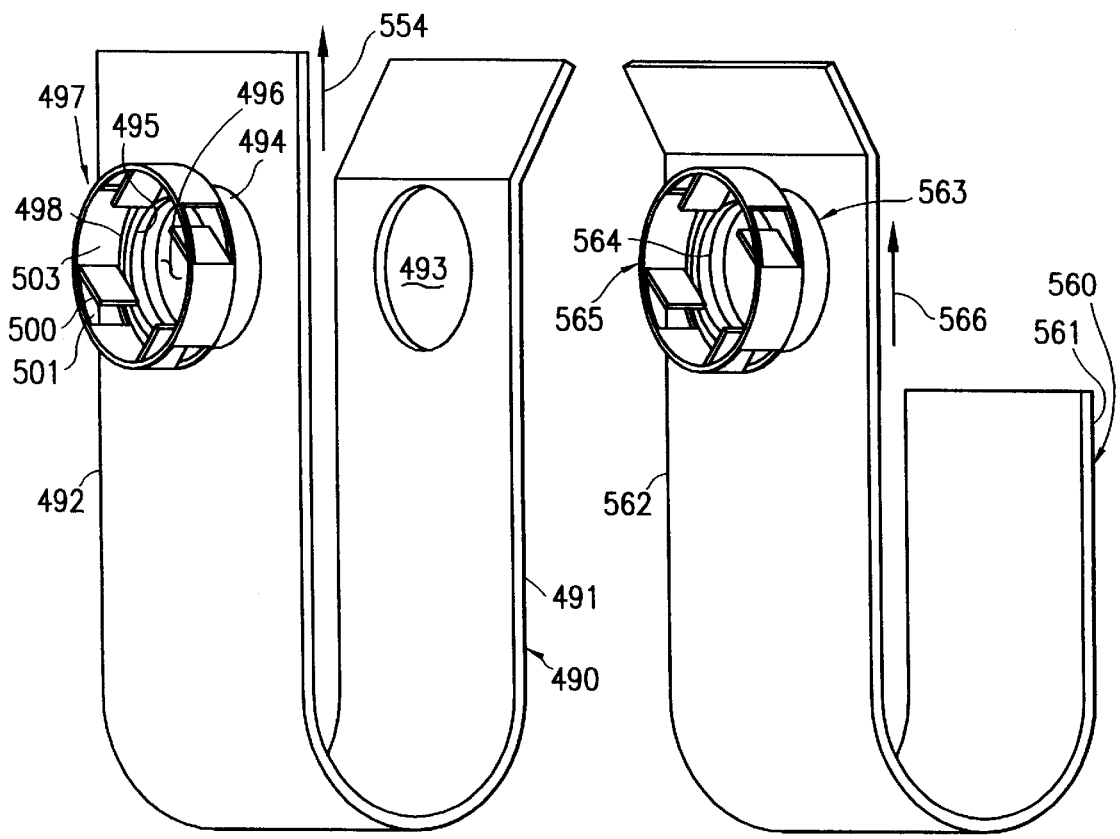
FIGS. 57 and 58 diagrammatically illustrate clips having a nut on one clip leg and a cylindrical locking unit formed on the outboard axial end of the nut.

FIG. 57 diagrammatically illustrates U-shaped clip 490 having clip leg 491 and clip leg 492. A bore 493 is defined on clip leg 491. A nut 494 is formed on clip leg 492. Nut 494 includes nut threads 495 and a nut bore 496. An elongated locking unit 497 is formed on an outboard axial end 498 of nut 494. The cylindrical locking unit 497 includes at least one, and in the illustrated embodiment, several compressible tines. For example, distal tine end 500 is defined in cut-out 501 of cylindrical wall 503 of cylindrical locking unit 497. Nut bore 496 is coaxial with respect to bore 493 on clip leg 491. U-shaped clip 490 is adapted to be inserted onto a panel having a bore in the direction shown by arrow 454. Examples of these bored panels are shown in panel 401 in FIG. 47 and panel 354 in FIG. 43, among others.

The clip fastener systems illustrated in FIGS. 57, 58, 59 and 60 include a threaded, extruded barrel 495 (FIG. 57) and a wider diameter extruded portion or cylinder 497 to accommodate a spacial flex zone that is not threaded. This double extrusion design saves material costs and space.

FIG. 58 shows a truncated U-shaped or J-shaped clip 560. Clip 560 includes truncated clip leg 561 and clip leg 562. A nut 563 is formed on clip leg 562. Nut 563 includes nut threads 564 and an elongated, cylindrical locking unit 565. J-shaped clip 560 is placed on a bored panel by moving clip 560 in the direction shown by arrow 566. Examples of bored panels are found in FIG. 47, panel 401; FIG. 39, panel 280 and FIG. 38, panel 299.

Figures 59, 60:
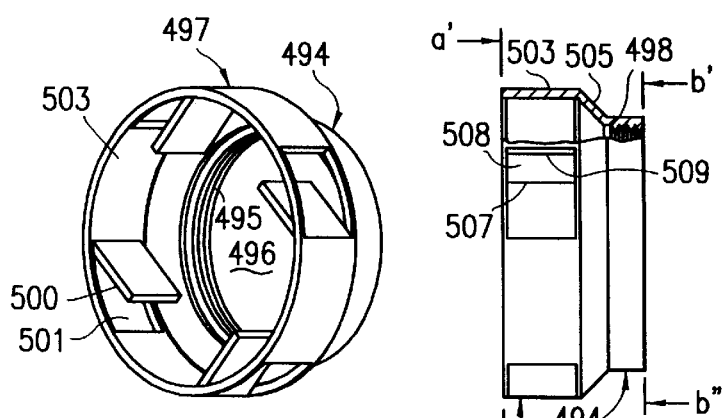
FIG. 59 illustrates a detailed view of the nut and cylindrical locking unit.
FIG. 60 diagrammatically illustrates a partial, cross-sectional, broken away side view of the nut with the cylindrical locking unit formed on an axial outboard end.

FIG. 59 diagrammatically shows a perspective view of cylindrical locking unit 497 mounted at an axial end of nut 494. Tine 500 is formed by cutting a cut-out 501 from cylindrical wall 503 of cylindrical locking unit 497. Additionally, tine 500 is pushed or forced radially inward toward nut bore 496.

FIG. 60 shows a partial, broken away, plan view of cylindrical locking unit 497 mounted at an axial end of nut 494. Nut 494 has an axial end 498. Cylindrical locking unit 497 includes a frusto-conical member 505 which leads to a larger diameter cylindrical member of cylindrical wall 503. Cylindrical wall 503 has a larger diameter as compared with frusto-conical member 504 and nut 494. The user can clearly see whether tine 507 is locked into one or more of the notches in longitudinal locking channel 9 (FIG. 53a) or spiral locking channel 7 (FIG. 53b) of the bolt. This is due to the fact that distal tine 507 is positioned in cut-out 508. Tine 507 has a proximal tine portion 509 that is adjacent cylindrical wall 503.

Figure 61A:
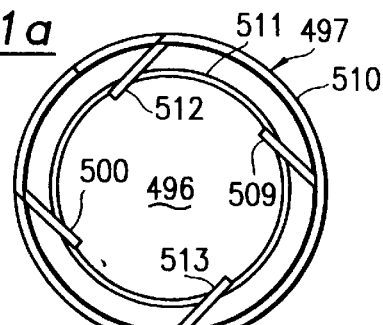
FIGS. 61a and 61b diagrammatically illustrate the tines from the perspective of section lines a'–a" and b'–b" in FIG. 60.
Figure 61B:
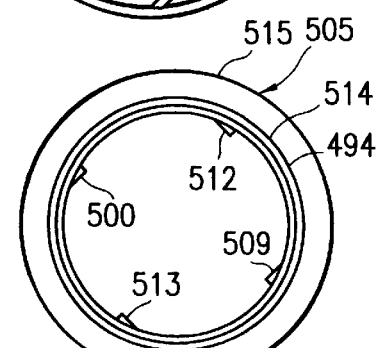

FIGS. 61a and 61b diagrammatically illustrates plan views from the perspective of section line a'–a" in FIG. 60 and section line b'–b" in FIG. 60. In FIG. 61a, the axially outboard edge 510 of cylindrical locking unit 497 is shown as is the axial outboard end 511 of the frusto-conical section 505 (FIG. 60). A plurality of tines 500, 512, 509 and 513 protrude tangentially and radially inward toward nut bore 496 which establishes the axial centerline of the nut. In FIG. 61b, the axially inward edge 514 of nut 494 is illustrated. The radially large outer edge 515 of frusto-conical member 505 (FIG. 60) is also shown in FIG. 61b. The distal tine ends 500, 512, 509 and 513 are also illustrated.

As discussed earlier, U-shaped clips 490, 560 are placed on a bored panel such that the axial centerline 496 of nuts 494, 563, are coaxial with the bore through the panel. Thereafter, a specially configured nut such as the nut shown in FIGS. 53a and 53b and bolts 14, 15 are threaded through the bores and onto nut threads 495, 564. Distal tine ends 500, 509, 512 and 513 pop into and out of one or more notches formed in longitudinal channel 9 of bolt thread segment 11 (FIG. 53a) or spiral locking channel 7 of bolt thread segment 13 on bolt 15 (FIG. 53b). Counter-rotational movement is prohibited when the distal tine end abuts the locking face 36 of the notch. Rotational movement is permitted when the bolt moves respect to the nut thread and the distal tine end rides on opposing slope 38 (FIG. 1b) and bolt thread crest 30. The user can determine whether the distal tine end is locked by viewing the tines in the cut-outs. The user can determine whether the cylindrical locking unit is locking on the specially configured bolt because the position of the distal tine end is visible due to the cut-outs. See cut-out 501 in FIG. 57 for tine 500 and cut-out 508 for tine 507 in FIG. 60.

FIG. 62 shows U-shaped clip 520 having clip leg 521 with a bore 522 there through. Clip 520 also includes clip leg 523. Clip 520 is placed on a panel 524 having a bore 525 there through. Clip 520 is placed on panel 524 by moving the clip in the direction shown by arrow 526. Clip leg 523 carries a nut and locking unit 527 thereon.

FIGS. 63a, b, c, d, e, f, g and h show various manufacturing stages and axial end views of the nut and locking unit 527. A perspective plan view of nut and locking unit 527 is shown in FIG. 64a. In FIG. 64a, the nut and locking unit is a cylindrical system having cylinder walls 528. The interior of cylinder wall 528 includes a nut thread 529. A locking unit 530 is formed on an interior of said nut. Locking unit 530 includes a distal tine end 540 protruding tangentially and radially inward toward the axially centerline of the nut and locking unit. The axial centerline 541 of the nut is shown in FIG. 63h. In the illustrated environment, nut and locking unit 527 includes a second distal tine end 542. The distal tine ends 540, 542 extend from tine bodies 543, 544. These tine bodies and distal tine ends are cutaway from cylinder nut wall 528.

In FIGS. 63a and 63b, cylinder body 528 of nut and locking unit 527 is mounted or formed on clip leg segment 523. As shown in FIG. 63b, which provides a view of cylinder 528 from the perspective of section lines b'–b" in FIG. 63a, cylinder 528 is an elongated, thin walled cylinder.

In FIGS. 63c and 63d, a tine body or locking unit body 530 has been cut or stamped out of cylindrical wall 528.

In FIGS. 63e and 63f, locking unit segment 530 has been forced radially outward. FIG. 63f shows locking unit segment 530 and locking unit segment 550.

In FIGS. 63g and 63h, locking unit segment 530 has been modified by bending distal tine end 540 radially inward to form the generally tangential and radially inward distal tine end. Tine body 543 provides added flexibility to the tine and proximal tine portion 551 adjoins tine body 543 with cylindrical wall 528.

As shown in FIG. 63h, distal tine ends 540, 542 protrude tangentially and radially inward toward axial centerline 541. Tine bodies 543, 544 protrude slightly radially outward beyond the radial dimension of cylinder wall 528.

Of course, cylinder wall 528 would have to be thick enough to accommodate and carry the nut threads 529 on its interior wall surface. Threads are formed after formation of the compressible tines.

Since the locking units 530, 550, are formed in cut-outs on the cylindrical wall 528, the user can visually determine whether distal tine ends 540, 542 have fallen into longitudinal locking channel 9 or spiral locking channel 7 in bolt 14, 15 shown in FIGS. 68a, 68b.

The "punctured barrel" clip or fastener locks shown in FIG. 64a (and the associated U & J-shaped clips, FIGS. 62 and 65) utilize a spacial flex zone that radially extends outside the barrel 528. This extended flex zone increases tine length and, when combined with a distal tine bend 540, 542, results in a predetermined angle of engagement.

Figure 64B:
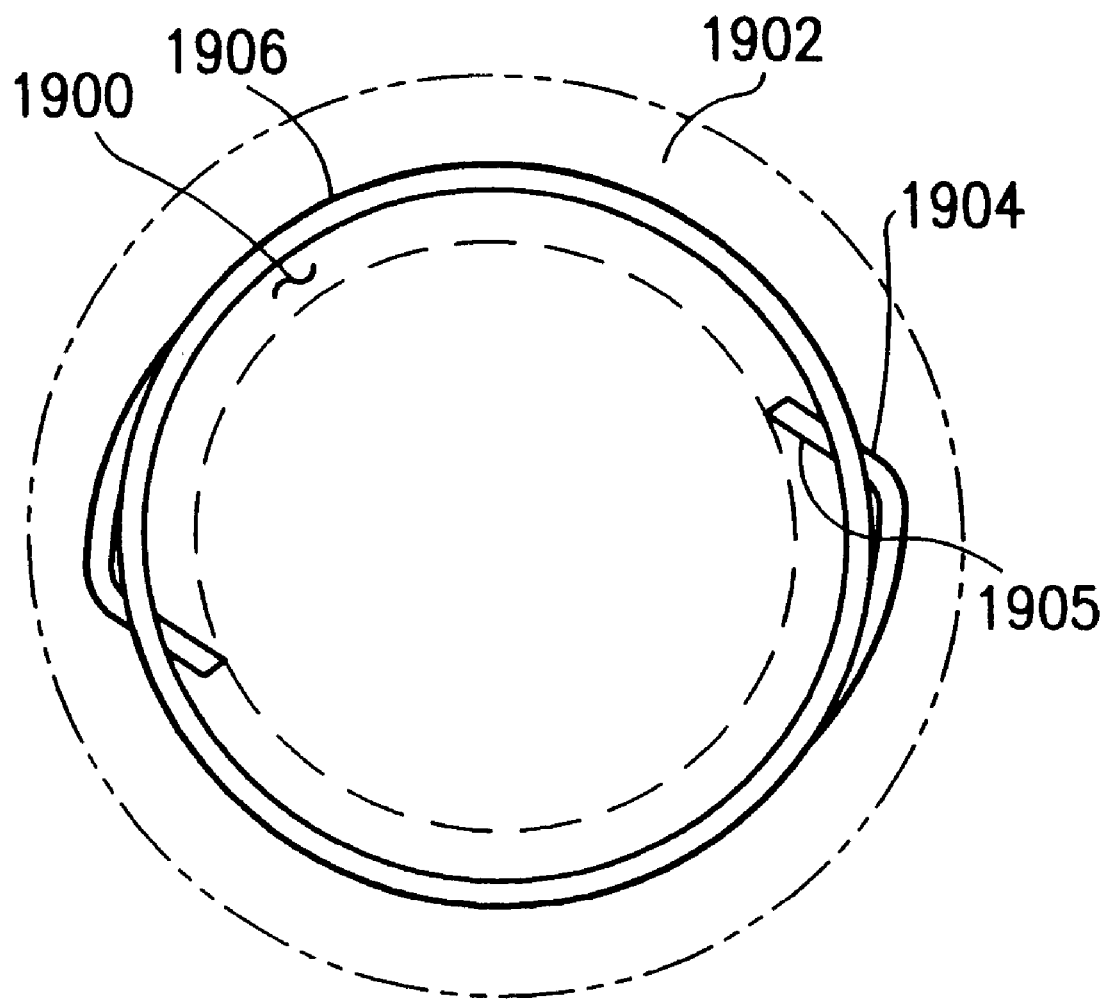
FIG. 64b graphically illustrates the spacial flex zone and locking zone for the locking fasteners illustrate FIGS. 64a and 67.

FIG. 64b graphically illustrates the locking zone 1900 for the punctured barrel clip locks shown in FIGS. 64a and 67 (discussed later). The spacial flex zone 1902 for tine 1904 is outside the threaded barrel 1906. Of course, threaded barrel 1906 also provides the cylindrical support for tine 1904. The use of spacial flex zone 1902 outside of threaded barrel 1906 enables an increase in tine length 1904. When this increase length is combined with secondary bend 1905 at the distal end of tine 1904, a larger angle of engagement is achieved on the specially configured bolt (FIGS. 68a, 68b and 2b). This increases the fastening or clamping ability.

FIG. 65 diagrammatically shows a J-shaped clip 570. Of course, as explained earlier, clip 570 is a U-clip with a truncated clip leg 571. Clip 570 includes clip leg 572 on which is mounted, attached or formed a nut and locking unit 573. This nut locking unit 573 is described in detail in conjunction with FIGS. 66a–d and 67. When clip 570 is placed on bored panel 574 by moving the clip in the direction shown by arrow 575 and bore 576 of nut and locking unit 573 is coaxial with bore 577 on panel 574, one of the specially configured bolts 14, 15 (FIGS. 68a, 68b) may be utilized to lock the bolt on the locking nut clip assembly and particularly clip 570.

Nut and locking unit 573 is generally similar to the nut and locking unit 527 discussed earlier. However, the locking unit element is moved from an intermediate position on the nut threads to an axially outboard position near axial end 578 of nut 573.

FIGS. 66a–d diagrammatically illustrate various stages of manufacture of the nut and locking unit 573. In FIG. 66a, a thin wall cylinder 580 is formed, mounted or attached to clip leg segment 572. In FIG. 66b, a locking unit segment 581 is cut or formed from thin walled cylinder 580. In FIG. 66c, tine segment 581 is moved radially outward as shown by arrow 583 away from nut bore 576. In such a configuration, tine segment 581 operates substantially the same as tine segment 530 in FIG. 63f. In FIG. 66, the tine segment has been further divided into tine body 585 and distal tine end 586.

In FIG. 67, the nut and locking unit 573 is shown as having tine body 585, tangential and radially inwardly disposed distal tine end 586 and tine body 587 with a distal tine end 588. Thin walled cylinder 580 has a nut thread 590 formed thereon. In this manner, when one of the specially configured bolts 14, 15 (FIGS. 68a, 68b) are coaxially disposed through panel bore 577 (FIG. 65) and the bolts are threaded on nut thread 590, locking is achieved when distal tine ends 586, 588 fall within and abut one or more of the locking faces in longitudinal locking channel 9 or spiral locking channel 7 of bolts 14, 15. Otherwise, the bolt moves rotatably with respect to the nut and locking unit assembly 573 because the distal tine end rides on opposing slope 38 (FIG. 1b) or atop bolt thread crest 30. The user can visually confirm whether the distal tine ends have locked onto the locking channels because the distal tine ends move in and out appropriate cut-outs in the thin walled cylinder 580. Visibility is enhanced due to these cut-outs.

Bolts 14, 15 illustrated in FIGS. 68a, 68b are described in detail earlier herein.

Figure 69:
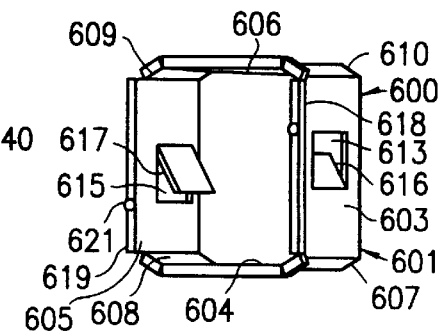
FIG. 69 diagrammatically illustrates a perspective view of a locking unit having a peripheral wall with a plurality of tines protruding tangentially and radially inward.

FIG. 69 illustrates a perspective view of locking unit 600 which, when utilized in connection with a latch, enables the user to close the tines thereby enabling full rotational and counter-rotational movement and, alternatively, unlatch and fully exposing the tines and providing a locking nut and bolt system in a locking position. Elongated locking unit 600 illustrated in FIG. 69 includes a peripheral wall 601 which includes planar wall segments 603, 604, 605 and 606 as well as adjoining wall segments 607, 608, 609 and 610. As described later in connection with the elongated locking unit shown in FIG. 75a, peripheral wall 601 may be cylindrically formed. Peripheral wall 601 is elongated in that it has a reasonable axial dimension. The axial dimension of peripheral wall 601 is shown as dimension 612 in FIG. 71a.

Planar wall segments 603,605 include cut-outs 613, 615 which enable the formation of distal tine ends 616, 617. Peripheral wall segments 603,605 also include radially extending lips 618, 619. In order to provide stops for the slidable latch (described later in conjunction with FIG. 70), a stop button or control surface 620, 621 is provided on lips 618, 619. The other planar walls 604, 606 also include radially extending lips. Wall segments 607, 608, 609 and 610 also include radially extending lips along respective axially outboard edges.

Figure 74A:
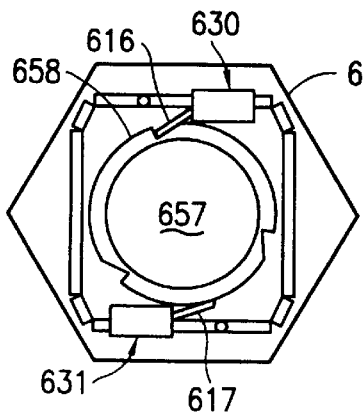
Figure 70:
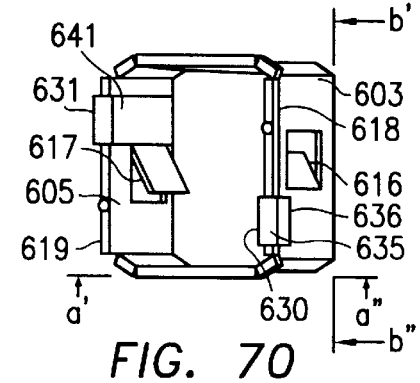
FIG. 70 diagrammatically illustrates a perspective view of the locking unit carrying two latches which are moveably disposed on the peripheral wall carrying the locking tines.

In FIG. 70, latches 630, 631 are moveably disposed on peripheral wall segments 603, 605. As shown in FIG. 70, the latches 630, 631 fully expose tines 616, 617. The latches are shaped complementary to the peripheral wall. By fully exposing tines 616, 617, the tines and the latches are in a locking position. The locking position is shown in FIG. 74a. In order to provide a moveable latch 630, 631, the axially outboard edges of peripheral wall segments 603, 605 form either channels or channel members. Latches 630, 631 form complementary channel members or complementary channels. In the illustrated embodiment, the radially outwardly extending lips 618, 619 of peripheral wall segments 603, 605 establish channel members. The channel is formed on the latch by an axially outboard and radially extending surface 635 and a tangentially extending surface 636. See FIG. 71a. In other words, each latch 630, 631 includes an axially extending latch wall 640, 641 (see FIG. 71a) and, that latch wall, in conjunction with radial surface 635, and tangential depending surface 636, forms an inverted L-shaped channel at an axially outboard position of the latch. The radial lip 618 of peripheral wall segment 603 forms the channel member which is trapped within the channel formed by latch wall 640, radial latch wall 625 and tangential latch wall 636.

Figure 71A:
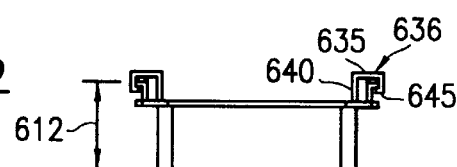
FIGS. 71a and 71b diagrammatically illustrate side views from the perspective of section line a'–a" in FIG. 70 from the perspective of section line b'–b" in FIG. 70.

FIG. 71a diagrammatically illustrates the channel formed by the latch. In addition, a lower radially inward extending channel defining latch member 645 is provided.

Figure 71B:
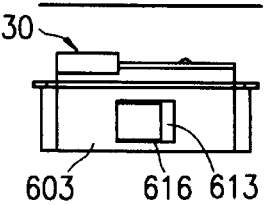

FIG. 71b shows latch 630 in a locking position fully exposing tine 616. The latch is moved far away from the stop. As discussed in detail earlier, tine 616 is formed in a cut-out 613 in peripheral wall segment 603. The tine prevents counter-rotational movement when co-acting with one or more notches on the bolt.

Figure 72:
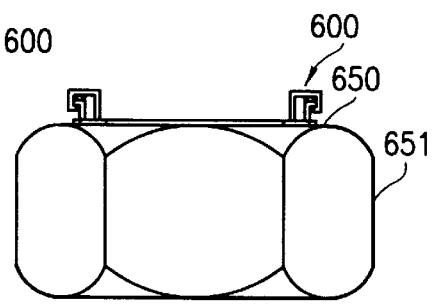
FIG. 72 illustrates a side view of a nut carrying the locking unit.

FIG. 72 shows elongated locking unit 600 disposed in a recess below nut end face 650 of nut 651. This recess is similar to other recesses discussed herein. See, for example, FIG. 15.

Figure 73A:
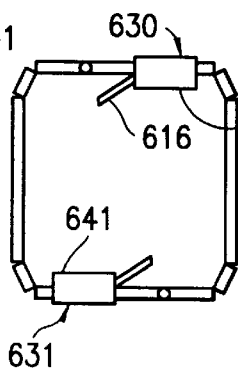
FIGS. 73a, b and c and 74a, b and c diagrammatically illustrate top views of the locking unit in a locking position; an intermediate position and a closed position (FIG. 73c) and the locking unit disposed in a nut with a bolt threaded on the nut in a locking position, an intermediate position and a closed position (FIG. 74c)

FIGS. 73a, b and c diagrammatically illustrate the closing action of latch 630 with respect to distal tine end 616. In FIG. 73a, latch 630 fully exposes distal tine end 616 thereby enabling the tine to lock onto one or more notches in longitudinal locking channel 9 shown on bolt 14 in FIG. 68a or spiral locking channel 7 shown on bolt 15 in FIG. 68b.

Figure 73B:
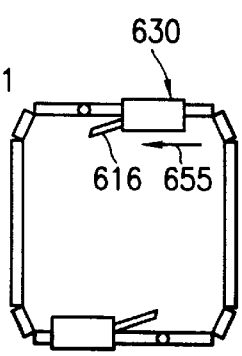
Figure 73C:
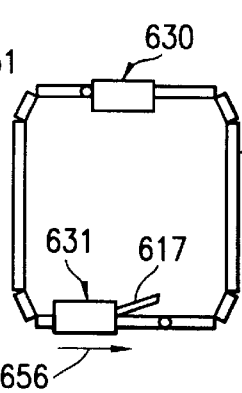

In FIG. 73b latch 630 has been moved in the direction shown by arrow 655 which is near the capture or closed position for distal tine end 616. In FIG. 73c, latch 630 is completely capturing tine 616 thereby placing the tine in a closed position. When the tine is in a closed position, the bolt may move in a rotational and a counter-rotational with respect to the nut thread. Of course, in order to fully place the elongated locking unit 600 in a fully closed position, latch 631 must be moved in the direction shown by arrow 656 to capture distal tine end 617.

FIGS. 74a, b and c diagrammatically show bolt 657 threaded onto nut 651. In FIG. 74a, latch 630 fully exposes distal tine end 616 and that tine has dropped into a notch in bolt thread 658. Distal tine end 617 is also fully exposed in a locking position due to the position of latch 631.

Figure 74B:
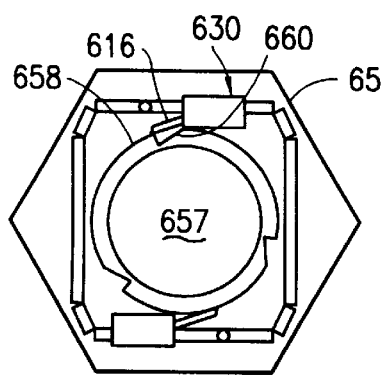
Figure 74C:
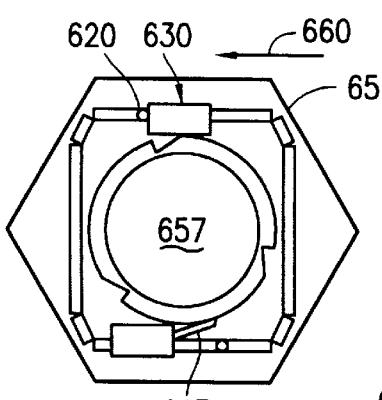

In FIG. 74b, latch 630 is in an intermediate position between locking position (FIG. 74a) and the closed position (FIG. 74c). Distal tine end 616 is only partially removed from notch 660 on bolt thread 658. In FIG. 67c, latch 630 has completely captured the associated distal tine end thereby permitting bolt 657 to rotate in either rotational or counter-rotational movement. Of course, when distal tine end 617 falls within one or more notches, counter-rotational movement is prohibited. FIG. 74c also shows that latch 630 has been moved in the direction shown by arrow 660 such that the latch abuts stop 620. Various types of stops such as buttons, walls, etc. can be utilized.

As a further enhancement of the latch, the axially inboard portion of the latch may require the formation of a channel within which the axially inboard edge 659 (FIG. 71a) acts as a channel member. The channel is formed by an axially inboard lip region of the peripheral wall.

FIGS. 75a and 75b show a perspective view of a cylindrical locking unit 662. Cylindrical locking unit 662 includes a cylindrical peripheral wall 663 which has cut-outs 664,665 within which are disposed distal tine ends 666, 667. Elongated locking unit 662 also includes a radial lip 668.

FIG. 75b shows that radial lip 668 has been segmented and rolled radially inward to form radially inward lip segments 669 and 670. As discussed later, these radially inward lip segments 669, 670 operate as channel members in order to guide the latch. These channel members 669, 670 inter-fit with certain defined channels in the latch.

FIG. 76 shows a cylindrical latch 671 having a cylindrical wall 672 which is complementary to cylindrical peripheral wall 663. In other words, cylindrical latch 672 is adapted to be inserted and inter-fit into cylindrical wall 663. Cylindrical latch 671 includes a corresponding cut-out 673, 674 for each distal tine end 666, 667. Latch wall 672 also includes channels defined as cut-outs 675, 676. Radially inward lip channel members 669, 670 (FIG. 75b) of the cylindrical locking unit are placed within channels 675, 676 of the latch. Cylindrical latch 671 includes an axial end cap 678. Axial end cap 678 includes a slot 679 thereon. This slot enables the user to turn the cylindrical latch with a screwdriver or other thin tool.

FIG. 77 shows elongated locking unit 662 carrying cylindrical latch 671. Distal tine end 666 is fully exposed in cut-out 664. This reveals that cylindrical latch 671 is in a locking position.

FIG. 78 shows cylindrical locking unit 662 mounted in a recess in nut 680. Cylindrical latch 671 is mounted within cylindrical locking unit 662. The nut with a recess is described earlier.

FIG. 79 shows a perspective view of cylindrical latch 671 without axial end cap 678. Similar numerals designate similar items in FIGS. 76, 77 and 79.

In FIG. 80, cylindrical latch 671 has been placed in cylindrical locking unit 662. As shown in FIG. 80, radially inward lips 669, 670 form channel members on the locking unit which cooperate with the respective channels 675, 676 on the latch. As shown in FIG. 80, the cylindrical latch 671 fully exposes distal tine ends 666, 667 thereby providing a locking position of the latch and locking unit 662. When the latch is rotated in the direction shown by arrow 683, distal tine ends 666, 667 are trapped by latch cylindrical wall 672 and are in a closed position.

FIG. 81 shows cylindrical latch 671 mounted within cylindrical locking unit 662. FIG. 82 shows cylindrical locking unit 662 mounted in a recess in nut 680. Cylindrical latch 671 extends axially outboard of end face 681 of nut 680. Of course, the distal tine ends 666, 667 extend tangentially and radially inward toward axial centerline 685.

FIG. 83 shows a specially configured bolt 1 with longitudinal locking channels 3 thereon. Nut 680 will be threaded onto the bolt threads of bolt 1. Nut 680 carries cylindrical locking unit 662 and cylindrical latch 671.

In FIG. 84, bolt 1 has been threaded onto nut 680 and captures panels 687, 688,

FIGS. 85 and 86 show bolts 14, 15 having a longitudinal locking channel 9 and a spiral locking channel 7, respectively. Longitudinal locking channel 9 is disposed on bolt thread segment 11. Spiral locking channel 7 is disposed on bolt thread segment 13. Rather than using bolt 1 with longitudinal locking channels 3, this system described as the cylindrical locking unit 662 and the cylindrical latch 671 can be used with bolt 15 having the spiral locking channel 7.

Figures 87A, 87B:
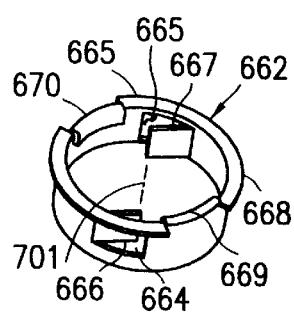
FIGS. 87a and 87b diagrammatically illustrate a perspective view of a cylindrical locking unit before and after a channel member has been defined on the peripheral wall carrying the locking tines.

FIGS. 87a and 87b show a cylindrical locking unit 662 similar to the cylindrical locking unit shown in connection with FIGS. 75a and 75b above. Distal tine ends 666, 667 extend tangentially and radially inward toward the axial centerline 701 of cylindrical locking unit 662. Radially inward channel members 669, 670 are formed from a portion of radially outward extending lip 668.

Figure 88:
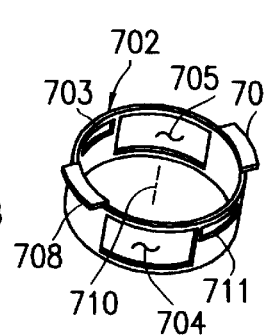
FIG. 88 diagrammatically illustrates a cylindrical latch having a user actuatable control surface extending radially from one axial end thereof.

FIG. 88 diagrammatically illustrates a cylindrical latch 702 having a peripheral, cylindrical wall 703. Peripheral wall 703 includes cut-outs 704, 705. In additional, peripheral wall 703 includes radially extending, user actuatable control surfaces 707, 708. Control surfaces 707, 708 extend radially beyond the axial centerline 710 of cylindrical latch unit 702. In additional, peripheral wall 703 includes a channel cut-out 711. Channel cut-out 711 cooperates with channel member 669 in FIG. 87b in order to provide guidance for the rotation of cylindrical latch 702 with respect to cylindrical locking unit 662. Basically, the latch stops at either end of channel 711 based upon the size of channel 711 and the size of radially inward channel members 669. Another channel would be formed on the opposing portion of peripheral wall 703 to accommodate radially inward channel member 670. Alternatively, these channels and channel members may be deleted in favor of radial stops provided by the user actuatable control surfaces.

Figure 89:
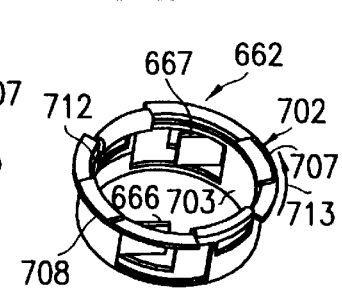
FIG. 89 diagrammatically illustrates a perspective view of a cylindrical locking unit and a complementary cylindrical latch mounted therein.

FIG. 89 shows a perspective view of cylindrical latch 702 inserted into cylindrical locking unit 662. Radially extending control surfaces 707, 708 enable the user to rotate cylindrical latch 702 within cylindrical locking unit 662. As an alternative embodiment, radially inward lips 669, 670 can be wrapped around the axial edge 712 of cylindrical latch 702. In this manner additional guide channels are provided for the latch. As shown in FIG. 89, cylindrical latch 702 fully exposes distal tine ends 666, 667, thereby providing a locking position for the cylindrical locking unit 662 and the cylindrical latch 702. When the cylindrical latch 702 is moved in the direction shown by arrow 713, the peripheral wall 703 of latch 702 captures distal tines 666, 667 and prohibits the distal tine ends from locking onto the locking surfaces of a longitudinal locking channel 9 (FIG. 85) or a spiral locking channel 7 (FIG. 86).

Figure 90:
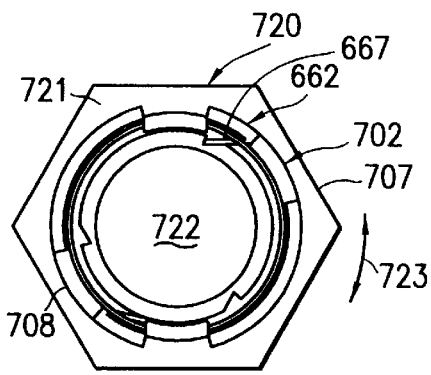
FIG. 90 illustrates an end view of the cylindrical locking unit and cylindrical latch mounted into the recess on an end face of a nut.

FIG. 90 illustrates an end view of bolt 720 which carries in a recess on bolt end face 721 the cylindrical locking unit 662. Cylindrical latch 702 is disposed within the interior of cylindrical locking unit 662. The user actuatable control surfaces 707, 708 are available for use. A bolt 722 is threaded into nut 720. Distal tine ends 667 have fallen into the appropriate notch and the distal tine end 667 abuts the locking face thereby preventing counter-rotational movement of bolt 772 in direction 723 with respect to nut 720.

Figure 91:
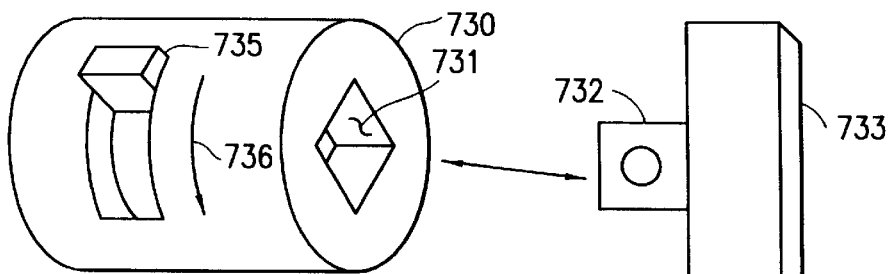
FIG. 91 diagrammatically illustrates a socket with a cylindrical latch having a user actuatable control surface extending from the socket (i.e., a removal tool) which is about to be mounted on a receptacle on a rachet tool.

FIG. 91 diagrammatically illustrates a socket 730 having a female socket fitting 731. Female socket fitting 731 is sized to mate with male rachet fitting 732. Male fitting 732 is attached to a rachet 733. Rachet 733 is a conventional tool. FIG. 91 also shows a user actuatable control surface 735 which is functionally equivalent to control surfaces 707, 708 for cylindrical latch 702. By moving control surface 735 in the direction shown by arrow 736, the user can place the elongated locking unit and the cylindrical latch in a closed position, thereby enabling the user to move the bolt in a clockwise rotational movement and a counterclockwise rotational movement via rachet tool 733.

Figure 92:
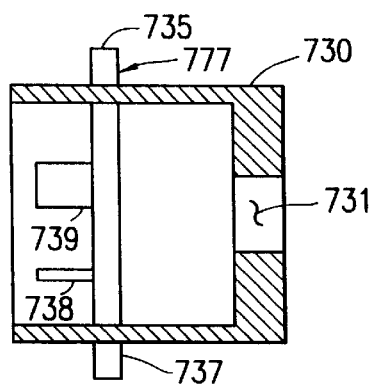
FIG. 92 diagrammatically illustrates a plan view of the socket and the cylindrical latch with a user actuatable radial control surface.

FIG. 92 illustrates a plan view of the socket. Socket 703 and female fitting 731 are diagrammatically illustrated in FIG. 92. The cylindrical latch 777 having a user actuatable control surface 735, 737 is also shown. The cylindrical latch has axially extending legs 738, 739 that operate in the same manner as peripheral latch wall 703 in cylindrical latch 702. In other words, when axial latch panels 738, 739 trap distal tine ends 666, 667, the tool is in a closed position and the user can operate rachet tool 733 in either a clockwise or counterclockwise manner. The distal tine ends do not abut the locking face of the specially configured bolt thereby permitting counter rotational movement. When the axial legs 738, 739 of cylindrical latch 777 are circumferentially disposed away from distal tine ends 666, 667, the system is in a locking position and the user may only rotate the bolt with respect to the nut in a clockwise or single rotational direction.

Figure 93:
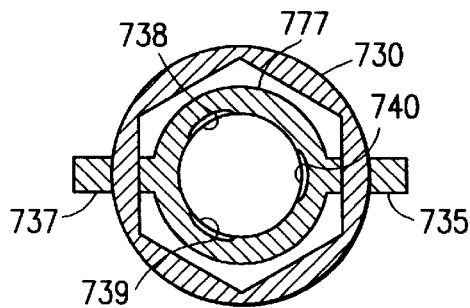
FIG. 93 diagrammatically illustrates a cross-sectional plan view of the socket and the cylindrical latch.

FIG. 93 diagrammatically shows the latch system. Socket 730 is shown in cross section and user actuatable control surfaces 735, 737 are visible. Cylindrical latch 777 has axially depending legs 738, 739 and 740.

FIGS. 94a and 94b diagrammatically illustrate a female threaded unit 750. Female threaded unit 750 includes a bore 752 carrying a female thread 753. Female thread 753 is complementary to a bolt. In FIG. 94b, surface 754 of female threaded unit 750 has a recess 755 formed therein.

FIGS. 95a and 95b illustrate a perspective and a side view of locking unit 760. In the illustrated embodiment, locking unit 760 is shaped as a rectangle. However, the locking unit could be cylindrical as shown with respect to locking unit 662 in FIG. 75b. The shape of locking unit 760 is complementary to the shape of recess 755. Locking unit 760 includes a plurality of distal tine ends 761, 762, 763 and 764.

These distal tine ends protrude tangentially and radially toward the axial centerline 765 formed within locking unit 760. Locking unit 760 also includes a central bore 766. As explained later, a specially configured bolt passes through bore 766. If a cylindrical locking unit is utilized, bore 766 would be defined by the cylindrical locking unit body. See FIG. 75*b*. The distal tine ends 761, 762, 763 and 764 are formed by cut-outs in the locking unit wall. One cut-out 768 is associated with tine 762.

FIG. 95*b* shows a side view of locking unit 760 and particularly distal tine end 764. Distal tine end 764 is formed and operates in cut-out 770. The view in FIG. 95*b* is from the perspective of section line b'–b" in FIG. 95*a*.

FIG. 96 diagrammatically illustrates female threaded unit 750 having locking unit 760 installed in recess 755. As shown, distal tine ends 761, 762, 763 and 764 protrude axially toward the actual centerline of nut thread 753 in the female unit 750.

FIGS. 97*a*, 97*b* and 97*c* show a specially configured bolt 772. Bolt 772 has a bolt stem 773 with a bolt thread 774. Bolt 772 includes a bolt head 775 defining a plurality of notches thereon, one of which is notch 776.

FIG. 97*b* is a top view from the perspective of section line b'–b" in FIG. 97*a*. In FIG. 97*b*, bolt head 775 has a plurality of notches, one of which is notch 776. Notch 776 includes a locking face 777 and an opposing slope 778.

FIG. 97*c* shows bolt 772 and notches spaced circumferentially spaced around bolt head 775. In other words, notch 776 is spaced from notch 780 by an arc 781. The larger the arc 781, the less digital locking action is provided by the bolt head and the distal tine ends of the locking unit.

FIGS. 98*a* and 98*b* show a perspective view and an end view of the locking nut and bolt system as a "blind hole" design. In FIG. 98*a* female threaded unit 750 has bolt 772 threaded therein. Distal tine end 761 is locking into notch 776. Counter rotational movement in the direction shown by arrow 790 is prohibited. In other words, if bolt 772 were moved in direction 790 with respect to female threaded unit 750, such counter rotational movement would be prohibited. Alternatively, if bolt 772 were moved in a direction opposite to direction 790, the tine would move over the notch in the bolt head.

FIG. 98*b* clearly shows distal tine ends 761, 762, 763 and 764 acting in respective notches for example notch 776 in conjunction with distal tine end 761. Since all of the distal tine ends have locked onto and abut a respective lock face 36 (FIG. 1*b*) of the respective notch, counter rotational movement is prohibited.

As stated earlier, rather than a rectangular locking unit 760 a cylindrical locking unit 662 shown in FIG. 75*b* may be utilized. The operation of a cylindrical locking unit 662 is substantially identical to the action of rectangular locking unit 760.

General comments regarding the blind hole screw design follow.

The blind hole screw head grooves must have one or more engagement walls.

The angle of engagement should be less than 90 degrees to prevent the tine from disengaging from the screw head.

The blind screw system permits a screw to mechanically lock into a blind hole or tapped hole.

The blind hole screw system includes, in some embodiments, tines incorporated within recesses of any shape, polygonal or otherwise, to prevent the rotation of the entire locking mechanism. Compare FIGS. 95*a*, 107, 108, 110*a*, 110*c* and 111*a*.

The blind hole screw system may include tines mounted on non-recessed shapes that abut faces, shapes or other bolts to prevent the rotation of the entire locking mechanism. See FIG. 111*a*. FIG. 95*a* shows a recessed blind hole.

Some embodiments of the blind screw include a tine mechanism with a seat with a hole through which a screw passes prior to insertion into the blind hole—to which is attached a myriad of optional configurations that include a locking mechanism or series of locking mechanisms to engage in the grooves of the screw head, and those locking mechanisms be housed or secured in an assortment of recess designs or in the absence of a recess, an assortment of forms, posts or objects, thereby preventing the seat from rotation around with the screw.

A anti-rotation protrusion on the underside of a blind hole clip may key into a recess adjacent to the blind screw hole.

Other screws may be used to mutually prevent locking mechanism rotation.

The blind screw may include a screw that uses a tapered or curvilinear surface on the underside of the screw head to deflect a locking device into the screw head or locking mechanism so as to not damage or crush the tines. A self-threading screw may be utilized.

In some embodiments of the blind screw, the system incorporates self tapping screw technology or any other thread form, including standard thread patterns, into the shank of the screw to permit fastening into any material. The head of the screw or bolt must carry grooves. See FIG. 104, for example.

General comments regarding blind hole screws and clips and removal tools follow.

In some embodiments of the blind screw, the system is enabled to remove the locking mechanism with a tool or destroy the locking mechanism of the blind or tapped screw during servicing without damaging the threaded features of the tapped hole, the threaded features of the screw itself, or the locking grooves incorporated within the head of the screw. Adhesives will actually "weld" a tapped screw in place under of high temperature conditions requiring drill taps to remove the screw.

The locking mechanism may be manufactured in any shape to increase the number of tines or reduce the circumference of the space taken up around the blind hole or to fit the tines into an unusual recess dictated by the tapped hole and its surrounding structures.

Visual inspection of the blind screw enables the user to visually inspect the locking feature of the blind hole confirming locking engagement.

In all embodiments of the blind screw, normal tools may be used for installation. Drive heads in the blind hole screw can be Phillips, hexlobe, Allen, standard screw drive heads, Torx®, etc., or any other licensed proprietary drive.

The "V" cuts in the blind hole clip allow proper seating in a beveled blind hole or a funnel shaped blind hole. See FIG. 106.

Other embodiments of the blind hole design are discussed below in connection with FIGS. 103*b*–112*c*.

Figure 99:
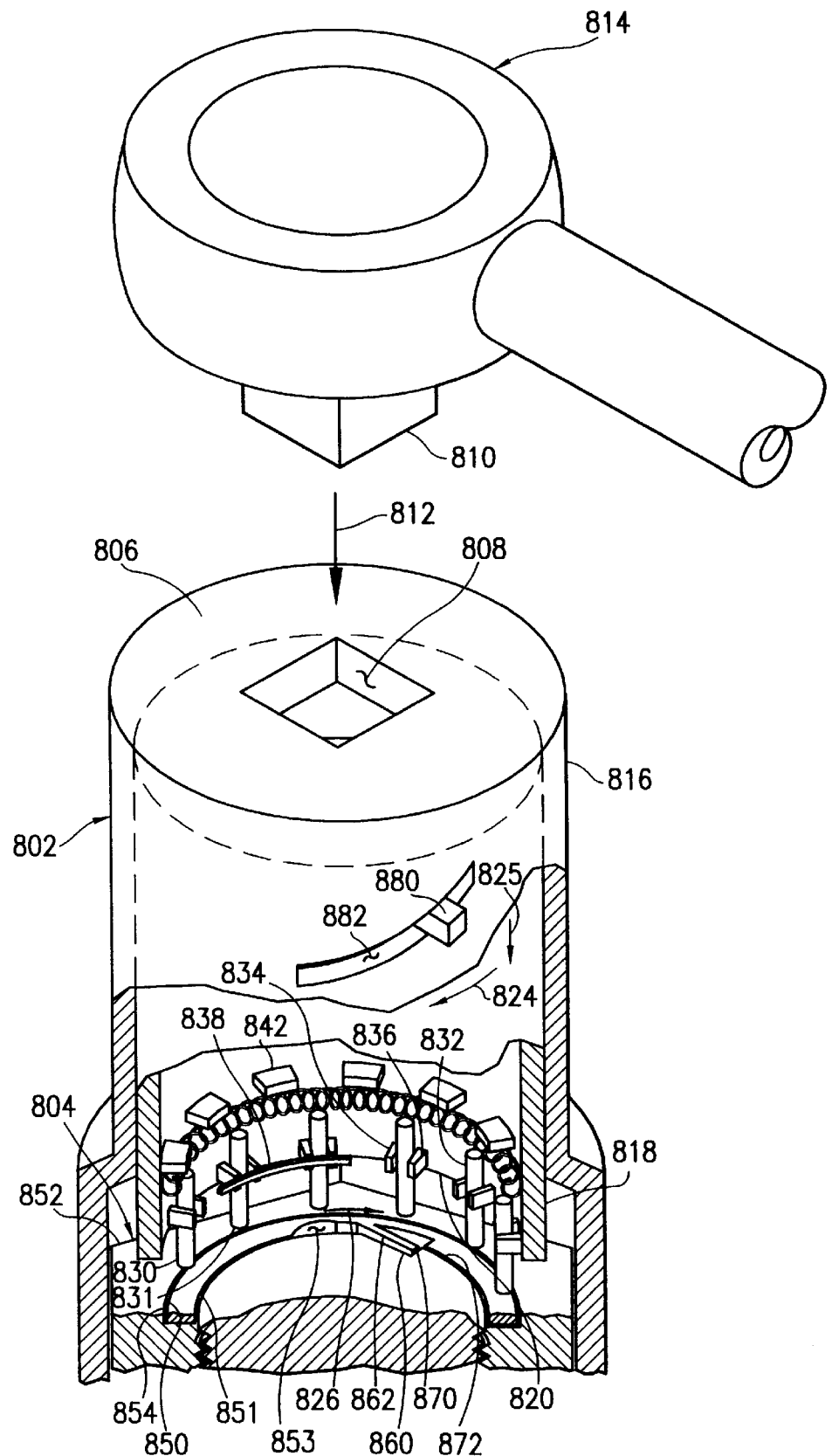
FIG. 99 diagrammatically illustrates a removal tool about to be placed atop the locking nut and associated bolt.

FIG. 99 diagrammatically illustrates a removal tool 802 about to be placed atop a locking nut and bolt assembly 804. Top end 806 of removal tool 802 includes a female socket fitting 808 into which male socket 810 is inserted as shown by arrow 812. Male socket fitting 810 is part of the conventional ratchet 814.

In the illustrated embodiment, removal tool 802 includes an outer cylinder 816 and an inner cylinder or cylindrical body 818. The outer shape of cylinder 816 may be altered. It is the inner cylindrical shape that is important since body 818 rotates within cylinder 816. Also, the removal tool may be configured exclusively as cylindrical body 818 with the depressible legs as described herein. Cylindrical body 818 has an open end which is established by lower edge 820. Since cylindrical body 818 is shown in a partial, broken away view, only the rearward arcuate edge 820 is illustrated in FIG. 99. As discussed later, if the forward portion of cylindrical body 818 is rotated in the direction shown by arrow 824, the rearward arcuate edge 820 moves in the direction shown by arrow 826.

A plurality of depending legs axially extend beyond lower edge 820 of cylindrical body 818. For example, see legs 830 and 832. The depending legs 830, 832 are axially moveable within guide channels formed near lower edge 820. In the illustrated embodiment, these guide channels are formed by lateral stops 834, 836 specifically illustrated in connection with depending leg 832. In order to limit radial movement of the depending legs, a circumferential bar 838 traps the moveable depending legs between the lateral stops. Circumferential bar 838 is shown in connection with depending leg 830. Other guides such as tongue and groove structures may be utilized.

Each depending leg axially moves relatively independent of the other legs. Also, each depending leg is axially biased outward, beyond edge 820. In the illustrated embodiment, this axially outward bias is provided by a spring 840. To provide relatively independent movement for each depending leg, spring 840 rests against one or more upper stops 842. Of course, each depending leg could be axially biased outward on its separate spring. Also, there are many mechanisms to capture single, circumferential spring 840 while providing for independent, axially outboard biasing of depending legs 830, 832. The claims appended hereto are meant to cover these and other modifications.

Also, the removal tool may be much smaller than illustrated herein and the proportional size of depending legs relative to the locking body (discussed later) may be different than illustrated herein. The removal tool drawings are illustrative of the concepts discussed herein.

In operation, lower edge 820 of cylindrical body 818 is sized to mate closely with locking body 850 and bolt thread 872. Nut 852 carries locking body 850 in a recess 854 below the nut face. Locking body 850 includes a locking tine having a distal tine end 860 and a proximal tine body 862. As described earlier, distal tine 860 falls into one or more of a plurality of notches 870 on bolt thread 872. The locking body may be configured as shown in many earlier figures.

Locking body 850 has a radially inward edge 851 that closely follows bolt thread 872. Other than interspace 853 between locking body edge 851 and bolt thread 872, locking body 850 closely matches the circumferential size of bolt thread 872.

Since lower edge 820 of cylindrical body 818 is complementary to bolt thread 872, depending legs 830, 832 are also complementary and circumferentially disposed about the radially outer periphery of bolt thread 872. In operation, lower edge 820 is place atop bolt thread 872 and one or more depending legs 830, 832 fall within the interspace 853 between locking body edge 851 and bolt thread 872. When cylindrical body 818 is rotated as shown in the direction 826 and depending leg 831 is axially disposed in interspace 853, the leg is forced against and radially outwardly moves proximal tine body 862. By moving proximal tine body 862 radially outward, distal tine end 860 is moved out of notch 870. This enables counter rotational movement of the bolt relative to the nut. This counter rotational movement can be provided, in the illustrated embodiment, by the appropriate directional movement of ratchet 814. In summary, the removal tool unlocks the nut from the bolt.

Figure 100:
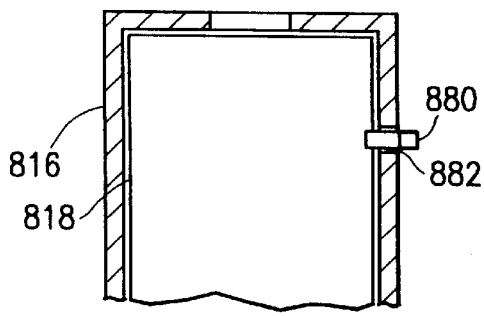

In the illustrated embodiment, cylindrical body 818 is coaxial with respect to outer cylinder 816. Rotational movement of cylindrical body 818 with respect to outer cylinder 816 is provided by moving user actuatable control surface 880. User actuatable control surface 880 protrudes radially outward through a hole 882 in outer cylinder 816. In the illustrated embodiment, hole 882 is a partial spiral such that when control surface 880 is moved in the direction shown by arrow 824, cylindrical body 818 moves rotatably and axially with respect to the relatively stationary outer cylinder 816. Also, cylindrical body 818 is moved axially outward or downward as shown by arrow 825 based upon control surface 880 moving in partial spiral 882. Of course, hole 882 could be a circumferential arc such that removal tool moves rotatably and not axially with respect to other cylinder 816. In this configuration, the user would place body 818 on the locked bolt an rotate the unit until one or more depending legs are forced into the interspace. FIG. 100 diagrammatically illustrates outer cylinder 816, inner cylindrical body 818, user actuatable control surface 880 and hole 882.

Figure 101:
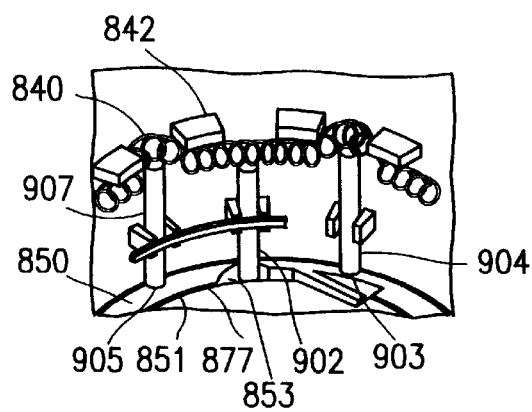
Figure 102:
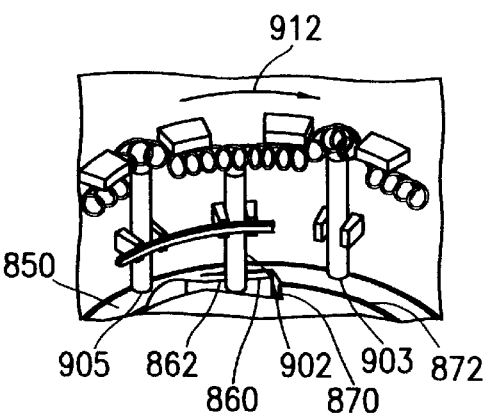

FIGS. 101 and 102 diagrammatically illustrate certain operational aspects of the depending legs. In FIG. 101, depending leg 902 has been axially disposed in interspace 853. Interspace 853 is formed between radially inward edge 851 of locking body 850 and bolt thread 872. The terminal end 903 of depending leg 904 rests on the exposed face of body 850 in a singular radial plane formed by the axial end face of locking body 850. Terminal end 905 is also resting on the end face of locking body 850. As illustrated, biasing spring 840 (or other biasing structure) is a exerting axially outward bias against depending legs 907 and 904. The spring stops, one of which is stop 842, limits axially movement of spring 840. In contrast, the axially outward bias of spring 840 maintains the axially outboard position of depending leg 902 into interspace 853.

In FIG. 102, the removal tool has been rotated as shown in arrow 912. Depending leg 902 has moved proximal tine body 862 radially outward and hence has moved distal tine end 860 out of notch 870 on bolt thread 872. Terminal ends 904 and 903 are riding atop locking body 850. In this manner, the nut can be removed with respect to the bolt.

Figure 103A:
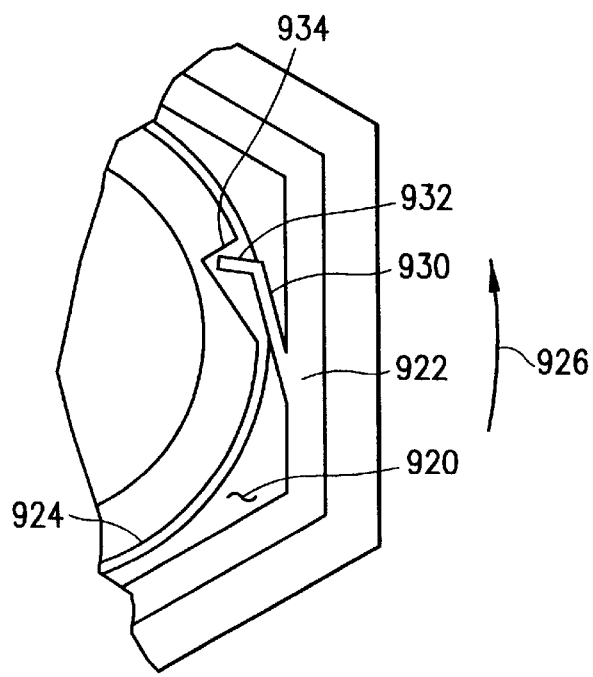
FIG. 103a diagrammatically illustrates a partial, detail end view of a nut carrying the locking body with an interspace identified for insertion of a depending leg; and, FIGS. 103b–115 diagrammatically illustrate blind hole one-way locking fasteners or nut and bolt combination.

FIG. 103*a* diagrammatically illustrates interspace 920 formed between locking body 922 and bolt thread 924. If a depending leg is placed in interspace 920 and moved in the direction shown by arrow 926, proximal tine body 930 moves radially outward which, in turn, moves distal tine end 932 out of notch 934. The locking nut and bolt combination shown in FIG. 103*a* is similar to the nut configuration shown in FIGS. 12, 15 and many other figures herein.

With respect to nuts, bolts, clips, screws and removal tools, general comments follow.

In several embodiments, the system facilitates servicing and removal of the nut or clip by a removal tool, whereby the nut, bolt and locking mechanism can be reused.

The system is enabled to remove and replace a "clip lock" during repairs or servicing while reusing the bolt or screw.

With respect to nuts with built-in removal tool, general comments follow.

A removal system is incorporated within the stamped locking mechanism that will not damage the stamped locking tines and allow reuse of the nut and locking mechanism.

The spacial flex zone allows access for the removal tool in all embodiments discussed herein.

Further, the spacial flex zone allows a removal tool to be incorporated within the locking mechanism and, as such, will not damage the locking tines and will allow the re-use of the system.

FIGS. 103b–112c diagrammatically illustrate various embodiments of the blind hole locking design. FIGS. 103b and 103c diagrammatically illustrate the grooves in the blind hole bolt. The groove configuration in FIG. 103b is similar to the groove in FIG. 6i. The groove in FIG. 103c is similar to the groove 1012 in FIG. 2c. Locking face 2001 abuts the distal tine end (not shown). Opposing slope 2003 defines the balance of the locking zone. In FIG. 103c, the locking zone is defined by locking face 2001, base wall 2008 and rising slope wall 2006. Together, these groove faces or walls form locking zone 2005. The interaction of the tine in these locking zones is discussed earlier.

FIG. 104 shows bolt head 2010 having a recess 2011 which is adapted to receive allen wrenches and various other types of tools. Additionally, bolt head 2010 has the specially configured locking zone 2012 similar to that shown in FIG. 2c.

FIG. 105 diagrammatically illustrates specially configured blind hole bolt 2014 having a plurality of notches or channels 2016 on bolt head 2018. At the axially inboard end of each channel 2016 is a tapered or curvilinear surface 2020. This carved out surface on the underside of bolt or screw head 2018 deflects the tine into groove 2016. This limits or eliminates damage or crushing of the end of the tine.

FIG. 106 diagrammatically shows a rectilinear tine support 2025. The base 2026 of tine carrying box 2025 includes V shaped cutouts 2028 spaced about through bore 2030. The V shaped cutouts 2028 enable the blind hole clip 2025 to properly seat in a beveled blind hole (hole 755 in FIG. 94b) or a funnel shaped blind hole. The hole may be a truncated, frustoconical shape.

FIGS. 107–109 diagrammatically illustrate various shapes for the blind hole, tine carrying structure. In FIG. 108, tine carrying structure 2040 is a polygon or a hexagon. A plurality of tines 2041 extend radially and tangentially into the interior space in which the bolt head passes. Each tine is mounted on a wall segment 2042.

With respect to FIG. 108, tine carrying structure 2040 is a truncated geometric shape. In a similar manner to the blind hole locking system in FIG. 107, tine 2041 is supported and carried by wall 2042. The tine has a spacial flex zone adequate to pass over the non-grooved portions of the bolt or screw head.

In FIG. 109, tine carrying support structure 2040 has a lower, radially disposed plate 2045 which lends additional support to the structure. The term "radial" relates to axial centerline of the bolt or screw.

FIGS. 110a–110c diagrammatically illustrate a blind hole locking system which is mounted atop a structure 2050. The tine support structure 2040 supports and carries a plurality of tines 2041. The bolt head 2051 includes a plurality of locking zones 2052. The bolt passes within through bore 2054 defined in base 2056. Further, tine support 2040 is further supported by base 2056. Base 2056 includes a depending leg 2057. The tine support 2040 and base 2056 is mounted by any reasonable fastening means (nails, screws, rivets, bolts, etc.) to underlying structure 2050. Structure 2050 includes a bore there through 2060 in order to permit the stem of the bolt to pass through structure 2050.

Figure 111A:
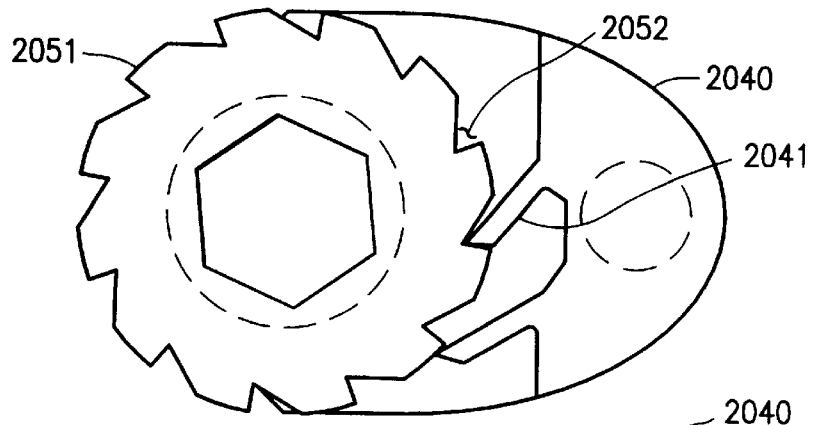

FIGS. 111a–112c diagrammatically illustrate other types of blind hole fastening mechanisms. In FIG. 111a, tine carrying wall 2040 is curved. However, wall 2040 carries a plurality of tines 2041 which interact with locking zones 2052 on bolt head 2051.

Figure 111B:
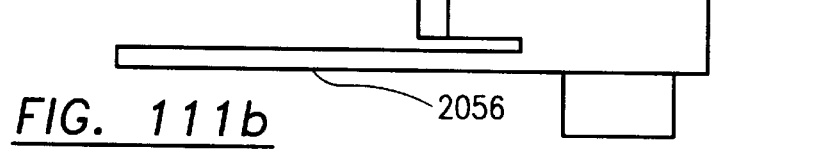

FIG. 111b shows that tine carrying wall 2040 is connected to base 2056. Base 2056 includes a depending leg 2071.

Figure 111C:
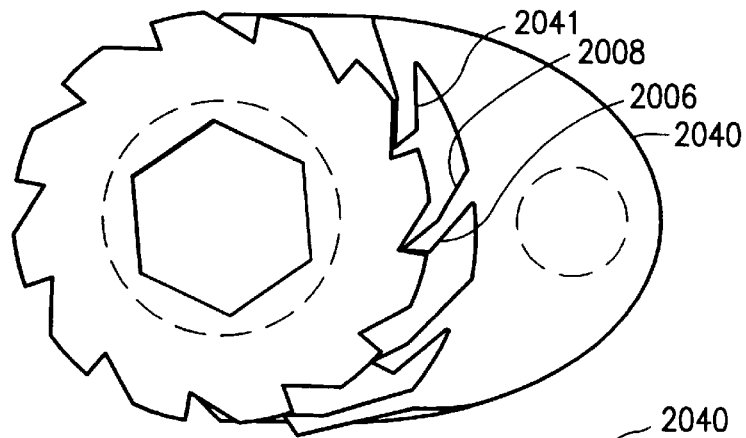

FIG. 111c shows that tine carrying wall 2040 has a plurality of tines 2041 thereon. Tines 2041 each include a distal tine end 2006 which is offset at an angle with respect to tine body 2008.

Figure 111D:
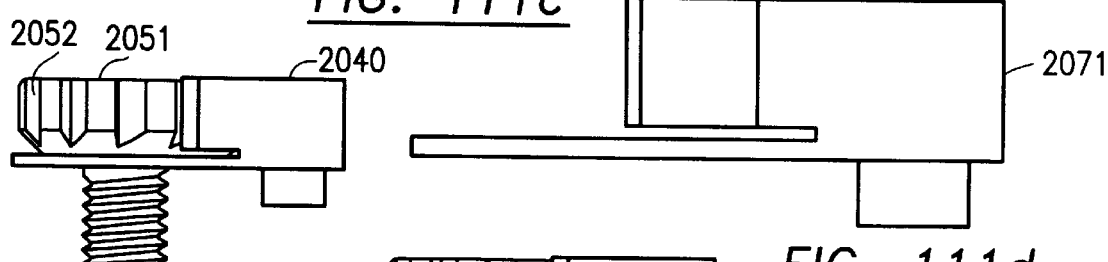

FIG. 111d shows tine carrying wall structure 2040.

Figure 111E:

FIG. 111e shows tine carrying wall 2040 coacting with bolt head 2051. Bolt head 2051 includes a plurality of grooves which define locking zones 2052.

Figure 111F:

FIG. 111f shows that blind hole locking system and tine carrying structure 2040 is mounted on structure 2050. Structure 2050 includes a truncated partial bore 2080 into which is depending disposed leg 2071. See FIG. 111b. Structure 2050 also includes bore 2060 to accommodate the stem of the bolt.

Figure 112A:
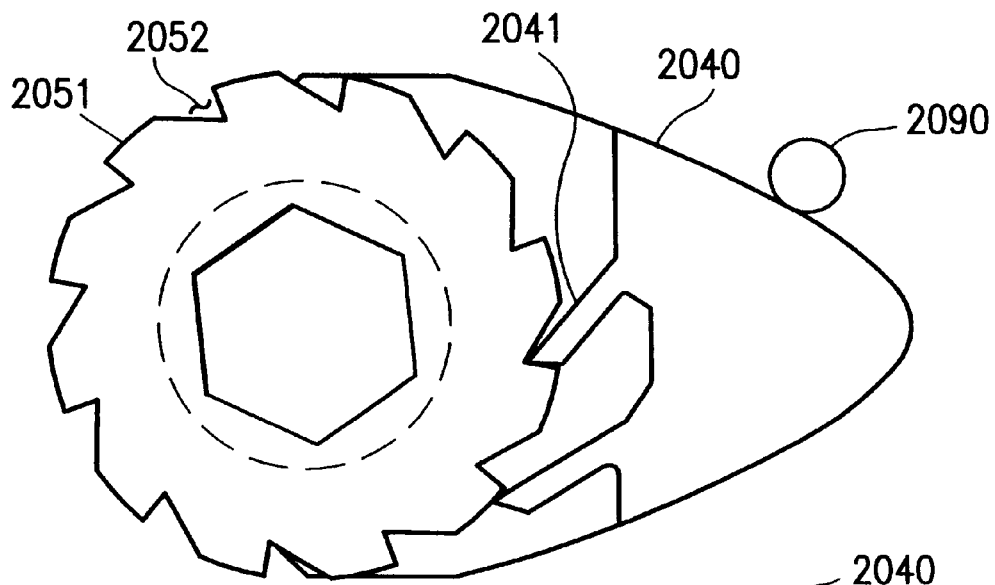
Figure 112B:
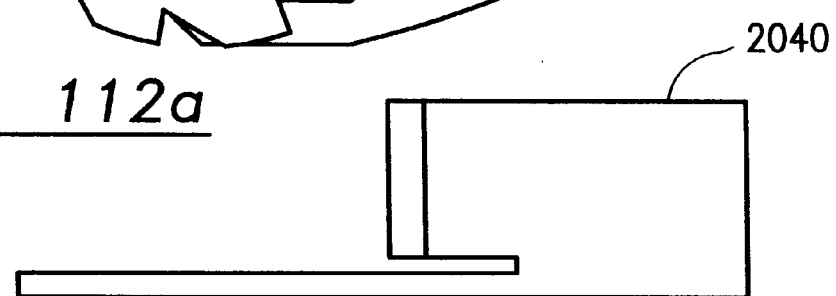

FIG. 112a diagrammatically illustrates tine carrying wall 2040 with a plurality of tines 2041 coacting with locking zones 2052 on bolt head 2051. However, in order to provide a stationary positioning of the tine carrying wall 2040, the structure includes or co-acts with posts 2090. FIG. 112b diagrammatically shows tine carrying wall 2040 and base 2056.

Figure 112C:
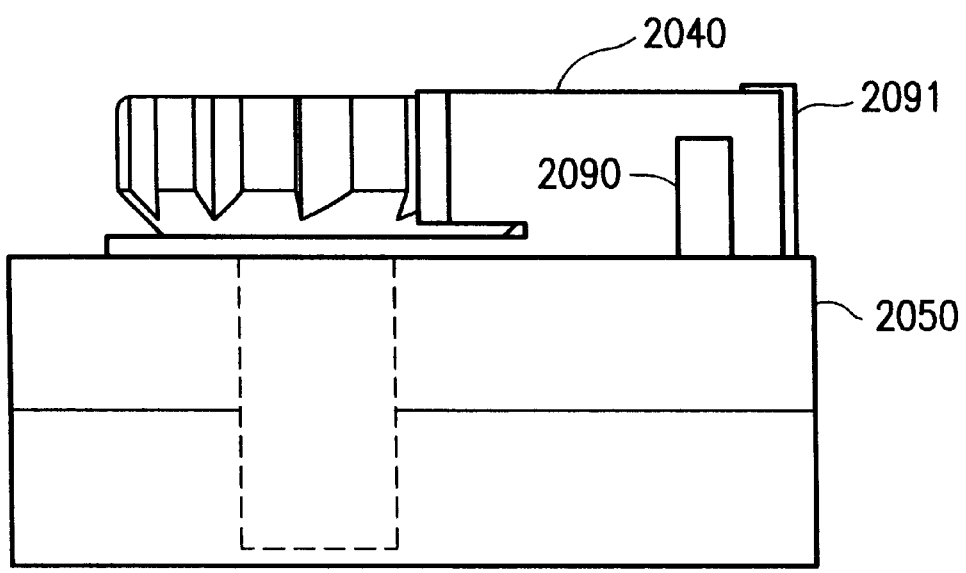

FIG. 112c shows tine carrying wall 2040 locked in place via post 2090 and opposing post 2091. Post 2090 and 2091 arise from base 2050. Alternatively, post 2090 and 2091 may be separate items that are affixed to base 2050. These items may be screws, bolts or poles.

FIGS. 113 and 114 and 115 diagrammatically illustrate other embodiments of the blind hole one-way locking nut and bolt system.

In FIG. 113, blind hole bolt 2200 includes a common bolt head 2202 atop an axially grooved blind hole bolt head section 2204. Threaded bolt stem 2210 depends from blind hole bolt head section 2204. In operation, the locking tines fall into and out of axial grooves 2203 on blind hole bolt section 2204. Counter-rotational movement is prohibited when the locking face of the grooves engages with the tine. See FIGS. 98a and 111a. The presence of common nut, bolt or screw head 2202 atop blind hole bolt head 2204 enables the user to tighten the fastener system onto the underlying structure. Of course, common nut, bolt or screw head section may be hexagonal or allen wrench or straight or phillips screwdriver driven. These systems are covered by the appended claims.

FIG. 114 diagrammatically illustrates a combinatory lug or nut unit 2221 having a common nut head 2223 and grooved blind hole head 2222 with the common nut structure 2223 beneath blind hole head 2222. Further, the blind hole head section 2222 includes an axially inboard bevel 2224. The bevel may be omitted. The bevel facilitates the locking tine action when the blind hole locking nut is threaded onto a bolt stem.

FIG. 115 diagrammatically illustrates combinatory unit 2221 being threaded onto bolt stem 2306. Internal female threads 2308 of unit 2221 are complementary to stem threads 2306. Grooves 2203 enable the blind hole section 2222 to lock onto locking unit 2305 which carries tines 2301. Tines 2301 extend tangentially and radially towards the axial centerline of the unit. Stop ring 2211 limits axially inboard movement of the combinatory unit 2221 inboard toward the left of FIG. 115. Stop ring 2211 acts on axially outboard edge 2309. Alternatively, stem 2306 may extend axially beyond edge 2309 (and possibly well beyond the locking unit wall). Also, the locking unit may be retained in a recess or may be surface mounted. Further, stop 2211 may limit axially inboard movement of a socket acting on nut surface 2221. In the absence of a radially extending ridge or stop 2211, the blind hole groove segment 2222 may be radially larger than nut segment 2221. The radially larger grooved segment will stop axially inboard movement of the socket.

Segmenting rim 2211 acts as a stop to the common driver for the bolt or lug stem. Also the blind hole bolt head section 2204,2222 has a smaller radii than the common nut, bolt or screw head. This enables the common driver to easily grasp the common drive head. The smaller size is also useful in mechanically sensing the blind hole bolt head grooves. Alternatively, the grooved section may be radially larger.

In another embodiment, the blind hole fastening system can be mounted on a leg of a clip. In this embodiment, the locking unit (carrying one or more tines) is mounted on a leg of a clip. The clip is placed on a generally planar, underlying structure. Somewhere, either on the underlying structure or otherwise disposed adjacent thereto, a nut or a nut thread carrying unit is disposed. The nut thread may be located on another clip leg. The specially configured blind hole bolt (the bolt with a groove carrying head) is inserted into the axial through bore of the locking unit, inserted into the bore on the clip leg (which may be the locking nit bore), inserted through the bore on the underlying structure and ultimately the male thread on the blind hole bolt engages the nut thread. One way rotation is permitted when the blind hole bolt head enages the tines in the locking unit.

The claims appended hereto are meant to cover modifications and changes within the scope and spirit of the present invention.

What is claimed is:

1. An S-shaped locking nut and bolt assembly for a bored panel comprising:

an elongated bolt having a stem and a bolt thread on said stem, said bolt thread defining bolt thread crest and bolt thread troughs, said bolt having a plurality of notches defined on said bolt thread generally longitudinally in a predetermined pattern with proximal notches being longitudinally adjacent each other on said bolt thread, each notch having a lock face and an opposing slope on said bolt thread which form a locking channel on said stem;

an S-shaped member having first, second and third elongated, generally planar legs;

a nut formed on one of said second and said third legs, said nut having a nut thread about an axial centerline which is complementary to said bolt thread;

a locking element formed on the other of said second and third legs, said locking element having a locking element bore coaxial with respect to said axial centerline, said locking element having a plurality of axially protruding legs perpendicular to said planar other leg and having a corresponding plurality of tines, each tine protruding tangentially and radially inward toward said axial centerline, said axially protruding legs depending from said planar other leg, each said tine having a distal tine end adapted to latch on said lock face of said notch and a proximal tine portion attached to said corresponding axially protruding leg;

said S-shaped member adapted to be mounted on said panel with said axial centerline of said nut, said panel bore and said locking element bore being substantially coaxially aligned;

one of said plurality of distal tine ends being adapted to move radially inward when said distal tine end is disposed in one or more notches and move radially outward when said distal tine end rides on said bolt thread crest, and the position of said distal tine end being visible due to the disposition of said elongated locking element on said third leg.

2. A locking nut and bolt assembly as claimed in claim 1 wherein said plurality of tines are disposed circumferentially about said locking element bore.

3. An S-shaped locking nut assembly for a bored panel and an elongated bolt having a stem and a bolt thread on said stem, said bolt thread defining bolt thread crest and bolt thread troughs, said bolt having a plurality of notches defined on said bolt thread generally longitudinally in a predetermined pattern with proximal notches being longitudinally adjacent each other on said bolt thread, each notch having a lock face and an opposing slope on said bolt thread which form a locking channel on said stem, said locking nut assembly comprising:

an S-shaped member having first, second and third elongated, generally planar legs;

a nut formed on one of said second and said third legs, said nut having a nut thread about an axial centerline which is complementary to said bolt thread;

an elongated locking unit formed on the other of said second and said third legs, said locking unit formed as a cylinder with its cylindrical axis perpendicular to the plane of said other leg, said locking unit having at least one tine protruding tangentially and radially inward toward said cylindrical axis, said tine having a distal tine end adapted to latch on said lock face of said notch and a proximal tine portion adjacent said cylinder, said cylinder defining a cut-out at said tine;

said S-shaped member adapted to be mounted on said panel with said axial centerline of said nut, said panel bore and said cylindrical axis of said locking unit being substantially coaxially aligned;

said distal tine end being adapted to move radially inward when said distal tine end is disposed in one or more notches and move radially outward when said distal tine end rides on said bolt thread crest, and the position of said distal tine end being visible due to the disposition of said elongated locking unit on said other leg.

4. A locking nut assembly as claimed in claim 3 wherein said cylinder carries a plurality of tines protruding tangentially and radially toward said axial centerline, said plurality of tines disposed circumferentially about said cylinder.

5. An S-shaped locking nut assembly for a bored panel and an elongated bolt having a stem and a bolt thread on said stem, said bolt thread defining bolt thread crest and bolt thread troughs, said bolt having a plurality of notches defined on said bolt thread generally longitudinally in a predetermined pattern with proximal notches being longitudinally adjacent each other on said bolt thread, each notch having a lock face and an opposing slope on said bolt thread which form a locking channel on said stem, said locking nut assembly comprising:

an S-shaped member having first, second and third elongated, generally planar legs;

a nut formed on one of said second and said third legs, said nut having a nut thread about an axial centerline which is complementary to said bolt thread;

a locking element formed on the other of said second and said third legs, said locking element having a locking element bore coaxial with respect to said axial centerline, said locking element having a plurality of axially protruding legs perpendicular to said planar other leg and having a corresponding plurality of tines, each tine protruding tangentially and radially inward toward said axial centerline, said axially protruding legs depending from said planar other leg, each said tine having a distal tine end adapted to latch on said lock face of said notch and a proximal tine portion attached to said corresponding axially protruding leg;

said S-shaped member adapted to be mounted on said panel with said axial centerline of said nut, said panel bore and said locking element bore being substantially coaxially aligned;

one of said plurality of distal tine ends being adapted to move radially inward when said distal tine end is disposed in one or more notches and move radially outward when said distal tine end rides on said bolt thread crest, and the position of said distal tine end being visible due to the disposition of said elongated locking element on said other leg.

6. A locking nut assembly as claimed in claim 5 wherein said plurality of tines are disposed circumferentially about said locking element bore.

* * * * *